United States Patent
Wang et al.

(10) Patent No.: US 11,377,636 B2
(45) Date of Patent: Jul. 5, 2022

(54) ENDOGENOUS RETROVIRUS TRANSCRIPTION AS A MARKER FOR PRIMATE NAIVE PLURIPOTENT STEM CELLS

(71) Applicants: Max-Delbrück-Centrum für Molekulare Medizin in der Helmholtz-Gemeinschaft, Berlin (DE); University of Bath, Bath (GB)

(72) Inventors: Jichang Wang, Berlin (DE); Zsuzsanna Izsvák, Berlin (DE); Laurence Daniel Hurst, Wiltshire (GB)

(73) Assignees: Max-Delbrück-Centrum für Molekulare Medizin in der Helmholtz-Gemeinschaft, Berlin (DE); UNIVERSITY OF BATH, North East Somerset (GB)

( * ) Notice: Subject to any disclaimer, the term of this patent is extended or adjusted under 35 U.S.C. 154(b) by 322 days.

(21) Appl. No.: 16/563,089

(22) Filed: Sep. 6, 2019

(65) Prior Publication Data
US 2020/0063096 A1    Feb. 27, 2020

Related U.S. Application Data

(63) Continuation of application No. 15/517,904, filed as application No. PCT/EP2015/073144 on Oct. 7, 2015, now abandoned.

(30) Foreign Application Priority Data

Oct. 7, 2014    (DE) ..................... 10 2014 114 558.5

(51) Int. Cl.
| | | |
|---|---|---|
| C12Q 1/68 | (2018.01) | |
| C12N 15/63 | (2006.01) | |
| A61K 35/12 | (2015.01) | |
| C07H 21/04 | (2006.01) | |
| C12N 5/0735 | (2010.01) | |
| C12N 5/074 | (2010.01) | |

(52) U.S. Cl.
CPC ......... *C12N 5/0606* (2013.01); *C12N 5/0696* (2013.01); *C12N 2500/90* (2013.01); *C12N 2500/98* (2013.01); *C12N 2501/065* (2013.01); *C12N 2501/115* (2013.01); *C12N 2501/15* (2013.01); *C12N 2501/155* (2013.01); *C12N 2501/16* (2013.01); *C12N 2501/235* (2013.01); *C12N 2501/2306* (2013.01); *C12N 2501/2311* (2013.01); *C12N 2501/33* (2013.01); *C12N 2501/41* (2013.01); *C12N 2501/415* (2013.01); *C12N 2501/42* (2013.01); *C12N 2501/727* (2013.01); *C12N 2510/00* (2013.01)

(58) Field of Classification Search
CPC ...... C12Q 1/68; C12N 5/0606; C12N 5/0696; C12N 15/63; C12N 2510/00; C12N 2500/98; C07H 21/04
See application file for complete search history.

(56) References Cited

U.S. PATENT DOCUMENTS

| | | |
|---|---|---|
| 2010/0041137 A1 | 2/2010 | Smith et al. |
| 2012/0272349 A1 | 10/2012 | Ochiya et al. |
| 2014/0309131 A1 | 10/2014 | Yamanaka et al. |
| 2016/0122718 A1 | 5/2016 | Braam |
| 2017/0275593 A1 | 9/2017 | Hanna et al. |
| 2018/0112187 A1 | 4/2018 | Smith et al. |

FOREIGN PATENT DOCUMENTS

WO    WO 2013/014929 A1    1/2013

OTHER PUBLICATIONS

International Search Report and Written Opinion in PCT/EP2015/073144 dated Jan. 5, 2016.
Gafni, et al. 2013 "Derivation of novel human ground state naïve pluripotent stem cells" *Nature* 504: 282-286 (with associated supplemental information), in 20 pages.
Kim, et al. 2013 "Modulation of β-catenin function maintains mouse epiblast stem cell and human embryonic stem cell self-renewal" *Nature Communications* 4: 1-12.
Leeb, et al. 2014 "Genetic exploration of the exit from self-renewal using haploid embryonic stem cells" *Cell Stem Cell* 14(3): 385-393.
Ohnuki, et al. 2014 "Dynamic regulation of human endogenous retroviruses mediates factor-induced reprogramming and differentiation potential" *Proceedings of the National Academy of Sciences* 111(34): 12426-12431.
Parseval, et al. 1999 "The long terminal repeats of the HERV-H human endogenous retrovirus contain binding sites for transcriptional regulation by the Myb protein" *Journal of General Virology* 80: 841-845.
Santoni, et al. 2012 "Herv-H RNA is abundant in human embryonic stem cells and a precise marker for pluripotency" *Retrovirology* 9(1): 1-16.
Theunissen, et al. 2014 "Systematic identification of culture conditions for induction and maintenance of naïve human pluripotency" *Cell Stem Cell* 15(4): 471-487.

(Continued)

*Primary Examiner* — Shin Lin Chen
(74) *Attorney, Agent, or Firm* — Knobbe, Martens, Olson & Bear, LLP

(57) ABSTRACT

An in vitro method for identifying, isolating and/or enriching primate naive pluripotent stem cells, the method including analyzing transcription of a type 7 long terminal repeat (LTR7) nucleic acid sequence of a type H human endogenous retrovirus (HERVH) (LTR7/HERVH-associated transcription), and identifying, isolating and/or enriching primate naive pluripotent stem cells based on LTR7/HERVH-associated transcription, wherein LTR7/HERVH-associated transcription is a marker for primate naive pluripotent stem cells. An isolated in vitro population of primate naive pluripotent stem cells is obtained by the method, wherein in the cells LTR7/HERVH-associated transcription is elevated in comparison to control cells, wherein control cells are primed pluripotent stem cells or differentiated cells.

13 Claims, 51 Drawing Sheets
Specification includes a Sequence Listing.

(56) References Cited

OTHER PUBLICATIONS

Wang, et al. 2014 "Primate-specific endogenous retrovirus-driven transcription defines naïve-like stem cells" Nature 516(7531): 405-409.
Xu, et al. 2014 "A simple and effective method for the isolation of inner cell mass samples from human blastocysts for gene expression analysis" In Vitro Cellular & Developmental Biology—Animal 50(3): 232-236.
Bellucci et al., "Predicting protein associations with long noncoding RNAs", Nature Methods, 8(6):444-445 (2011).
Chan et al., "Induction of a Human Pluripotent State with Distinct Regulatory Circuitry that Resembles Preimplantation Epiblast", Cell Stem Cell, 13:663-675 (2013).
Chappell et al., "MYC/MAX control ERK signaling and pluripotency by regulation of dual-specificity phosphatases 2 and 7", Genes & Development, 27:725-733 (2013).
Chen et al., "Integration of External Signaling Pathways with the Core Transcriptional Network in Embryonic Stem Cells", Cell, 133:1106-1117 (2008).
Cong et al., "Multiplex Genome Engineering Using CRISPR/Cas Systems", Science, 339 (6121):819-823 (2013).
Dobin et al., "STAR: ultrafast universal RNA-seq aligner", Bioinformatics Original Paper, 29(1):15-21 (2013).
Dunn et al., "Defining an essential transcription factor program for naïve pluripotency", Science, 344(6188):1156-1160 (2014).
Ernst et al., "Discovery and characterization of chromatin states for systematic annotation of the human genome", Nature Biotechnology, 28(8):817-827 (2010).
Fort et al., "Deep transcriptome profiling of mammalian stem cells supports a regulatory role for retrotransposons in pluripotency maintenance", Nature Genetics, 46(6):558-568 (2014).
Frith et al., "Detection of functional DNA motifs via statistical over-representation" Nucleic Acids Research, 32(4): 1372-1381 (2004).
Gafni et al., "Derivation of novel human ground state naïve pluripotent stem cells", Nature, 504:282-301 (2013).
Gaspar-Maia et al., "Chd1 regulates open chromatin and pluripotency of embryonic stem cells", Nature, 460:863-870 (2009).
Grabundzija et al., "Sleeping Beauty transposon-based system for cellular reprogramming and targeted gene insertion in induced pluripotent stem cells" Nucleic Acids Research, 41(3):1829-1847 (2013).
Haase et al., "Generation of Induced Pluripotent Stem Cells from Human Cord Blood", Cell Stem Cell, 5:434-441 (2009).
Hanna et al., "Metastable Pluripotent States in NOD-Mouse-Derived ESCs", Cell Stem Cell, 4:513-524 (2009).
Hanna et al., "Human embryonic stem cells with biological and epigenetic characteristics similar to those of mouse ESCs", PNAS, 107(20):9222-9227, (2010).
Haverty et al., "Computational inference of transcriptional regulatory networks from expression profiling and transcription factor binding site identification", Nucleic Acids Research, 32(1):179-188 (2004).
Havugimana et al., "A Census of Human Soluble Protein Complexes", Cell, 150:1068-1081 (2012).
Ivics et al., "Molecular Reconstruction of Sleeping Beauty, a Tc1-like Transposon from Fish, and Its Transposition in Human Cells", Cell, 91:501-510 (1997).
Kaufman et al., "Frog Prince transposon-based RNAi vectors mediate efficient gene knockdown in human cells", Journal of RNAi and Gene Silencing, 1(2):97-104 (2005).
Kelley et al., "Transposable elements reveal a stem cell-specific class of long noncoding RNAs", Genome Biology, 13:R107, pp. 1-14 (2012).
Kong et al., "CPC: assess the protein-coding potential of transcripts using sequence features and support vector machine", Nucleic Acids Research, vol. 35(Web Server issue):W345-W349 (2007).
Kunarso et al., "Transposable elements have rewired the core regulatory network of human embryonic stem cells", Nature Genetics, 42(7):631-635 (2010).
Langmead et al., "Fast gapped-read alignment with Bowtie 2", Nature Methods, 9(4):357-360 (2012).
Liao et al., "featureCounts: an efficient general purpose program for assigning sequence reads to genomic features", Bioinformatics Original Paper, 30(7):923-930 (2014).
Loewer et al., "Large intergenic non-coding RNA-RoR modulates reprogramming of human induced pluripotent stem cells", Nature Genetics, 42(12):1113-1120 (2010).
Lu et al., "The retrovirus HERVH is a long noncoding RNA required for human embryonic stem cell identity", Nature Structural & Molecular Biology, 21(4):423-427 (2014).
MacFarlan et al., "Embryonic stem cell potency fluctuates with endogenous retrovirus activity", Nature, 487:57-65 (2012).
Martello et al., "Identification of the missing pluripotency mediator downstream of leukaemia inhibitory factor", The EMBO Journal 32:2561-2574 (2013).
Mátés et al., "Molecular evolution of a novel hyperactive Sleeping Beauty transposase enables robust stable gene transfer in vertebrates", Nature Genetics, 41(6):753-761 (2009).
Neph et al., "An expansive human regulatory lexicon encoded in transcription factor footprints", Nature, 489:83-90 (2012).
Ng et al., "Human long non-coding RNAs promote pluripotency and neuronal differentiation by association with chromatin modifiers and transcription factors", The EMBO Journal, 31:522-533 (2012).
Nichols et al., "Naive and Primed Pluripotent States", Cell Stem Cell, 4:487-492 (2009).
Nishiyama et al., "Systematic repression of transcription factors reveals limited patterns of gene expression changes in ES cells", Scientific Reports, 3:1390, pp. 1-6 (2013).
Okamoto et al., "Eutherian mammals use diverse strategies to initiate X-chromosome inactivation during development", Nature, 472:370-376 (2011).
Onder et al., "Chromatin-modifying enzymes as modulators of reprogramming", Nature, 483:598-604 (2012).
Pohl et al., "bwtool: a tool for bigWig files", Bioinformatics Applications Note, 30(11):1618-1619 (2014).
Prigione et al., "The Senescence-Related Mitochondrial/Oxidative Stress Pathway is Repressed in Human Induced Pluripotent Stem Cells", Stem Cells, 28:721-733 (2010).
Quinlan et al., "BEDTools: a flexible suite of utilities for comparing genomic features", Bioinformatics Applications Note, 26(6):841-842 (2010).
Ramsköld et al., "Full-length mRNA-Seq from single-cell levels of RNA and individual circulating tumor cells", Nature Biotechnology, 30(8):777-785 (2012).
Takahashi et al., "Induction of Pluripotent Stem Cells from Adult Human Fibroblasts by Defined Factors" Cell, 131:861-872 (2007).
To et al., "Modulation of CP2 Family Transcriptional Activity by CRTR-1 and Sumoylation", PLoS ONE, 5(7):1-13 (2010).
Trapnell et al., "TopHat: discovering splice junctions with RNA-Seq", Bioinformatics Original paper, 25(9):1105-1111 (2009).
Van Den Berg et al., "An Oct4-Centered Protein Interaction Network in Embryonic Stem Cells", Cell Stem Cell 6, pp. 369-381 (2010).
Vassena et al., "Waves of early transcriptional activation and pluripotency program initiation during human preimplantation development", Development 138:3699-3709 (2011).
Volders et al., "LNCipedia: a database for annotated human lncRNA transcript sequences and structures", Nucleic Acids Research, vol. 41 (Database issue): D246-D251 (2013).
Wang et al., "Distinct Lineage Specification Roles for NANOG, OCT4, and SOX2 in Human Embryonic Stem Cells", Cell Stem Cell 10:440-454 (2012).
Ware et al., "Derivation of naive human embryonic stem cells", PNAS, 111(12):4484-4489 (2014).
Welling et al., "Uncovering the true identity of naive pluripotent stem cells", Trends in Cell Biology, 23(9):442-448 (2013).
Xie et al., "Epigenomic Analysis of Multilineage Differentiation of Human Embryonic Stem Cells", Cell, 153:1134-1148 (2013).

(56) References Cited

OTHER PUBLICATIONS

Yan et al., "Single-cell RNA-Seq profiling of human preimplantation embryos and embryonic stem cells", Nature Structural & Molecular Biology, 20(9):1131-1142 (2013).
Ye et al., "Embryonic stem cell self-renewal pathways converge on the transcription factor Tfcp2l1", The EMBO Journal, 32:2548-2560 (2013).
Zhang et al., "Model-based Analysis of ChIP-Seq (MACS)", Genome Biology, 9:R137-R137.9 (2008).
Zhou et al., "Induction of Human Fetal Globin Gene Expression by a Novel Erythroid Factor, NF-E4", Molecular and Cellular Biology, 20(20): 7662-7672 (2000).

| JASPAR ID / Motif | HERVH vs GC (CLOVER P-value) | LTR7 vs LTR7C/Y (ROVER P-value) | LTR7 vs moderately active HERVH (ROVER P-value) | HERVH vs HERVK (CLOVER P-Value) |
|---|---|---|---|---|
| MA0145.1_Tcfcp2l1(LBP9) | 0.001 | 8.30E-36 | 0.000576175 | 0 |
| MA0035.2_Gata1 | 0 | 2.40E-27 | >0.05 | >0.05 |
| MA0109.1_Hltf | 0 | 1.17E-18 | >0.05 | >0.05 |
| MA0063.1_Nkx2-5 | 0.002 | 9.80E-15 | 0.000265626 | >0.05 |
| MA0259.1_HIF1A::ARNT | 0 | 1.47E-14 | >0.05 | 0 |
| MA0047.2_Foxa2 | 0 | 1.43E-08 | >0.05 | 0 |
| MA0148.1_FOXA1 | 0 | 8.38E-07 | >0.05 | 0 |
| MA0101.1_REL | 0 | 0.000411012 | >0.05 | >0.05 |
| MA0143.1_Sox2 | 0.001 | 0.00150613 | >0.05 | >0.05 |
| MA0055.1_Myf | 0 | 0.00229056 | >0.05 | >0.05 |
| MA0140.1_Tal1::Gata1 | 0 | 0.00700998 | >0.05 | >0.05 |
| MA0144.1_Stat3 | 1 | 5.80E-83 | 0.000910078 | >0.05 |
| MA0066.1_PPARG | 1 | 9.08E-75 | 9.99E-06 | >0.05 |
| MA0007.1_Ar | 0.989 | 3.37E-45 | 0.000755461 | >0.05 |
| MA0158.1_HOXA5 | 1 | 2.34E-08 | >0.05 | >0.05 |
| MA0135.1_Lhx3 | 0.999 | 1.17E-07 | >0.05 | >0.05 |
| MA0137.2_STAT1 | 0.994 | 2.62E-06 | >0.05 | >0.05 |
| MA0113.1_NR3C1 | 1 | 6.50E-06 | >0.05 | >0.05 |
| MA0048.1_NHLH1 | 1 | 7.14E-06 | >0.05 | >0.05 |
| MA0163.1_PLAG1 | 1 | 4.51E-05 | >0.05 | >0.05 |
| MA0099.2_AP1 | 0.982 | 6.82E-05 | >0.05 | >0.05 |
| MA0025.1_NFIL3 | 1 | 0.000107307 | >0.05 | >0.05 |
| MA0078.1_Sox17 | 1 | 0.000281809 | >0.05 | >0.05 |
| MA0030.1_FOXF2 | 1 | 0.000616575 | >0.05 | >0.05 |
| MA0139.1_CTCF | 1 | 0.00160586 | >0.05 | >0.05 |
| MA0040.1_Foxq1 | 1 | 0.00233706 | >0.05 | 0 |
| MA0014.1_Pax5 | 1 | 0.00235216 | >0.05 | >0.05 |
| MA0102.2_CEBPA | 0.958 | 0.00535611 | >0.05 | >0.05 |

| Gene | association with HERVH | Gene functions | References |
|---|---|---|---|
| ABCG2 | alternative promoter | Prevent mESC differentiation | PMID: 19670287 |
| ABCG2 | alternative promoter | quality of hiPSCs | PMID: 19826408 |
| ABHD12B | chimeric transcript | Block hiPSC differentiation into neurons | PMID: 24259714 |
| CALB1 | chimeric transcript | epigenetic regulation of G9a, REST, marker for ESCs | PMID: 19752176 |
| ESRG | HERVH-derived gene | maintain the pluripotent state of hPSCs | this study |
| GAL | upstream | marker for hESC | PMID: 23336433 |
| GRID2 | intron/upstream | association with neuronal diseases | PMID: 23611888 |
| GUCY2C | chimeric transcript | prevent TGF-beta secretion | PMID: 24085786 |
| HHLA1 | chimeric transcript | Block hiPSC differentiation into neurons | PMID: 24259714 |
| OC90 | chimeric transcript | Block hiPSC differentiation into neurons | PMID: 24259714 |
| HIF3A | upstream | regulate pluripotency and proliferation of ESCs | PMID: 19755485 |
| IL6 | upstream | self-renewal reprogramming | PMID: 23995732 |
| LEPREL1 | upstream | differentiation response to BMP4 and Activin | PMID: 22893457 |
| POU5F1B | chimeric transcript | The OCT4 pseudogene | PMID: 24362523 |
| RPL39L | chimeric transcript | enriched in ESCs | PMID: 24452241 |
| SCGB3A2 | chimeric transcript | repress TGF-beta signaling pathway | PMID: 21478551 |
| SLC22A2 | upstream | gene imprinting | PMID: 21161363 |
| WNT16 | upstream | Wnt signaling pathway | PMID: 21654806 |
| PLP1 | chimeric transcript | neuronal differentiation | PMID: 22695888 |
| DNMT3B | alternative promoter | maintain the primed pluripotent state of ESCs | PMID: 23850245 |

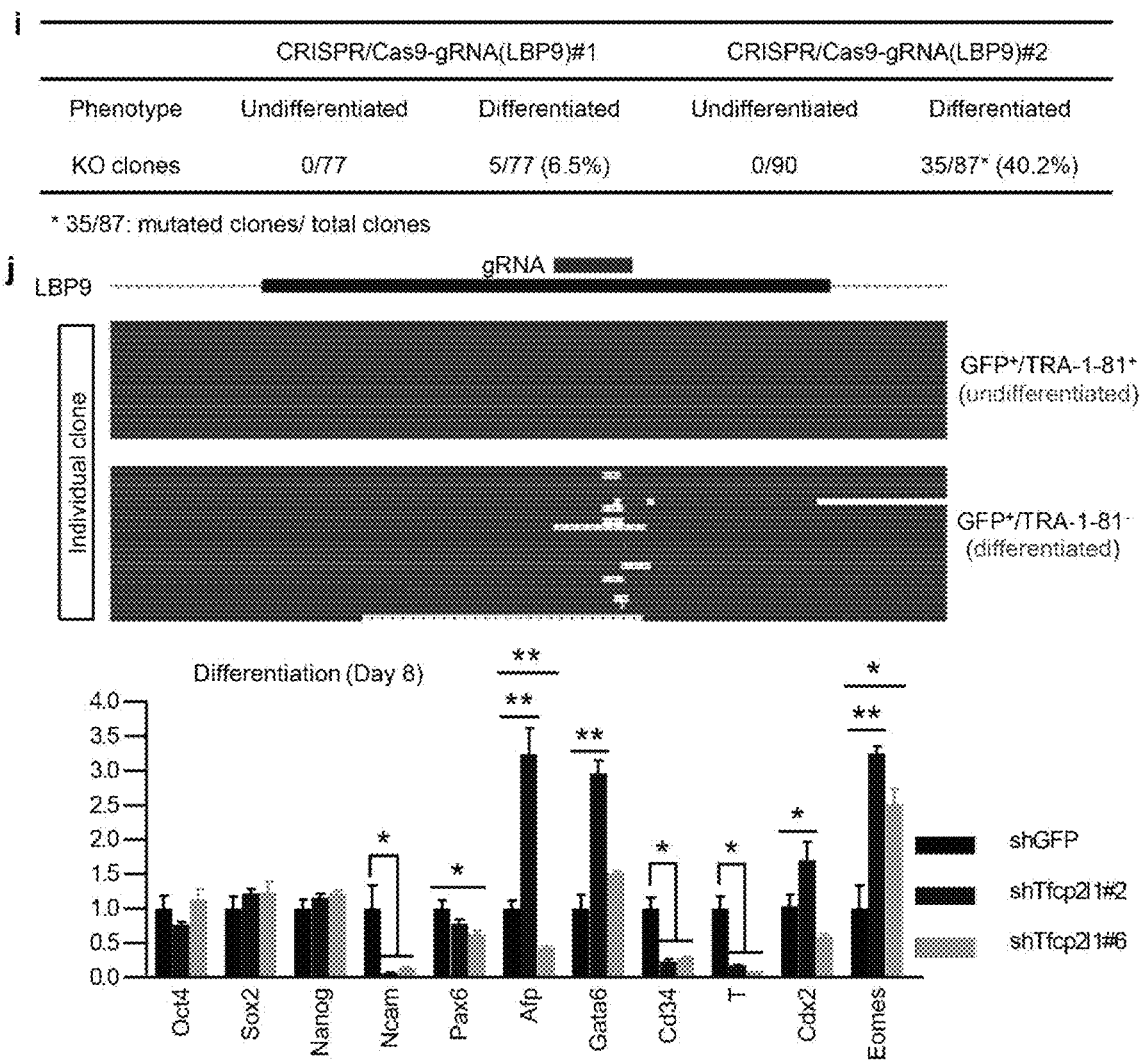

| Morphology | 2i/LIF | NHSM | 3iL | KOSR | mTeSR1 |
|---|---|---|---|---|---|
| 3D/GFP(high) | 162 (35.1%) | 202 (44.0%) | 196 (42.2%) | 22 (5.7%) | 15 (3.4%) |
| 2D/GFP(low) | 59 (12.8%) | 42 (9.2%) | 33 (7.1%) | 204 (52.6%) | 208 (47.1%) |
| mosaic | 104 (22.5%) | 116 (25.3%) | 139 (30.0%) | 115 (29.6%) | 136 (30.8%) |
| 3D/GFP(-) | 96 (20.8%) | 78 (17.0%) | 80 (17.2%) | 7 (1.8%) | 5 (1.1%) |
| 2D/GFP(-) | 41 (8.9%) | 21 (4.6%) | 16 (3.4%) | 40 (10.3%) | 78 (17.6%) |

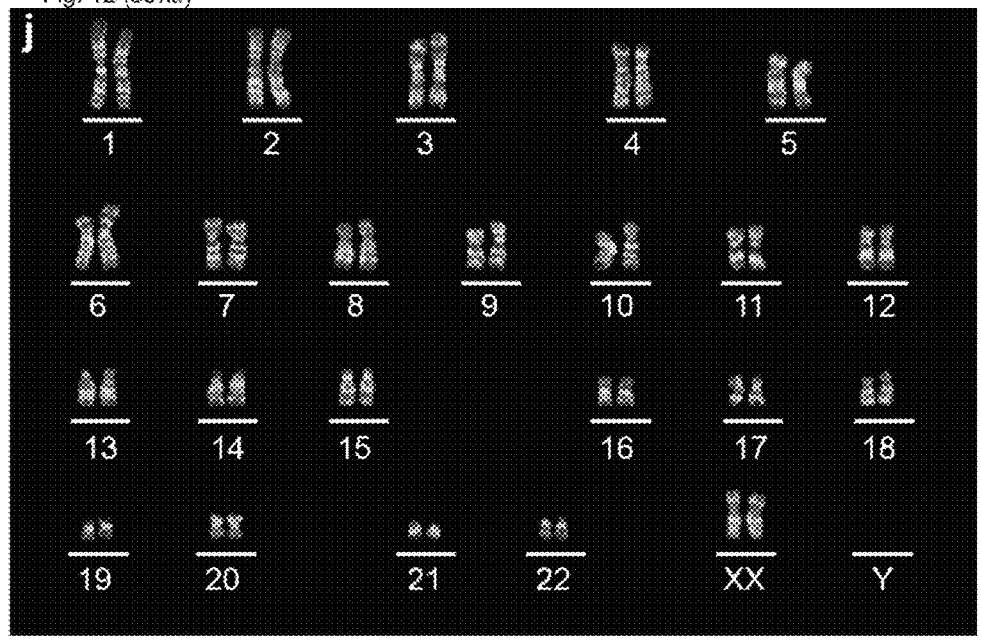
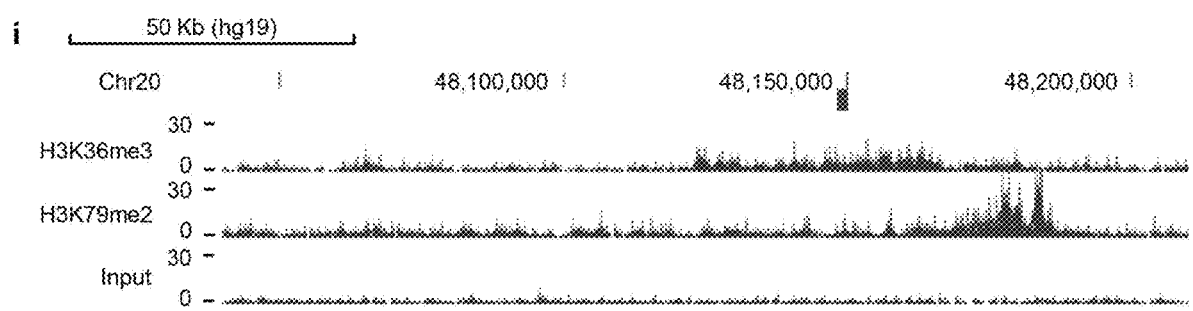

ENDOGENOUS RETROVIRUS TRANSCRIPTION AS A MARKER FOR PRIMATE NAIVE PLURIPOTENT STEM CELLS

FIELD OF THE INVENTION

The present invention relates to the use of one or more type 7 long terminal repeat (LTR7) nucleic acid sequences of type H human endogenous retroviruses (HERVH) ("LTR7/HERVH nucleic acid sequences") for identifying primate naive pluripotent stem cells. The invention is directed to the use of LTR7/HERVH nucleic acid sequences as a marker, wherein LTR7/HERVH-associated transcription is used as a marker for primate naive pluripotent stem cells. The invention also relates to a reporter construct comprising LTR7/HERVH nucleic acid sequences in addition to the use of said reporter, in particular for optimizing culture conditions for naïve primate pluripotent stem cells. The invention also relates to a cell growth medium for cultivation of primate naive pluripotent stem cells that preferably exhibit elevated levels of LTR7/HERVH-associated transcription in comparison to control cells.

REFERENCE TO SEQUENCE LISTING

A Sequence Listing submitted as an ASCII text file via EFS-Web is hereby incorporated by reference in accordance with 35 U.S.C. § 1.52(e). The name of the ASCII text file for the Sequence Listing is 31273065_1.TXT, the date of creation of the ASCII text file is Sep. 6, 2019, and the size of the ASCII text file is 5.9 KB.

BACKGROUND OF THE INVENTION

Naïve embryonic stem cells (ESCs) hold great promise for research and therapeutics as they have broad and robust developmental potential. While such cells are readily derived from mouse blastocysts it has been impossible to easily isolate human equivalents[1,2], although human naïve-like cells have been artificially generated (rather than extracted) by coercion of human primed ES cells by modifying culture conditions[2-4] or through transgenic modifications[5].

Despite the progress made in establishing culture conditions for selecting and maintaining naïve pluripotent stem cells (PSCs), improvements are required that enable a more reliable identification and subsequent prolonged culturing of said cells from stem cell populations.

Transcription of LTR sequences has been observed in stem cell populations, but has not been proposed as an effective marker for identifying and/or selecting naïve stem cells. Ohnuki et al (PNAS, 2014, v. 111, no. 34.) discloses transient hyperactivation of LTR7 sequences during iPSC generation. Induction of LTR7 expression is mediated by OCT3/4, SOX2, and KLF4. Ohnuki et al state that when reprogramming is complete and cells acquire full pluripotency, LTR7 activity decreases to levels comparable with those in ESCs. According to Ohnuki et al, failure to reduce the LTR7 activity is postulated to lead to a differentiation defective phenotype, thereby teaching that LTR7 transcription is not suitable as a marker for naïve PSCs.

WO 2013/014929 discloses a method and means for screening iPSC for differentiation resistance using large intergenic non-coding RNAs or specific mRNA sequences. According to WO 2013/014929, iPSCs without differentiation resistance are characterised by the absence of expression of particular LTR7 sequences that exhibit increased levels of DNA methylation and reduced expression in iPSCs without differentiation resistance. In summary, both Ohnuki et al and WO 2013/014929 fail to identify the relevance of LTR transcription with respect to the identification and maintenance of the naïve state of naive PSCs.

Alternative approaches described in the prior art have employed a reporter system for naive human pluripotency based on OCT4 distal enhancer activity combined with an optimized culture medium for cultivation of naïve PSCs[27] (Theunissen et al., Cell Stem Cell. 2014, 15(4): 471). Although some success has been achieved using such approaches, the cells obtained by these methods show reduced genome stability that is disadvantageous for later use (such as therapeutic use) of the cells or cells derived therefrom.

SUMMARY OF THE INVENTION

The present invention demonstrates that a sub-population of cells within cultures of human ESCs (hESCs) and induced pluripotent stem cells (hiPSCs) manifest key properties of naïve state cells. These "naïve-like" cells (or naïve pluripotent stem cells) can be identified by elevated transcription of HERVH, a primate-specific endogenous retrovirus (ERV). HERVH elements provide functional binding sites for a combination of naïve pluripotency transcription factors, including LBP9, OCT4, NANOG and KLF4. LBP9 was recently recognized as relevant to naivety in mice[6]. LBP9/HERVH drives hESC-specific alternative and chimeric transcripts, including pluripotency modulating long non-coding RNAs (lncRNAs). Disruption of LBP9, HERVH and HERVH-derived transcripts compromises self-renewal. These observations define HERVH expression as a feature of naïve hESCs, establish novel primate-specific transcriptional activity regulating pluripotency and enable the use of HERVH elements in the identification and/or separation of naïve-like hESCs from a cell mixture, such as embryonic cells or extracts thereof, or from hiPS cells.

In light of the prior art the technical problem underlying the present invention is to provide improved or alternative means for identifying and/or maintaining primate naïve pluripotent stem cells in culture.

This problem is solved by the features of the independent claims. Preferred embodiments of the present invention are provided by the dependent claims.

The invention therefore relates to the in vitro use of one or more type 7 long terminal repeat (LTR7) nucleic acid sequences of type H human endogenous retroviruses (HERVH) ("LTR7/HERVH nucleic acid sequences") for identifying and/or isolating primate naive pluripotent stem cells.

Preferred embodiments of the LTR7/HERVH nucleic acid sequences are disclosed herein as the sequences according to SEQ ID NO 1, 2 and/or 3.

It was unexpected at the time of developing the present invention that LTR7 sequence transcription may be utilized as a marker for naïve PSCs. The prior art in this field had suggested that maintained LTR sequence transcription in SCs lead to a differentiation defective phenotype (a loss of pluripotency; Ohnuki et al) or that cells without LTR7 expression showed maintained pluripotency (differentiation resistance; WO 2013/014929).

The invention therefore relates to a method for identifying and/or isolating primate naive pluripotent stem cells comprising an analysis (measurement, detection, identification and/or determination) of LTR7/HERVH-associated transcription.

In one embodiment the method of the invention and use of LTR7/HERVH sequences as described herein is characterised in that the method comprises analysis of LTR7/HERVH-associated transcription, wherein LTR7/HERVH-associated transcription is used as a positive marker for primate naive pluripotent stem cells.

Analysis of LTR7/HERVH-associated transcription may employ any appropriate technical means, such as a quantitative or semi-quantitative RNA method, in particular measuring the RNA produced from said transcription. This RNA may be assessed by PCR amplification of reverse transcribed DNA molecules corresponding to LTR7 transcripts. Appropriate primers may be selected by a skilled person using means known in the art. For example, RT-PCR may be employed, or sequencing-based methods may be applied that are capable of sequencing and/or quantifying reverse transcribed DNA corresponding to LTR7 transcripts.

In one embodiment the use of LTR7/HERVH sequences as described herein is characterised in that the LTR7/HERVH nucleic acid sequence comprises a LBP9 binding motif, preferably wherein the LTR7/HERVH nucleic acid sequence comprises a binding motif for one or more (preferably all) of the following transcription factors: LBP9, OCT4, NANOG and/or KLF4.

In another aspect the invention relates to an in vitro method for isolating primate naive pluripotent stem cells comprising an analysis of LTR7/HERVH-associated transcription and isolation of cells in which LTR7/HERVH-associated transcription is elevated in comparison to control cells, wherein control cells are preferably primed pluripotent stem cells or differentiated cells.

In another aspect the invention relates to an isolated population of primate naive pluripotent stem cells in which LTR7/HERVH-associated transcription is elevated in comparison to control cells, wherein control cells are preferably primed pluripotent stem cells or differentiated cells.

A description of primed cells is provided in[25] in addition to[2-4] and the cells used in the examples disclosed herein. Primed PSCs may be identified without difficulties by a person skilled in the art.

To the knowledge of the inventors, an isolated population of naïve stem cells has been neither described nor suggested in the art. The naïve PSCs that exhibit elevated LTR7 expression are naïve in the sense that they reflect very closely the expression profile of cells from the ICM and show no pre-disposition to differentiate in any particular differentiation fate.

According to the present invention the expression profile of cells may be used to identify "naivety" in a PSC. For example cells that resemble closely the inner cell mass (ICM) may be considered as a naïve or naïve-like PSC. To this end, the cells described herein, enriched using the HERVH reporter, are good representatives of naïve cells as they cluster nearer to cells of the ICM when compared with the 'novel naïve' cells obtained in reference 4 (FIG. 4e, refer also FIG. 20). The HERVH-driven transcriptional profiles in the current naïve-like hPSC lines (including the GFP(high) cells; also referred to interchangeably as GFP$^{high}$) are only slightly different from human ICM. The reporter construct described herein therefore represents a powerful tool for isolating naïve PSCs, culturing naïve PSCs and for enabling optimization of naïve-like hPSC culture conditions.

As used herein, the term naïve pluripotent stem cell relates preferably to the LTR7-expressing naïve pluripotent stem cell as described in detail herein. These cells may be referred as "naïve pluripotent stem cell" or "naïve-like PCSs" due to the closeness of their expression profiles to cells of the ICM, thereby indicating a "true" state or naivety.

The cells of the invention show unexpectedly good properties with respect to long culture times without priming towards a differentiation fate or the occurrence of differentiation. The cells may be maintained in culture and later differentiated to particular precursors, as is desired according to the intended therapy. The cells are also particularly suitable and robust when stored under cryopreservation or whilst being maintained in culture. The frequency of transposition in the isolated cell population of the invention is low compared to previously described "naïve SC populations" (compared for example to reference 27).

In another aspect the invention relates to a nucleic acid reporter construct comprising a nucleic acid sequence region encoding one or more marker or reporter molecules operably linked to a sequence comprising one or more LTR7/HERVH nucleic acid sequences.

A marker molecule relates preferably to a fluorescent protein, preferably green fluorescent protein or other proteins capable of being used as a reporter, and/or other selectable proteins, such as antibiotic resistance genes.

According to the present invention the term reporter construct relates to a nucleic acid molecule capable of selective identification of a particular cellular or sub-cellular state, preferably a reporter construct is capable of expression of a marker protein upon entering a particular state. For example, the reporter construct described herein is preferably defined by induced expression of a reporter (or marker protein, such as GFP) after LTR7 sequence expression as a marker for the naïve pluripotent stem cell state.

Fluorescent proteins are, without limitation, preferably selected from the group consisting of GFP (wt), Green Fluorescent Proteins, EGFP, Emerald, Superfolder GFP, Azami Green, mWasabi, TagGFP, TurboGFP, AcGFP, ZsGreen, T-Sapphire, Blue Fluorescent Proteins, EBFP, EBFP2, Azurite, mTagBFP, Cyan Fluorescent Proteins, ECFP, mECFP, Cerulean, mTurquoise, CyPet, AmCyan1, Midori-Ishi Cyan, TagCFP, mTFP1 (Teal), Yellow Fluorescent Proteins, EYFP, Topaz, Venus, mCitrine, YPet, TagYFP, PhiYFP, ZsYellow1, mBanana, Orange Fluorescent Proteins, Kusabira Orange, Kusabira Orange2, mOrange, mOrange2, dTomato, dTomato-Tandem, TagRFP, TagRFP-T, DsRed, DsRed2, DsRed-Express (T1), DsRed-Monomer, mTangerine, Red Fluorescent Proteins, mRuby, mApple, mStrawberry, AsRed2, mRFP1, JRed, mCherry, HcRed1, mRaspberry, dKeima-Tandem, HcRed-Tandem, mPlum and AQ143.

Suitable antibiotic resistance genes are, without limitation, preferably selected from the group consisting of Blasticidin, Zeocin, Puromycin, G418, Hygromycin B Gold and Phleomycin.

The reporter may therefore be introduced into stem cells or populations of stem cells in vitro, and subsequently used to identify and/or separate naïve stem cells based on activation of the reporter. Activation of the reporter may be detected via fluorescence microscopy, FACS, survival of cells after antibiotic treatment, or other suitable means.

In one embodiment the invention relates to an isolated cell comprising a reporter construct as described herein, wherein the reporter construct is preferably comprised by a nucleic acid vector, wherein the vector preferably comprises transposon sequences.

The invention also relates to the in vitro use of the reporter construct, nucleic acid vector and/or cell as described herein in a method for optimizing a cell growth medium for primate naive pluripotent stem cells.

As described in the examples in more detail, the invention enables the optimization of cell growth medium by monitoring the expression of the reporter of the invention whilst modifying cell culture conditions or medium components, in order to maintain a "read-out" on the naïve status of the cultured pluripotent stem cells.

In one embodiment the method for optimizing a cell growth medium as described herein comprises:

In vitro cultivation of primate naive pluripotent stem cells in a cell growth medium for primate naive pluripotent stem cells, wherein said cells comprise a reporter construct as described herein;

Modification of the presence and/or concentration of one or more components of said cell growth medium or other cell culture conditions; and analysis of expression of the reporter molecule encoded by said construct, preferably comprising a comparison in reporter molecule expression between the modified (according to step b.) and unmodified cell growth medium.

In another aspect the invention relates to a cell growth medium for cultivation of primate naive pluripotent stem cells produced by the optimization method described herein.

In another aspect the invention relates to a cell growth medium for cultivation of primate naive pluripotent stem cells. The medium may be optimized for enabling cultivation of said cells. The optimization involves the addition or modification of the concentration of various medium components.

The initial examples of the present invention employ human 2i/LIF medium, which is based on mouse 2i/LIF medium. The human medium contains, in one embodiment, by way of example, knockout DMEM, 20% knockout serum supplement, 1 mM L-Glutamine, 1% nonessential amino acids, 0.1 mM 2-mercaptoethanol, 10 ng/ml LIF, 1 µM CHIR99021, 1 µM PD0325901 and primocin, and the medium was supplemented with 10 ng/ml bFGF.

The contents of this medium may therefore be modified with respect to the presence and/or concentration of any one or more of its components as described above, or with respect to the following chemical inhibitors, or other medium components, such as cytokines, or other common components known to a skilled person, in order to assess whether any given change leads to an effect on expression of the LTR7/HERVH nucleic acid sequences as described herein.

In a preferred embodiment of the method for optimizing cell culture conditions, an improved cell culture medium or culture conditions has been identified when the expression of the reporter construct described herein is greater in the modified culture medium/condition in comparison to an unmodified cell growth medium/condition.

In a further embodiment of the invention the medium comprises a combination of basal medium, cytokines and small molecules, such as the inhibitors described herein, for example in the form of a cocktail of inhibitors.

In another aspect the invention relates to a kit for producing a cell growth medium for cultivation of primate naive pluripotent stem cells. The medium may be provided prior to its preparation a kit comprising components suitable for producing the medium upon their combination. For example, the kit of the invention may comprise the various components of the medium as described herein, either as single components or in pre-prepared mixtures. Pre-pared mixtures preferably relate to the basal medium, cytokines and a cocktail of multiple small molecules.

The invention therefore relates to a kit for the provision of a cell growth medium comprising the following components in separated compartments in proximity to one another: a basal medium, comprising neurobasal medium and DMEM, optionally comprising at least one or more cytokines of the IL-6 family, and a cocktail of inhibitors, comprising at least one or more MEK/ERK inhibitors, one or more a GSK3 inhibitors, one or more Axin stabilizers and one or more PKC inhibitors.

The invention further relates to the in vitro use of the cell growth medium as described herein for culturing, maintaining and/or enriching LTR7-expressing primate naive pluripotent stem cells, in which LTR7/HERVH-associated transcription is elevated in comparison to control cells, wherein control cells are preferably primed pluripotent stem cells or differentiated cells, from a stem cell population.

The invention further relates to a method for enriching LTR7-expressing primate naive pluripotent stem cells, in which LTR7/HERVH-associated transcription is elevated in comparison to control cells, wherein control cells are preferably primed pluripotent stem cells or differentiated cells, from a stem cell population by culturing a stem cell population in the cell growth medium as described herein.

Any disclosure provided herein directed to the kit, reporter, medium or any other aspect are to be understood in their context with each other. The features provided for one aspect of the invention may be used to define other aspects of the invention as required. In particular, the particular embodiments of inhibitors described herein are considered to be disclosed in any given combination of components and concentrations, as understood by a skilled person. The kit was developed specifically for the provision of the medium as described herein and the features disclosed in the context of the medium are correspondingly disclosed for the kit. The features as described in the context of the medium are also relevant for the methods and uses as described herein.

In one embodiment the basal medium comprises neurobasal medium. Neurobasal medium is known in the art and relates preferably to products that are commercially available, such as Neurobasal®-A Medium (Gibco/ThermoFisher), which is a basal medium formulated to meet the special cell culture requirements of post-natal and adult brain neuronal cells when used with GIBCO® B-27® Supplement. Neurobasal medium typically allows for both long and short term maintenance of homogeneous populations of neuronal cells without the need of an astrocyte feeder layer.

In one embodiment the basal medium comprises Dulbecco's Modified Eagle Medium (DMEM), which is a standard mammalian cell culture medium, or in DMEM/F12, which comprises DMEM with Nutrient Mixture F-12, as available from Gibco/ThermoFisher.

In further embodiments of the invention the basal medium of the cell culture medium of the invention comprises L-glutamine, Non-essential amino acids (NEAA), N2 supplement, B27 supplement without Vitamin A, and/or Vitamin C. The basal medium may optionally comprise insulin, 2-Mercaptoethanol and/or antibiotics.

In one embodiment the basal medium comprises a combination of commercially available components: Neurobasal medium, DMEM/F12, L-glutamine, NEAA, N2 supplement, B27 supplement (w/o Vitamin A), Vitamin C and 2-Mercaptoethanol. By way of example, the medium may be made to a 500 mL volume. In one embodiment the basal medium comprises 200-300 mL of neurobasal medium, preferably 220-270 mL. In one embodiment the basal medium comprises 200-300 mL of DMEM or DMEM/F12, preferably 220-270 mL. In one embodiment the basal medium comprises between 1 mL and 10 mL of a 100× stock of L-glutamine. In one embodiment the basal medium comprises between 1 mL and 10 mL of a 100× stock of NEAA. In one embodiment the basal medium comprises between 1 mL and 10 mL of a 100× stock of N2 supplement. In one embodiment the basal medium comprises between 2 mL and 20 mL of a 50× stock of B27 supplement, preferably without Vitamin A. In one embodiment the basal medium comprises between 10 and 500 mg/mL of Vitamin C, preferably 50-100 mg/mL.

In one embodiment the basal medium comprises between 0 and 100 ug/mL of insulin, preferably 20-50 mg/mL. In one embodiment the basal medium comprises between 0 and 1 mM, preferably 0.01 to 0.5 mM of 2-Mercaptoethanol. Other agents that reduce disulfide bonds may be used at an appropriate concentration.

In one embodiment the cytokines of the medium comprise one or more cytokines of the IL-6 family. Cytokines of the IL-6 family are known as IL-6, IL-11, oncostatin M (OSM) and LIF. Cytokines of the IL-6 family may be provided at a concentration of 1 to 1000 ng/mL, preferably 10 100 ng/mL.

In one embodiment the cytokines of the medium comprise human IL6 at 1 to 100 ng/mL, preferably 10 to 50 ng/mL.

In one embodiment the cytokines of the medium comprise human sIL-6R (soluble IL-6 receptor), at 1 to 100 ng/mL, preferably 10 to 50 ng/mL.

In one embodiment the cytokines of the medium comprise human LIF at 1 to 100 ng/mL, preferably 10 to 50 ng/mL.

In one embodiment the cytokines of the medium comprise optionally human Activin A at 0 or 1 to 100 ng/mL, preferably 10 to 50 ng/mL.

In one embodiment the cytokines of the medium comprise optionally human IL-11 at 0 or 1 to 100 ng/mL, preferably 10 to 50 ng/mL.

In one embodiment the cytokines of the medium comprise optionally human bFGF at 0 or 1 to 100 ng/mL, preferably 5 to 50 ng/mL.

In one embodiment the medium (or cocktail of inhibitors of the kit) comprises small molecules that comprise a MEK/ERK inhibitor, a B-raf inhibitor, a JNK inhibitor, a GSK3 inhibitor, a Axin stabilizer, a PKC inhibitor, a Notch inhibitor, a Sonic Hedgehog inhibitor, a BMP inhibitor, a TGFbeta inhibitor, a mitochondrial pyruvate dehydrogenase kinase inhibitor, a histone methyltransferase inhibitor, and/or a histone deacetylase inhibitor.

In one embodiment the medium (or corresponding cocktail of inhibitors of the kit) comprises a MEK/ERK inhibitor PD0325901, preferably 0.01-10 µM, more preferably 0.2-1 µM.

In one embodiment the medium (or cocktail of inhibitors) comprises a B-raf inhibitor SB590885: preferably 0.01-5 µM, more preferably 0.1-0.5 µM.

In one embodiment the medium (or cocktail of inhibitors) comprises a JNK inhibitor TCS-JNK-6o: preferably 0.05-50 µM, more preferably 0.2-10, or 0.5-5 µM.

In one embodiment the medium (or cocktail of inhibitors) comprises a GSK3 inhibitor BIO: preferably 0.01-5 µM, more preferably 0.05-0.5 µM; or CHIR99021: preferably 0.01-10 µM, more preferably 0.1-1 uM.

In one embodiment the medium (or cocktail of inhibitors) comprises an Axin stabilizer XAV939: preferably 0.1-50 µM, more preferably 1-10, or 2-5 µM; or endo-IWR1: preferably 0.1-50 µM, more preferably 1-5 µM.

In one embodiment the medium (or cocktail of inhibitors) comprises a PKC inhibitor Go6983: preferably 0.01-50 µM, more preferably 1-5, or 2-4 µM.

In one embodiment the medium (or cocktail of inhibitors) comprises a Notch inhibitor DAPT: preferably 0.1-100, more preferably 1-50, or 2-10 µM.

In one embodiment the medium (or cocktail of inhibitors) comprises a Sonic Hedgehog inhibitor HPI1: preferably 0.1-50, more preferably 1-5 µM.

In one embodiment the medium (or cocktail of inhibitors) comprises a BMP inhibitor K02288: preferably 0.1-50, more preferably 1-5 µM.

In one embodiment the medium (or cocktail of inhibitors) comprises a TGFbeta inhibitor A83-01: preferably 0.01-10, more preferably 0.1-1.0, or 0.2-0.5 µM.

In one embodiment the medium (or cocktail of inhibitors) comprises a mitochondrial pyruvate dehydrogenase kinase inhibitor DCA: preferably 0.1-100, more preferably 2-10 µM.

In one embodiment the medium (or cocktail of inhibitors) comprises a histone methyltransferase inhibitor DZNep: preferably 0.001-10, more preferably 0.005-1, or 0.01-0.1 µM.

In one embodiment the medium (or cocktail of inhibitors) comprises a histone deacetylase inhibitor Sodium butyrate: preferably 0.01-10, more preferably 0.1-0.5 mM; or SAHA: preferably 0.001-0.5, more preferably 0.01-0.05 µM.

In one embodiment the medium (or cocktail of inhibitors) comprises at least one or more MEK/ERK inhibitors, one or more a GSK3 inhibitors, one or more Axin stabilizers and one or more PKC inhibitors, preferably of those mentioned above in the concentrations mentioned above. The use of the basal medium, cytokines and small molecules of these classes (MEK/ERK inhibitors, GSK3 inhibitors, Axin stabilizers and PKC inhibitors) leads to a "4i" medium. The 4i medium is characterized by the ability to maintain naïve PSCs for long periods in culture without the need for re-sorting (such as using FACS) and also provides cells with increased genome stability, for example the Line1, SVA and other transposable elements show reduced mobility (reduced retrotransposition) in the genomes of naïve PSCs cultures after culturing in this medium.

Surprisingly, the invention provides an "exno-free" and feeder-free medium suitable for long-term culturing, maintenance and/or enrichment of naïve PSCs. Until the present time feeder cells were required when culturing naïve PSCs, leading to enhanced complication, cost and risk of contamination during culturing, which represents a significant disadvantage especially with respect to culturing the cells for later therapeutic use.

The medium as described herein is free of, or substantially free of, animal-derived components, thereby also reducing the disadvantages of most commonly used systems. Stem cell culture systems that rely on undefined animal-derived components introduce variability to the cultures and complicate their therapeutic use.

One aspect of the invention relates to a method for enriching LTR7-expressing primate naive pluripotent stem cells from a stem cell population by culturing a stem cell population in the cell growth medium as described herein. In particular, the medium described herein is capable of providing enrichment of LTR7-expressing naïve PSCs in culture. The medium is therefore defined by a set of features, namely LTR7-expression in naïve PSCs, that represent a common and unexpected concept linking all aspects of the present invention.

The invention therefore relates to the use of the medium described herein for the culturing of LTR7-expressing naïve PSCs. In one embodiment the oxygen content during cell culture can be reduced to approx. 5% oxygen (+/−3%), in order to additionally maintain the naïve state of the LTR-7-expressing naïve PSCs. Oxygen conditions during culture are therefore at approx. 20% (+/−5%), below 20%, below 15%, below 10%, such as between 2 and 8%, such as 5% oxygen.

The naive cells described herein are particularly useful for the provision of therapeutic material in the future by initiating differentiation programs as desired, in order to create cell therapy products, without have to use cells primed towards certain fates.

In one embodiment the medium (or cocktail of inhibitors) comprises, in addition to the one or more MEK/ERK inhibitors, one or more a GSK3 inhibitors, one or more Axin1 stabilizers and one or more PKC inhibitors, additionally one or more B-raf inhibitors, Notch inhibitors, Sonic Hedgehog inhibitors, JNK inhibitors, and one or more BMP inhibitors, preferably at the concentrations and specific examples provided above.

In one embodiment the medium (or cocktail of inhibitors) comprises at least one or more GSK3 inhibitors and one or more Axin stabilizers. The combination of these two classes of molecules provides unexpected results that are advantageous for the culturing of the LTR7-expressin naïve cells of the present invention.

The GSK3 inhibitor, such as BIO, leads to an activation of Wnt-signalling, whereas the Axin-1-stabilisor, such as XAV939, leads to an inhibition of Wnt-Signalling. Wnt-signalling is well-known to a skilled person and requires no detailed explanation in this context. The Wnt signaling pathway encompasses a group of signal transduction pathways that pass signals from outside of a cell through cell surface receptors inside the cell. Wnt-signalling is highly evolutionarily conserved in animals.

Through the combination of one or more GSK3 inhibitors and one or more Axin-1-stabilisors Wnt-signalling is repressed, but a low level of Wnt-singalling is maintained. This balanced activity leads to beneficial and surprising results. In particular, the combination of these two components, preferably with one or more MEK/ERK inhibitors and PKC inhibitors, provides long term maintenance of naïve PSCs in culture, up to for example 60 passages, without the need for re-sorting the cells according to expression of the LTR7 expression. This combination of factors leads to an enrichment during in vitro cell culture of naïve PSCs without any other sorting (such as FACS) steps. This combination of factors, i. e. the maintenance of a low level of Wnt-signalling, leads to maintenance and/or re-programming of PSCs into the naïve PSCs as defined by increased LTR7 expression compared to primed PSCs. Naïve PSCs may therefore be cultured in the medium described herein without the presence of the LTR7-reporter construct described herein. Independent of the use of the LTR7 reporter, the LTR7 transcription will be enhanced in the cell population cultured in the medium of the invention.

Information on the involved signals is provided in FIGS. 17-19.

One of the proposed mechanisms for the importance of Wnt-signaling is the proportion of Beta-Catenin that is free to act as a transcriptional regulator and the amount that functions in the cytosol but at the membrane in E-Cadherin complexes, which are important in cell-cell contact. This mechanism suggest that Wnt-signalling may be reduced, but not removed entirely, partially perhaps due to the requirement of the E-Cadherin function in forming cell colonies in culture. Some cytosolic fraction of B-catenin should be maintained in order to keep these functions in order.

In a preferred embodiment the Wnt-Signalling is modulated to correspond to an activity defined by administration of a GSK3 inhibitor, such as BIO, and an Axin-1-stabilisor, such as XAV939, at a ratio of 1:1000 to 1:1, preferably 1:200 to 1:10, more preferably 1:150 to 1:50.

In further embodiments, one or more of the following inhibitors may be added to the medium or the inhibitor cocktail as described herein, and the concentration thereof preferably modified in order to assess whether expression of the LTR7/HERVH nucleic acid sequences, as a marker for the primate naive pluripotent stem cells, is affected:

Mitogen-activated protein kinase kinase (MAP2K, MEK, MAPKK) inhibitor, WNT signalling activator, mitogen-activated protein (MAP) Kinase Inhibitor, c-Jun N-terminal kinases (JNK) inhibitor, Protein kinase C (PKC) inhibitor, Rho-associated, coiled-coil containing protein kinase (ROCK) inhibitor, Glycogen synthase kinase 3 (GSK-3) inhibitor, Bone morphogenetic protein (BMP) signalling inhibitor, histone deacetylase (HDAC) inhibitor, B-Raf kinase inhibitor, Lck/Src inhibitor, RasGAP inhibitor, ERK1 or ERK2 (extracellular-signal-regulated kinases (ERK) 1/2) inhibitor, histone-lysine methyltransferase (HMTase) inhibitor and/or DNA methyltransferase inhibitor.

MEK/ERK inhibitors include but are not limited to PD98059 (Pfizer), U0126 (DuPont), PD184352 [CI-1040] (Pfizer), PD0325901 (Pfizer), Selumetinib (a.k.a., ARRY-142886, AZD6244) (Astra-Zeneca), GDC-0994 and RDEA119 (Ardea Biosciences) and PD0325901.

GSK3 inhibitors include but are not limited to Valproic acid sodium salt, Staurosporine, KT 5720, GSK-3 Inhibitor IX, Ro 31-8220, SB-216763, CID 755673, Kenpaullone, Lithium Chloride, GSK-3β Inhibitor XII, TWS119, GSK-3 Inhibitor XVI, 10Z-Hymenialdisine, Indirubin, CHIR-98014, GSK-3β Inhibitor VI, Manzamine A, Indirubin-3'-monoxime, GSK-3 Inhibitor X, GSK-3 Inhibitor XV, SB-415286, 1-Azakenpaullone, TWS 119 ditrifluoroacetate, 5-Iodo-indirubin-3'-monoxime, GSK-3β Inhibitor I, 9-Cyanopaullone, 5-Iodo-Indirubin-3'-monoxime, Indirubin-5-sulfonic acid sodium salt, GSK-3β Inhibitor VII, Cdk1/5 Inhibitor, Bisindolylmaleimide X hydrochloride, Isogranulatimide, Raf Kinase Inhibitor IV, L-779,450, Indirubin-3'-monoxime-5-sulphonic Acid, GSK-3 Inhibitor II, GSK-3β Inhibitor VIII, Aloisine A, GSK-3β Inhibitor XI, GSK-3 Inhibitor IX, Control, MeBIO, Alsterpaullone, 2-Cyanoethyl, TCS 2002, TCS 21311, Enzastaurin, MeBIO, Cdk2/9 Inhibitor, Cdk1/2 Inhibitor III, PHA 767491 hydrochloride, AR-AO 14418-d3, Hymenialdisine Analogue 1 and BIO.

Axin stabilizers include but are not limited to IWR-1-endo, IWR-1-exo and XAV939.

PKC inhibitors include but are not limited to Calphostin C, CGP 53353, Chelerythrine chloride, Dihydrosphingosine, GF 109203X, Go 6976, Go 6983, K-252c, LY 333531 hydrochloride, [Ala107]-MBP (104-118), [Ala113]-MBP (104-118), Melittin, (±)-Palmitoylcarnitine chloride, PKC (19-36), [Glu27]-PKC (19-36), Inactive control peptide for PKC (19-36), PKC 412, PKC β pseudosubstrate, PKC ζ pseudosubstrate, Ro 32-0432 hydrochloride, Rottlerin, D-erythro-Sphingosine (synthetic), Go6983 and TCS 21311.

B-raf inhibitors include but are not limited to Vemurafenib (PLX4032, RG7204), Sorafenib Tosylate, PLX-4720, Dabrafenib (GSK2118436), GDC-0879, LY3009120, RAF265 (CHIR-265), AZ 628, NVP-BHG712 and SB590885.

Notch inhibitors include but are not limited to FLI-06, RO4929097, Semagacestat (LY450139), LY411575, YO-01027 (Dibenzazepine), DAPT and Avagacestat (BMS-708163).

Sonic Hedgehog inhibitors include but are not limited to GANT61, Vismodegib (GDC-0449), Taladegib (LY2940680), TAI-1, HPI1 and Pimasertib (AS-703026).

JNK inhibitors include but are not limited to AEG 3482, Anisomycin, BI 78D3, CEP 1347, c-JUN peptide, IQ 3, JIP-1 (153-163), SR 3576, SU 3327, TCS-JNK-6o and TCS JNK 5a.

BMP inhibitors include but are not limited to Dorsomorphin dihydrochloride, K 02288, ML 347, NBMPR and UK 383367.

The medium of the present invention may therefore comprise one or more of the above mentioned inhibitors. All possible combinations of each of the various inhibitors or classes of inhibitors disclosed herein are considered for use in the medium of the present invention.

As examples of such inhibitors, one or more of the following components, which are not limiting to the inhibitor classes mentioned above, may be utilized during optimization (presence and/or concentration varied during testing), and/or may be present in the medium of the present invention:

PD0325901, at preferred concentration of 0.01 to 100 µM, more preferred 0.1 to 10 µM, such as 1 or 0.5 µM. PD0325901 is an orally bioavailable, synthetic organic molecule targeting mitogen-activated protein kinase kinase (MAPK/ERK kinase or MEK) with potential antineoplastic activity. MEK inhibitor PD325901 is a derivative of MEK inhibitor CI-1040, selectively binds to and inhibits MEK, which may result in the inhibition of the phosphorylation and activation of MAPK/ERK and the inhibition of tumor cell proliferation. The dual specific threonine/tyrosine kinase MEK is a key component of the RAS/RAF/MEK/ERK signaling pathway that is frequently activated in human tumors.

CHIR99021, at preferred concentration of 0.01 to 300 µM, more preferred 0.1 to 30 µM, most preferred 1-3 µM. CHIR99021 is an aminopyrimidine derivative that is an extremely potent inhibitor of GSK3, inhibiting GSK3β (IC50=6.7 nM) and GSK3α (IC50=10 nM) and functions as a WNT activator. It is the most selective inhibitor of GSK3 reported so far. Used in cardiomyocyte differentiation from human embryonic stem (ES) and induced pluripotent stem (iPS) cells. CHIR99021 maintains undifferentiated mouse ES cells in combination with PD0325901, in the absence of LIF. CHIR99021 maintains human and mouse hematopoietic stem cells in cytokine-free conditions, in combination with rapamycin. CHIR99021 enables chemical reprogramming (without genetic factors) of mouse embryonic fibroblasts to iPS cells, in combination with Forskolin, Tranylcypromine, Valproic Acid, 3-Deazaneplanocin A, and E-616452. Generates mouse-like or "ground state" iPS cells from human and rat somatic cells, in combination with PD0325901 and A83-01.

SP600125, at preferred concentration of 0.01 to 1000 µM, more preferred 0.1 to 100 µM, most preferred 10 µM. SP600125 is a potent, cell-permeable, selective and reversible inhibitor of c-Jun N-terminal kinase (JNK). It inhibits in a dose-dependent manner the phosphorylation of JNK. JNK is a member of the mitogen-activated protein kinase (MAPK) family and plays an essential role in TLR mediated inflammatory responses. Inhibition of JNK activity by SP600125 is usually associated with downregulation of Beclin-1 and reduced autophagy.

SB 202190, at preferred concentration of 0.01 to 1000 µM, more preferred 0.1 to 50 µM, most preferred 5 µM. SB 202190 is a potent, reversible, competitive, and cell-permeable inhibitor of p38 MAP kinase.

Go6983, at preferred concentration of 0.01 to 1000 µM, more preferred 0.1 to 50 µM, most preferred 1 to 10 µM, or 5 µM. Go6983 is a PKC inhibitor and has been shown to selectively inhibit several PKC isoenzymes (IC50=7 nM for PKCα and PKCβ; 6 nM for PKCγ; 10 nM for PKCδ; 60 nM for PKCζ). The compound does not effectively inhibit PKCµ (IC50=20 µM) and therefore can be used to differentiate PKCµ from other isoforms.

ROCK inhibitor Y-27632, at preferred concentration of 0.01 to 1000 µM, more preferred 0.1 to 100 µM, most preferred 10 µM. Y-27632 is a cell-permeable, highly potent and selective inhibitor of Rho-associated, coiled-coil containing protein kinase (ROCK). Y-27632 inhibits both ROCKI (Ki=220 nM) and ROCKII (Ki=300 nM) by competing with ATP for binding to the catalytic site. It enhances survival of human embryonic stem (ES) cells when they are dissociated to single cells by preventing dissociation-induced apoptosis (anoikis), thus increasing their cloning efficiency. Improves embryoid body formation using forced-aggregation protocols. Increases the survival of cryopreserved single human ES cells after thawing.

BIO, at preferred concentration of 0.001 to 1000 µM, more preferred 0.05 to 0.1 µM, most preferred 2 µM. 6-bromoindirubin-3-oxime (BIO) is a potent, reversible and ATP-competitive GSK-3α/β inhibitor and the first pharmacological agent shown to maintain self-renewal in human and mouse embryonic stem cells. Human embryonic stem cells (hESCs) are maintained in the undifferentiated state through treatment with a GSK-3 inhibitor, BIO, under a feeder-free condition.

Dorsomorphin, at preferred concentration of 0.01 to 1000 µM, more preferred 0.1 to 100 µM, most preferred 2 µM. Dorsomorphin is a selective inhibitor of Bone morphogenetic protein (BMP) signaling. It has been found to inhibit BMP signals required for embryogenesis and promoted significant neural differentiation from human pluripotent stem cell (hPSC) lines. Dorsomorphin also acts as a potent, selective, reversible, and ATP-competitive inhibitor of AMPK (AMP-activated protein kinase); Ki=109 nM in the presence of 5 µM ATP and the absence of AMP).

Sodium butyrate, at preferred concentration of 0.01 to 100 mM, more preferred 0.1 to 10 mM, most preferred 0.1 mM. Sodium butyrate is a compound with formula Na(C3H7COO). It is the sodium salt of butyric acid. It has various effects on cultured mammalian cells including inhibition of proliferation, induction of differentiation and induction or repression of gene expression. As such, it can be used in lab to bring about any of these effects. Specifically, butyrate treatment of cells results in histone hyperacetylation, and butyrate itself inhibits HDAC activity. Butyrate has been an essential vehicle for determining the role of histone acetylation in chromatin structure and function. Inhibition of HDAC activity is estimated to affect the expression of only 2% of mammalian genes.

SAHA, at preferred concentration of 0.01 to 1000 nM, more preferred 0.1 to 100 nM, most preferred 50 nM. SAHA or Vorinostat facilitates the transcription of genes that result in apoptosis, differentiation and growth arrest. It has been observed to give beneficial results in lymphoma but not in solid tumors. Vorinostat or suberoylanilide hydroxamic acid (SAHA) is a potent, reversible pan-histone deacetylase (HDAC) inhibitor. It inhibits both class I and class II HDACs, altering gene transcription and inducing cell cycle arrest and/or apoptosis in a wide variety of transformed cells.

SB590885, at preferred concentration of 0.01 to 100 µM, more preferred 0.1 to 10 µM, most preferred 0.5 µM. SB-590885 is a potent and selective ATP competitive inhibitor of B-Raf kinase with Kd=300 pM for B-Raf, and >1000-fold selectivity over a panel of 22 commonly studied cellular kinases WH-4-023, at preferred concentration of 0.01 to 1000 µM, more preferred 0.1 to 100 µM, most preferred 1 µM. WH-4-023 is a potent and selective dual Lck/Src inhibitor with IC50 of 2 nM/6 nM for Lck and Src kinase respectively; shows little inhibition on p38α and KDR.

IM-12, at preferred concentration of 0.01 to 1000 µM, more preferred 0.1 to 100 µM, most preferred 1 µM. IM-12 is a selective GSK-3β inhibitor with IC50 of 53 nM, and also enhances canonical Wnt signalling.

Pluripotin, at preferred concentration of 0.01 to 1000 µM, more preferred 0.1 to 100 µM, most preferred 2 µM. Pluripotin is an activator of murine embryonic stem (ES) cell self-renewal. It appears that pluripotin mediates the activity by dual RasGAP and ERK1 inhibition.

FR 180204, at preferred concentration of 0.01 to 1000 µM, more preferred 0.1 to 100 µM, most preferred 1 to 10 µM. FR180204 is a potent, cell-permeable, ATP-competitive inhibitor of ERK1 and ERK2 (mitogen-activated protein kinase (MAPK)/extracellular-signal-regulated kinases (ERK) 1/2).

BIX 01294, at preferred concentration of 0.01 to 1000 µM, more preferred 0.1 to 100 µM, most preferred 1 to 10 µM. BIX-01294, a diazepin-quinazolinamine derivative, is a histone-lysine methyltransferase (HMTase) inhibitor that modulates the epigenetic status of chromatin. BIX-01294 inhibits the G9aHMTase dependent levels of histone-3 lysine (9) methylation (H3K9me). Bix-01294 and valproic acid, a histone deacetylase (HDAC) inhibitor, may replace the requirement for ectopic OCT4 (POU5F1) and cMyc respectively in pluripotent stem cell induction (iPS) recipes. BIX 01294 is a selective histone methyl transferase inhibitor. In its inhibition of the histone lysine methyltransferases, BIX 01294 does not compete with cofactor S-adenosylmethionine. The target enzyme is G9a, and it selectively impairs G9a HMTase and the generation of H3K9me2 in vitro.

Decitabine, at preferred concentration of 0.01 to 1000 µM, more preferred 0.1 to 100 µM, most preferred 0.5 to 10 µM. Decitabine (trade name Dacogen), or 5-aza-2'-deoxycytidine, is a drug for the treatment of myelodysplastic syndromes, a class of conditions where certain blood cells are dysfunctional, and for acute myeloid leukemia (AML). Chemically, it is a cytidine analog. Decitabine is a hypomethylating agent. It hypomethylates DNA by inhibiting DNA methyltransferase. It functions in a similar manner to azacitidine, although decitabine can only be incorporated into DNA strands while azacitidine can be incorporated into both DNA and RNA chains.

Chaetocin, at preferred concentration of 0.01 to 1000 µM, more preferred 0.1 to 100 µM, most preferred 1 to 10 µM. Chaetocin is a fungal metabolite with antimicrobial and cytostatic activity. It belongs to the 3,6-epidithio-diketopiperazines class of which gliotoxin, sporidesmin, aranotin, oryzachloride, verticillin A and the melinacidins are members.1,3 Chaetocin is a molecular dimer of two five-membered rings cis fused. Interestingly, the chirality of the 3,6-epidithio-diketopiperazine moiety in chaetocin is opposite to the chirality in gliotoxin, sporidesmin, aranotin and oryzachloride and while the later compounds show antiviral activity, chaetocin does not. This fungal toxin showed strong cytotoxicity against HeLa cells (IC50=0.05 µg/ml). Chaetocin was found to be a specific inhibitor of the lysine-specific histone methyltransferase SU(VAR)3-9 (IC50=0.6 µM) of *Drosophila melanogaster* and of its human ortholog (IC50=0.8 µM), and acts as a competitive inhibitor for S-adenosylmethionine.

XAV939 at a preferred concentration of 0.1 µM to 100 µM, preferably 1 to 10 µM. XAV939 antagonizes Wnt signaling via stimulation of β-catenin degradation and stabilization of axin. Inhibits proliferation of the β-catenin-dependent colon carcinoma cell line DLD-1. It promotes cardiomyogenic development in mesoderm progenitor cells.

DAPT at a preferred concentration of 0.11 to 100 µM, preferably 1 to 50, more preferably 2 to 10 µM. DAPT is a γ-secretase inhibitor and indirectly an inhibitor of Notch, a γ-secretase substrate. DAPT has been shown to inhibit Notch signaling in studies of autoimmune and lymphoproliferative diseases, such as ALPS and lupus erythematosus (SLE), as well as in cancer cell growth.

HPI1 at a preferred concentration of 0.01 to 500 µM, preferably 0.1 to 50 µM, more preferably 1 to 5 µM. HPI1 relates to Hedgehog (Hh) signaling inhibitor. Inhibits Sonic hedgehog (Shh)-, SAG- and Gli-induced Hh pathway activation in Shh-LIGHT2 cells. It does not inhibit Wnt signaling.

TCS-JNK-60 at a preferred concentration of 0.01 to 500 µM, preferably 0.1 to 50 µM, more preferably 0.5 to 5 µM. TCS-JNK-60 is an ATP-competitive c-Jun N-terminal kinase (JNK) inhibitor. It inhibits c-Jun phosphorylation and prevents collagen-induced platelet aggregation in vitro.

K02288 at a preferred concentration of 0.01 to 500 µM, preferably 0.1 to 50 µM, more preferably 0.5 to 5 µM. K02288 is a potent and selective inhibitor of type I bone morphogenic protein (BMP) receptors.

TABLE 1

Summary of potential inhibitors for the medium of the invention:

| Inhibitor | Source | Cat. No. | W.M. | Amount (mg) | Volume (µl) | Solvent | Stock Con. | Preferred Final. Con. |
|---|---|---|---|---|---|---|---|---|
| PD0325901 | Axon Medchem | Axon 1408 | 482.19 | 5 | 1036.9 | DMSO | 10 mM | 1 µM |
| CHIR99021 | Axon Medchem | 1386 | 465.35 | 2 | 1432.6 | DMSO | 3 mM | 1-3 µM |
| SP600125 | Tocris | 1496 | 220.23 | 10 | 908.1 | DMSO | 50 mM | 10 µM |
| SB 202190 | Axon Medchem | Axon 1364 | 331.35 | 10 | 1207.2 | DMSO | 25 mM | 5 µM |
| Go6983 | Tocris | 2285 | 447.01 | 10 | 1656.7 | DMSO | 10 mM | 5 µM |
| ROCKI | Millipore | 688000 | 338.3 | 10 | 2956 | $H_2O$ | 10 mM | 10 µM |

TABLE 1-continued

Summary of potential inhibitors for the medium of the invention:

| Inhibitor | Source | Cat. No. | W.M. | Amount (mg) | Volume (µl) | Solvent | Stock Con. | Preferred Final. Con. |
|---|---|---|---|---|---|---|---|---|
| BIO | Sigma | B1686-5MG | 356.17 | 5 | 1403.8 | DMSO | 10 mM | 2 µM |
| Dorsomorphin | Sigma | P5499-5MG | 399.49 | 5 | 1251.6 | DMSO | 10 mM | 2 µM |
| K02288 | BMP | Tocris | 4986 | 352.38 | 10 mg | DMSO | 10 mM | 2 µM |
| Sodium butyrate | Sigma | B5887 | 110.1 | 250 | 2270.7 | H$_2$O | 1000 mM | 0.1 mM |
| SAHA | Cayman | 10009929 | 264.3 | 1000 | 15000 | DMSO | 250 mM | 50 nM |
| SB590885 | Tocris | 2650 | 453.54 | 10 | 4410 | DMSO | 5 mM | 0.5 µM |
| WH-4-023 | A Chemtek, | H620061 | 568.67 | 10 | 1758 | DMSO | 10 mM | 1 µM |
| IM-12 | Enzo | BML-WN102-0005 | 377.4 | 5 | 1324 | DMSO | 10 mM | 1 µM |
| Pluripotin | Toris | 4433 | 550.54 | 5 | 908 | DMSO | 10 mM | 2 µM |
| FR 180204 | Toris | 3706 | 327.34 | 5 | 1527 | DMSO | 10 mM | 1-10 µM |
| GDC-0994 | Selleckechem | S7554 | 439.85 | 5 mg | 1137 µl | DMSO | 10 mM | 2 µM |
| SCH772984 | Selleckechem | S7101 | 587.67 | 5 mg | 851 µl | DMSO | 10 mM | 0.5-1 µM |
| BIX 01294 | Toris | 3364 | 600.02 | 5 | 833 | DMSO | 10 mM | 1-10 µM |
| Decitabine | Toris | 2624 | 228.21 | 5 | 2191 | DMSO | 10 mM | 0.5-10 µM |
| Chaetocin | Toris | 4504 | 696.84 | 5 | 718 | DMSO | 10 mM | 1-10 µM |

Furthermore, the medium of the invention may comprise one or more cytokines. The cytokines may be adjusted or optimized according to expression of the LTR7/HERVH nucleic acid sequences as described herein.

TABLE 2

Summary of potential cytokines for the medium of the invention:

| Cytokines | Brand/company | Cat. No. | Final. Con. |
|---|---|---|---|
| LIF | Millipore | LIF1010 | 10 ng/µl |
| bFGF | PeproTech | AF-100-18B | 10 ng/µl |
| IL11 | PeproTech | 200-11 | 10 ng/µl |
| sIL6R | PeproTech |  | 20 ng/µl |
| IL6 | PeproTech | AF-200-06 | 20 ng/µl |

The preferred LTR7/HERVH sequences used in the present invention are the following:

Reporter sequences:

1) LTR7_long version (human; corresponds to
LTR7#2; SEQ ID NO 1):
ATGCTGCGAGATGGGAAACACATACAAAATCTTCAACCTTCAGTAAGTAA
AAACCTTCTCTATTAAAATCTGCAAAGTGTATTCATTTGTTCTAAAATTA
TTTGCTAAGTGCCCACACAGCACTAGGAATGAAACATAAAAAAATCTCTT
CCCTCACTTAGCTTCGTATTCTCTTTGGGAATGTCAGGCCTCTGAGCCCA
AGCCAAGCCATCGCATCCCTATGACATGCACGTACACGCCCAGATGGCC
TGAAGTAACTGAAGAATCACAAAAGAAGTGAATATGCCCTGCCCCACCTT
AACTGATGACATTCCACCACAAAAGAAGTGTAAATGGCCAGTCCTTGCCT
TAACTGATGACATTACCTTGTGAAAGTCCTTTTCCTGGCTCATCCTGGCT
CAAAAAGCACCCCCACTGAGCACCTTGCGACCCCCCGCTCCTACCCGCCA
GAGAACAAACCCCCTTTGACTGTAATTTTCCTTTACCTAACCAAATCCTA
TAAAACGGCCCCACCCTTATCTCCCTTCGCTGACTCTCTTTTCGGACTCA
GCCCGCCTGCACCCAGGTGAAATAAACAGCCTCGTTGCTCACACAAAGCC
TGTTTGGTGGTCTCTTCACACGGACGCGCATGAAATTTGGTGCCGTGACT
CGGATCGGGGGACCTCCCTTGGGAGATCAATCCCCTGTCCTCCTGCTCTT
TGCTCCGTGAGAAAGATCCACCTACGACCTCAGGTCCTCAGACCAACCAG
CCCAAGAAACATCTCACCAATTTCAAATCCGGTAAGCGGCCTCTTTTTAC
TCTGTTCTCCAACCTCCCTCACTATCCCTCAACCTCTTTCTCCTTTCAAT
CTTGGCGCCACACTTCAATCTCTCCCTTCTCTTAATTTCAATTCCTTTCA
TTCTCTGGTAGAGACAAAAGAGACATGTTTTATCCGTGAACCCAAAACTC
CGGCGCCGGTCACGGACTGGGAAGGCAGTCTTCCCTTGGTGTTTAATCAT
TGCAGGGACGCCTCTCTGATTTCACGTTTCAGACCACGCAGGGATGCCTG
CCTTGGTCCTTCACCCTTAGCGGCAAGTCCCGCTTTCCTGGGGCAGGGGC
AAGTACCCCTCAACCCCTTCTCCTTCACCCTTAGCGGCAAGTCCCGCTTT
TCTGGGGCAGGGGCAAGTACCCCTCA
ACCCCTTCTCCTTCACCC 2) LTR7_short version (human; corresponds to
LTR7#1; SEQ ID NO 2):
TGCTAAGTGCCCACACAGCACTAGGAATGAAACATAAAAAAATCTCTTCC
CTCACTTAGCTTCGTATTCTCTTTGGGAATGTCAGGCCTCTGAGCCCAAG
CCAAGCCATCGCATCCCTATGACATGCACGTACACGCCCAGATGGCCTG
AAGTAACTGAAGAATCACAAAAGAAGTGAATATGCCCTGCCCCACCTTAA
CTGATGACATTCCACCACAAAAGAAGTGTAAATGGCCAGTCCTTGCCTTA
ACTGATGACATTACCTTGTGAAAGTCCTTTTCCTGGCTCATCCTGGCTCA
AAAAGCACCCCCACTGAGCACCTTGCGACCCCCCGCTCCTACCCGCCAGA
GAACAAACCCCCTTTGACTGTAATTTTCCTTTACCTAACCAAATCCTATA
AAACGGCCCCACCCTTATCTCCCTTCGCTGACTCTCTTTTCGGACTCAGC
CCGCCTGCACCCAGGTGAAATAAACAGCCTCGTTGCTCACACAAAGCCTG
TTTGGTGGTCTCTTCACACGGACGCGCATGAAATTTGGTGCCGTGACTCG
GATCGGGGGACCTCCC 3) LTR7Y: (human; corresponds to a variant of
LTR7. Preliminary data suggest that in addition to
constructs #1 and #2 it would be useful to
optimize culture conditions; SEQ ID NO 3):
TGTCAGGCCTCTGAGCCCAGGCCAGGCCATCGCATCCCCTGTGACTTGCA
CGTATACATCCAGATGGCCTGAAGTAACTGAAGATCCACAAAAGAAGTAA
AAACAGCCTTAACTGATGACATTCCACCATTGTGATTTGTTCCTGCCCCA
CCCTAACTGATCAATGTACTTTGCAATCTCCCCCACCCTTAAGAAGGTTC
TTTGTAATTCTCCCCACCCTTGAGAATGTACTTTGTGAGATCCACCCCTG
CCCACCAGAGAACAACCCCCTTTGACTGTAATTTTCCATTACCTTCCCAA
ATCCTATAAAACGGCCCCACCCCTATCTCCCTTCGCTGACTCTCTTTTCG
GACTCAGCCCGCCTGCACCCAGGTGAAATAAACAGCCATGTTGCTCACAC
AAAGCCTGTTTGGTGGTCTCTTCACACGGACGCGCATGAAA The invention as described herein is not limited to the specific LTR7 sequences as disclosed above, but to functionally analogous sequences that exhibit essentially the same desired properties as shown for these particular examples. Sequence variants with a sequence identity of at least 70%, 75%, 80%, 85%, 90% or 95% to the specific sequences listed, in addition to complementary sequences, corresponding RNA or other nucleic acid sequences, or other derivatives, are also encompassed within the scope of the present invention. The determination of sequence identity can be carried out by a skilled person without undue effort, for example using sequence comparison tools such as BLAST or Clustal.

The sequences provided above relate to human LTR7 sequences. Analogous sequences, for example those derived from other primate species, are encompassed by the present invention.

Primates refer to placental mammals of the order Primates, typically having hands and feet with opposable digits, and a highly developed brain. Primates include, without limitation, humans, lemurs, lorises, monkeys and other apes, in particular humans (genus Homo), chimpanzees (genus Pan), gorillas (genus Gorilla), orangutans (subfamily Ponginae), gibbons (family Hylobatidae), Old World monkeys (superfamily Cercopithecoidea), New World monkeys (parvorder Platyrrhini), tarsiers (superfamily Tarsioidea), lemurs (superfamily Lemuroidea), lorises (superfamily Lorisoidea).

Definition of Naïve Pluripotent Stem Cells:

Murine naive ESCs have a series of unusual properties: both X chromosomes are active, they form 3D rounded clusters, resembling a E4.5 epiblast of preimplantation blastocyst[1], and they don't expresses genes typical of differentiated cells. Human characteristics may however differ.

The GFP$^{high}$ cell line that the inventors have established shows the above features. In the 2i/LIF condition the GFP$^{high}$ cells stably maintain naive-like morphology for a good time (followed for Passage 20, over 100 days, and ongoing) (for passage 9 see FIGS. 4a, 12a-d). In an analysis of 5 culture media, for longer-term culture 3iL[4] medium proved beneficial (FIGS. 11e-h), but with room for optimization. Additional optimization of the medium has provided the 4i-medium, which is capable of maintaining the naïve state, as evidenced by LTR7 transcription, for long periods of time without the need for re-sorting.

This invention establishes that much of the circuitry regulating pluripotency in hPSCs is primate/human specific. This observation could explain why some currently identified human naïve-like cells[2-6] are not identical to the murine state. Thus, we cannot expect the human naïve cells to have the same defining features as murine naïve cells[7]. More particularly, recent studies reveal that certain murine naïve phenotypes, including the absence of X inactivation[8] or 3D morphology (FIG. 11j) appear to be imperfect to characterize cultured human naïve cells.

Alternatively, naïvety may be defined by functionality. Behavior within a chimera is thought to be one of the most stringent functional assays. Consistent with this view, in contrast to EpiSCs, naïve mESCs can efficiently integrate into the ICM of blastocyst and generate normal chimeras, indicating their full developmental potential.

According to the present invention the expression profile of cells may be used to identify "naivety", for example those cells that closely resemble cells of the inner cell mass (ICM) may be considered as a naïve or naïve-like PSC. To this end, the cells described herein, enriched using the HERVH reporter, are good representatives of naïve cells as they cluster nearest to ICM when compared with the 'novel naïve' cells obtained in reference 4 (FIG. 4e). As used herein, the term naïve pluripotent stem cell relates preferably to the LTR7-expressing naïve pluripotent stem cell as described in detail herein. These cells may be referred as "naïve pluripotent stem cell" due to the closeness of their expression profiles to cells of the ICM.

BRIEF DESCRIPTION OF THE DRAWINGS

The figures demonstrate a number of specific preferred embodiments of the invention and are not intended to be limiting to the invention described herein.

a, Expression of various Transposable Elements (TEs) in human induced pluripotent stem cells (hiPSC), hESC (H1), and human fibroblast HFF-1. Colours indicate different classes of TEs (red, long terminal repeat elements (LTR); green, long interspersed nuclear elements (LINE); blue, short interspersed nuclear elements (SINE); grey, other repeat elements). b, The proportion of active loci in each HERV family. c, Relative mRNA levels of HERV(H/K/W) in hESC (HES-3), various hiPSCs lines and their parental somatic cells. d, Effect of long-term culturing on HERVH transcription levels in hiPSCs generated from HFF-1. P, passage number. c, d, mRNA levels are normalized to GAPDH, and relative to HES-3. Error bars, s.d. (n=3 independent cell cultures), t-test, *P<0.05.

Figure 2:
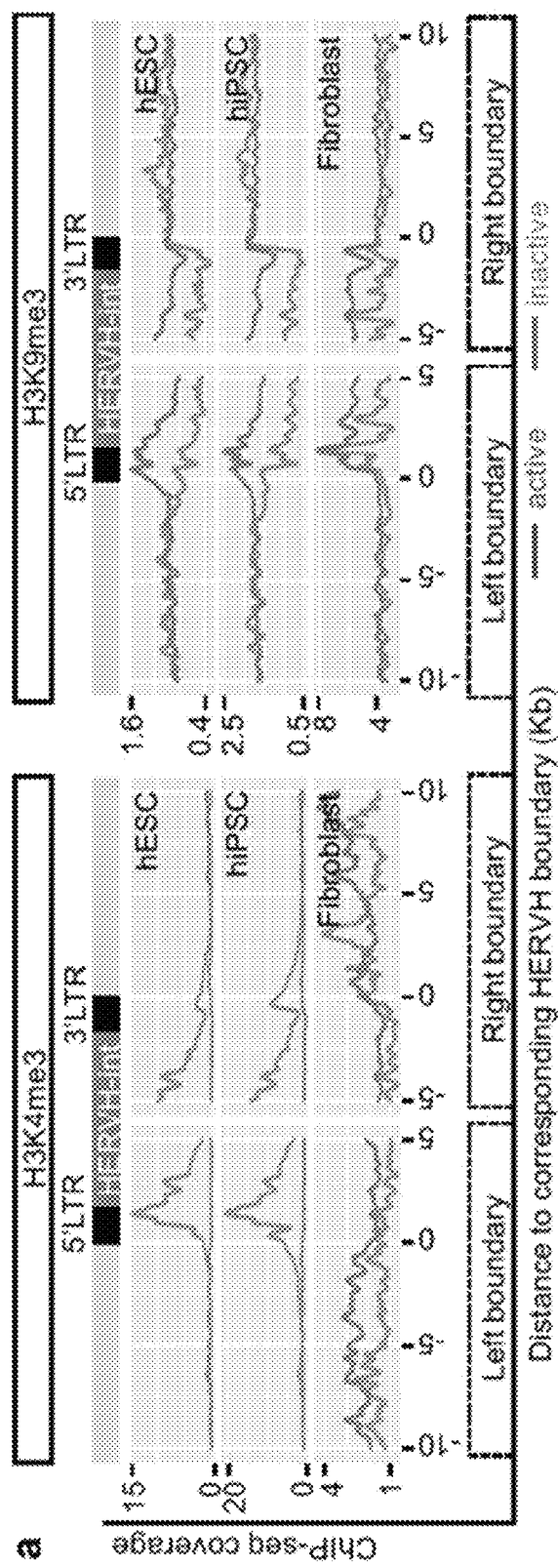
Figure 2:
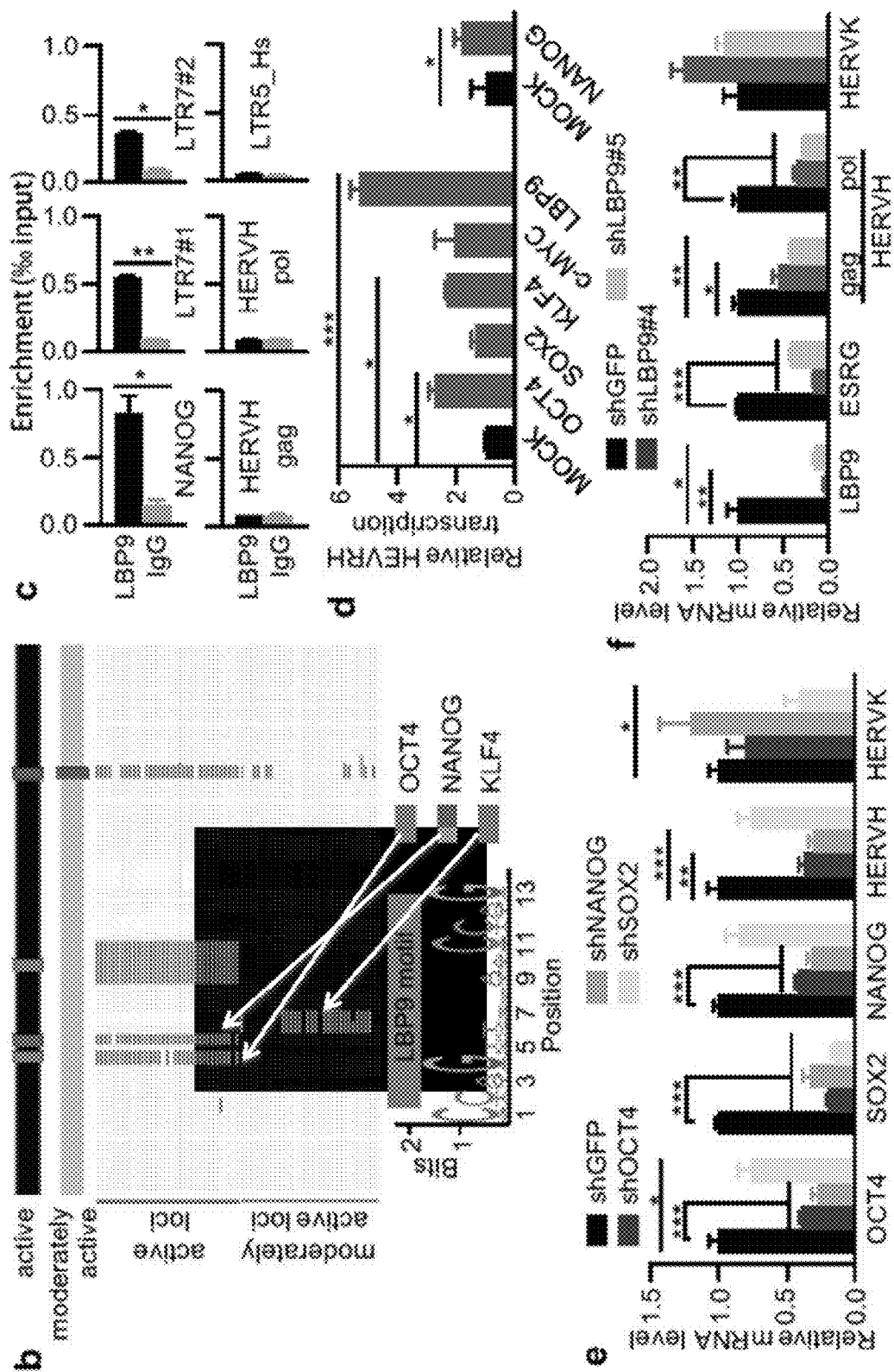

FIG. 2. HERVH is recruited into the circuitry of human pluripotency a, The distribution of H3K4me3 and H3K9m3 in active vs inactive HERVH regions in hiPSCs, hESCs and HFF-1. b, Conserved binding sites of OCT4, NANOG, LBP9 and KLF4 are shown in active LTR7s vs moderately active versions of LTR7Y/C. The Jaspar consensus sequence of the LBP9 is shown. c, Confirmation of LBP9 binding to LTR7 by ChIP-qPCR with two different primers (LTR7 #1, #2) targeting LTR7 regions. HERVH-gag, HERVH-pol and LTR5_Hs (LTR of HERVK) served as negative controls, while an upstream region of NANOG (7.5 kb from TSS) was a positive control. Data are collected from two independent experiments with biological replicates per experiment (LBP9: n=3; IgG: n=2), error bars, s.d.; t-test *P<0.05, **P<0.01. d, Upregulation of HERVH transcription in HFF-1 regulated by exogenous pluripotency-associated transcription factors. Data are collected from three independent experiments with biological triplicates per experiment. e-f, Effects of shRNA knockdowns of various TFs on HERVH and HERVK transcription in hESC_H9. Data shown are representative of three independent experiments with biological triplicates per experiment. d-f, error bars, s.d.; t-test *P<0.05, P<0.01, P*<0.001.

Figure 3:
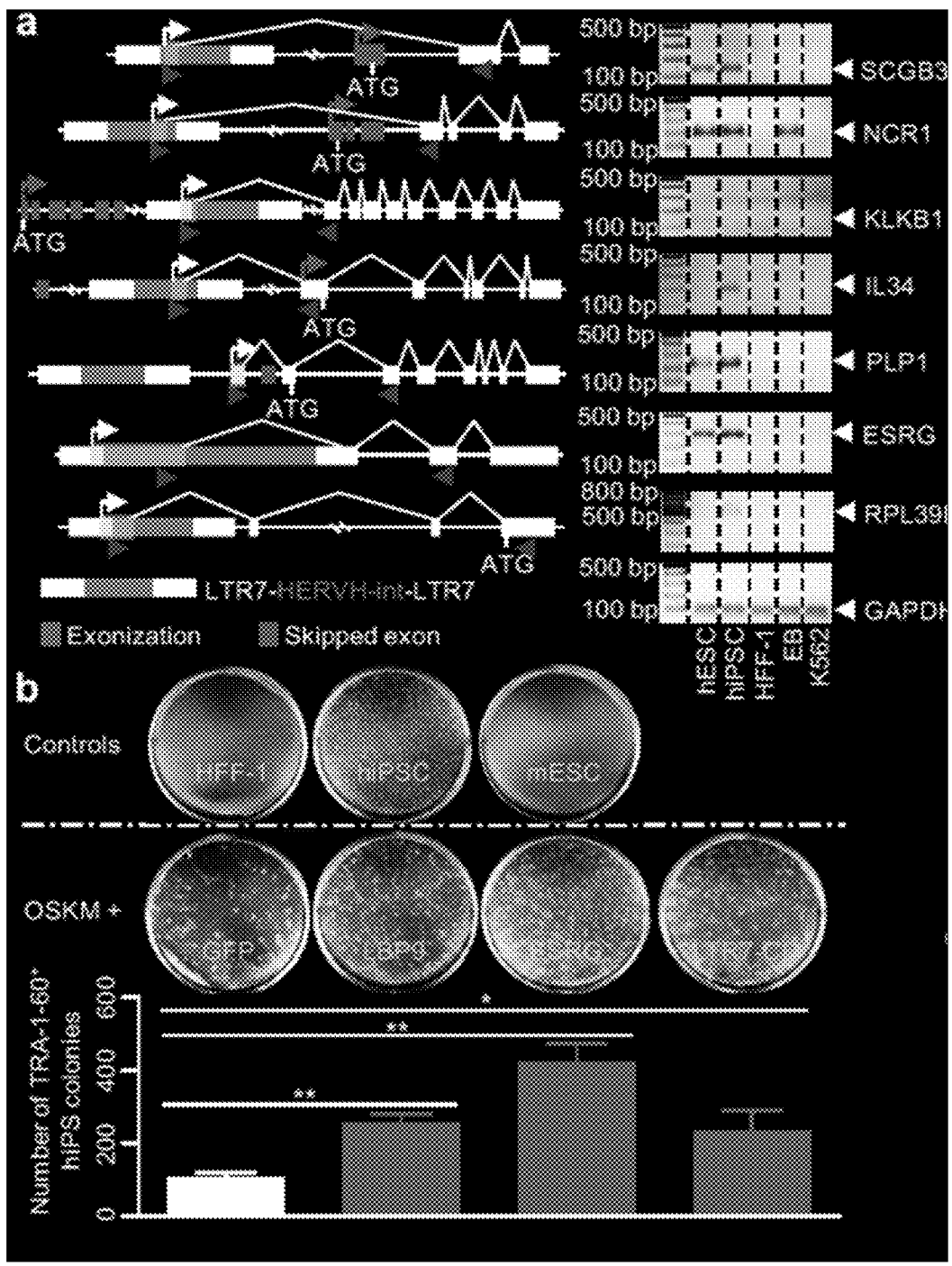
Figure 3:
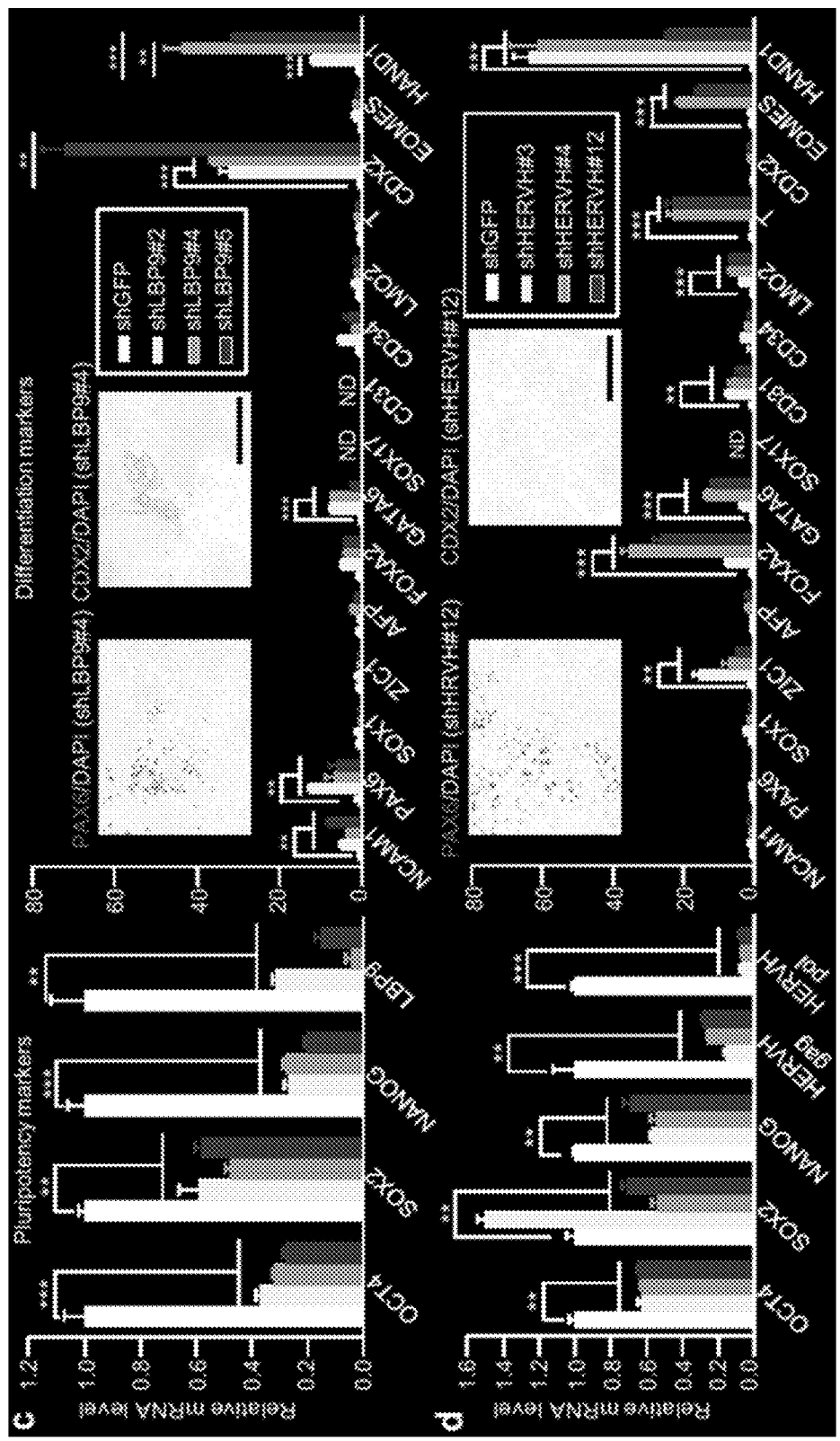
Figure 3:
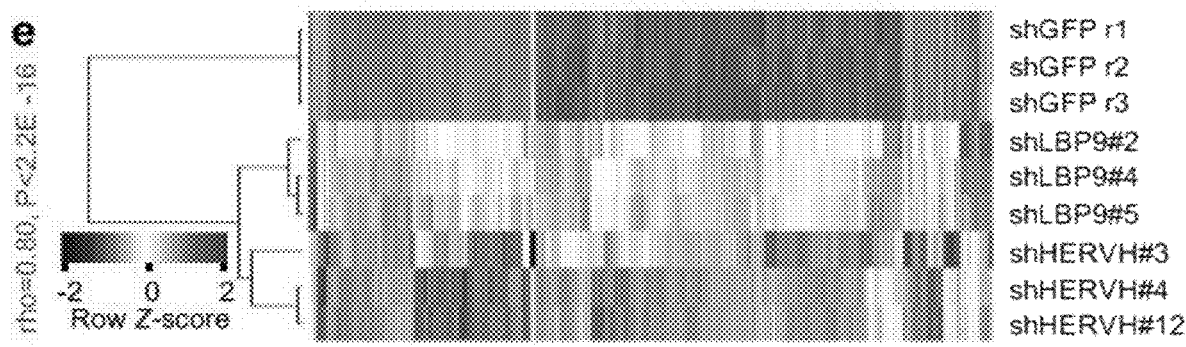
Figure 3:
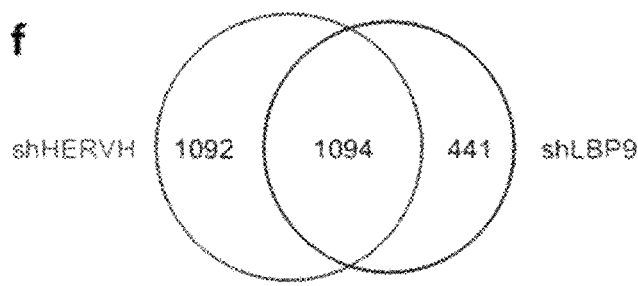

FIG. 3. HERVH triggers pluripotency-regulating hPSC-specific chimeric transcripts and lncRNAs a, Expression of HERVH forces diversification of transcripts in hPSCs. Left: schematic representation of the HERVH-derived alternative and chimeric transcripts. Right: RT-PCR detects HERVH-specific transcripts (marked by triangles) in hPSCs and NCR1 in embryoid body (EB), but not in HFF-1 or K562. Yellow arrows indicate primer binding sites. b, The effects of LBP9 and HERVH-derived transcripts on reprogramming of HFF-1 to hiPSCs. Upper panel: Representative TRA-1-60 stained wells are shown. Lower panel: The number of TRA-1-60$^+$ hiPS colonies reprogrammed from HFF-1 by LBP9, ESRG or LTR7-CD in conjunction with OCT4, SOX2, KLF4 and c-MYC (OSKM). Error bars, s.d., t-test *P<0.05, **P<0.01 from three independent experiments. c-d, qRT-PCR analyses to determine the relative expression level of pluripotency and differentiation markers after knockdown of LBP9 (c) or HERVH (d) in hESC_H9. Data shown are representative of three independent experiments with biological triplicates per experiment. Error bars, s.d., t-test *P<0.05, P<0.01, and *P<0.001. ND, not detected. Representative immunostainings show the expression of PAX6 and CDX2 in LBP9 and HERVH knockdowns (scale bar, 100 μm). e, Heat map showing genome-wide gene expression in hESC_H9 following knockdown of GFP (shGFP), LBP9 (shLBP9) and HERVH (shHERVH). The knockdown effect of LBP9 and HERVH are highly similar (rho from Spearman's correlation). For list of affected genes, including direct targets of shHERVH see Tables S13 and S14. f, Venn diagram shows that 1094/2627 genes are similarly affected by KD-HERVH and KD-LBP9 (Table S12).

Figure 4:
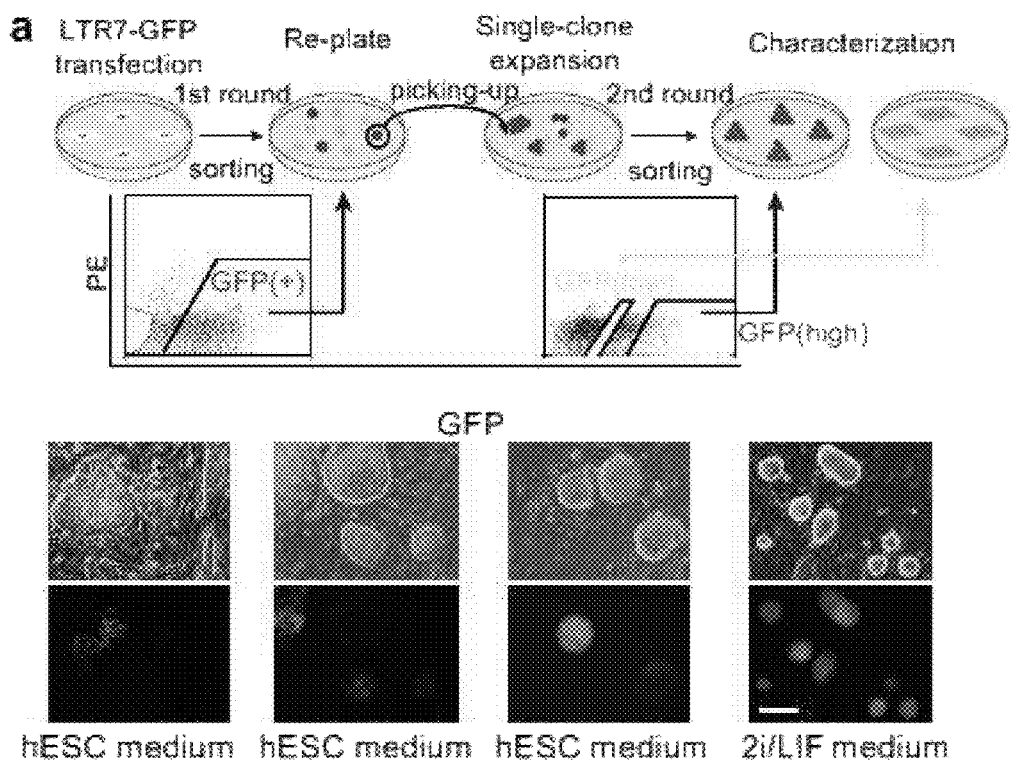
Figure 4:
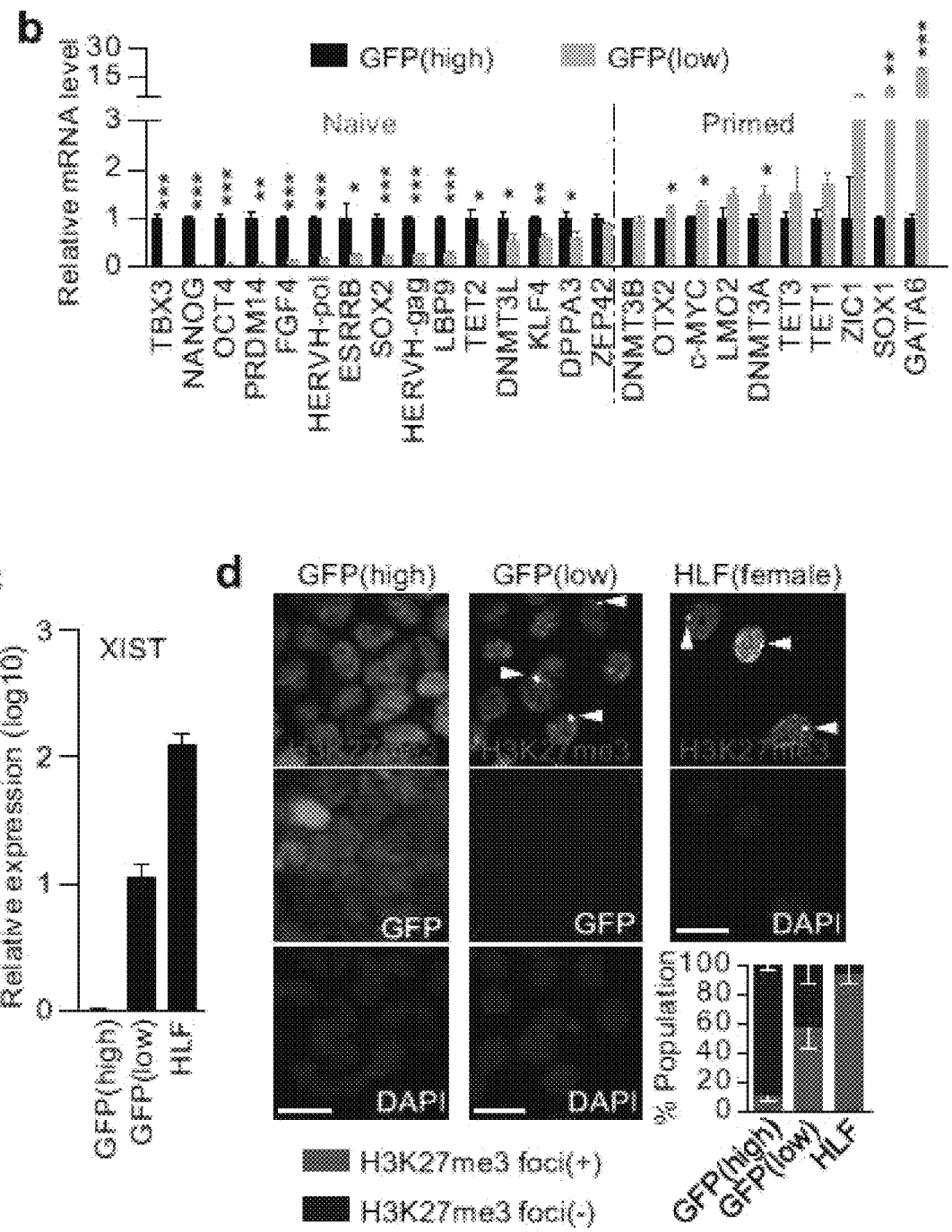
Figure 4:
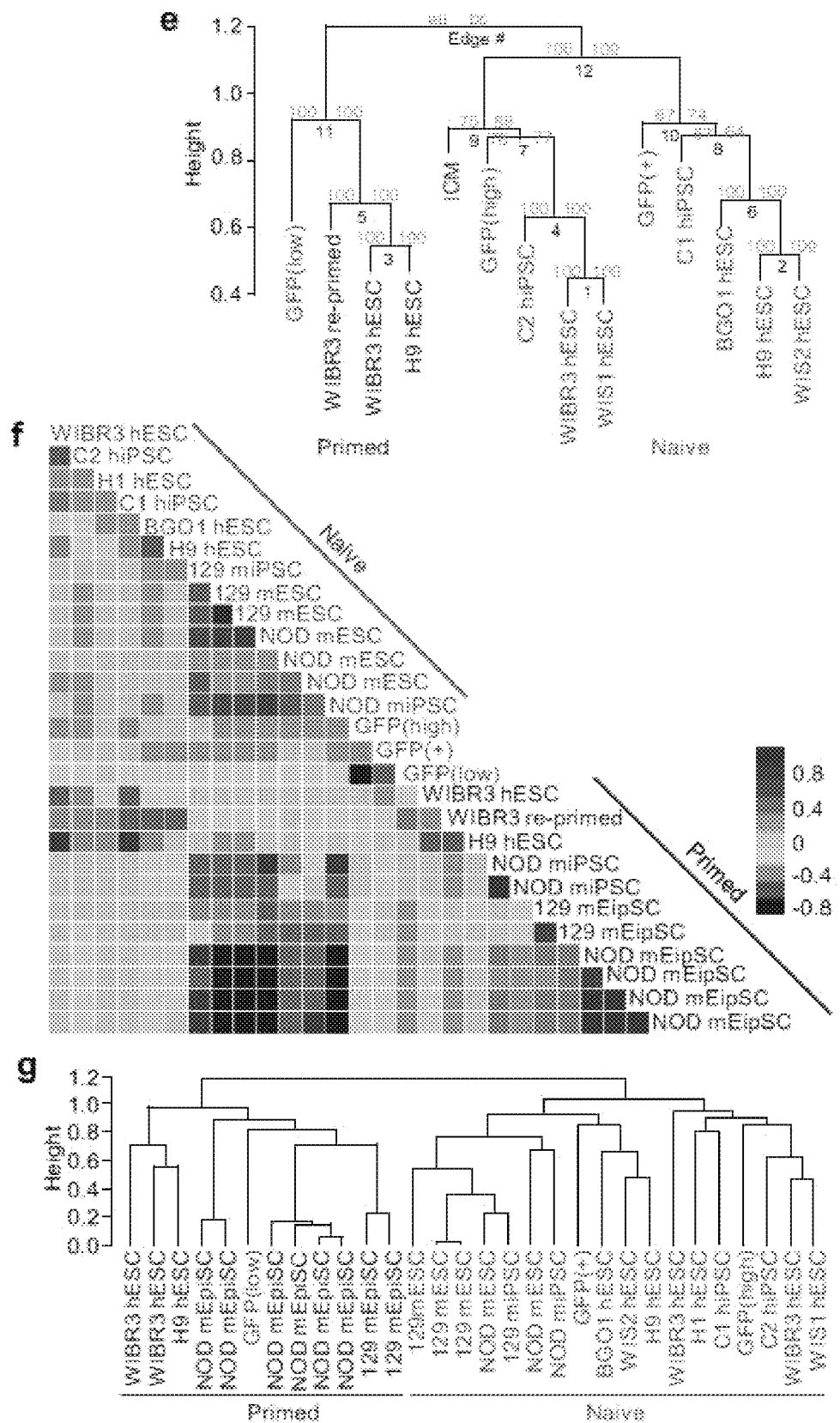

FIG. 4. HERVH genetically marks naïve-like hESCs a, Experimental scheme for isolating naïve-like hPSCs. pT2-LTR7-GFP #2-marked hESC_H9 were enriched by FACS-sorting in multiple rounds and cultured in conventional hESC medium and in 2i/LIF medium, respectively. Scale bar, 200 μm. See also Supplementary Videos S1 and S2. b, qRT-PCR analyses of multiple transcription factors and markers for naive and primed state in GFP$^{high}$ and GFP(low) cells, respectively. c, qRT-PCR analysis of XIST in GFP(high), GFP(low) hESC_H9 and human female fibroblasts (HLF). b, c, Error bars, s.d.; t-test *P<0.05, P<0.01, and *P<0.001 (n=3 independent cell cultures). d, Representative confocal images obtained after immunostaining for H3K27me3 on GFP(high), GFP(low), hESC_H9s and HLF. Scale bar, 20 μm. The proportions of H3K27me3 foci(+) (triangles) and (−) cells in each sample are shown in the histogram. Error bar, s.d. Data were obtained from 100-450 cells counted from five images per sample. e, Global expression cluster dendrogram between GFP(high), GFP(+), GFP (low) hESCs_H9, human inner cell mass (ICM) and previously established human naïve and primed cell lines[4]. Approximately Unbiased (AU) probability, Bootstrap Probability (BP) values and edge numbers at P-value less than 0.01 are shown. ICM clusters closest with GFP(high)— nodes 7,9. f, Correlation matrix displaying the unbiased and pairwise comparison of mouse-human orthologous gene expression between GFP-marked hESC_H9 (this study, green) and mouse and human[4] naïve as well as primed PSCs. Color bar indicates Spearman correlation strength. g, Cluster analysis using the average distance method on the same dataset as in f. GFP(high), GFP(+) and GFP(low) cells in e-g were collected from hESC_H9 cells cultured in conventional human ESC medium by FACS-sorting.

Figure 5:
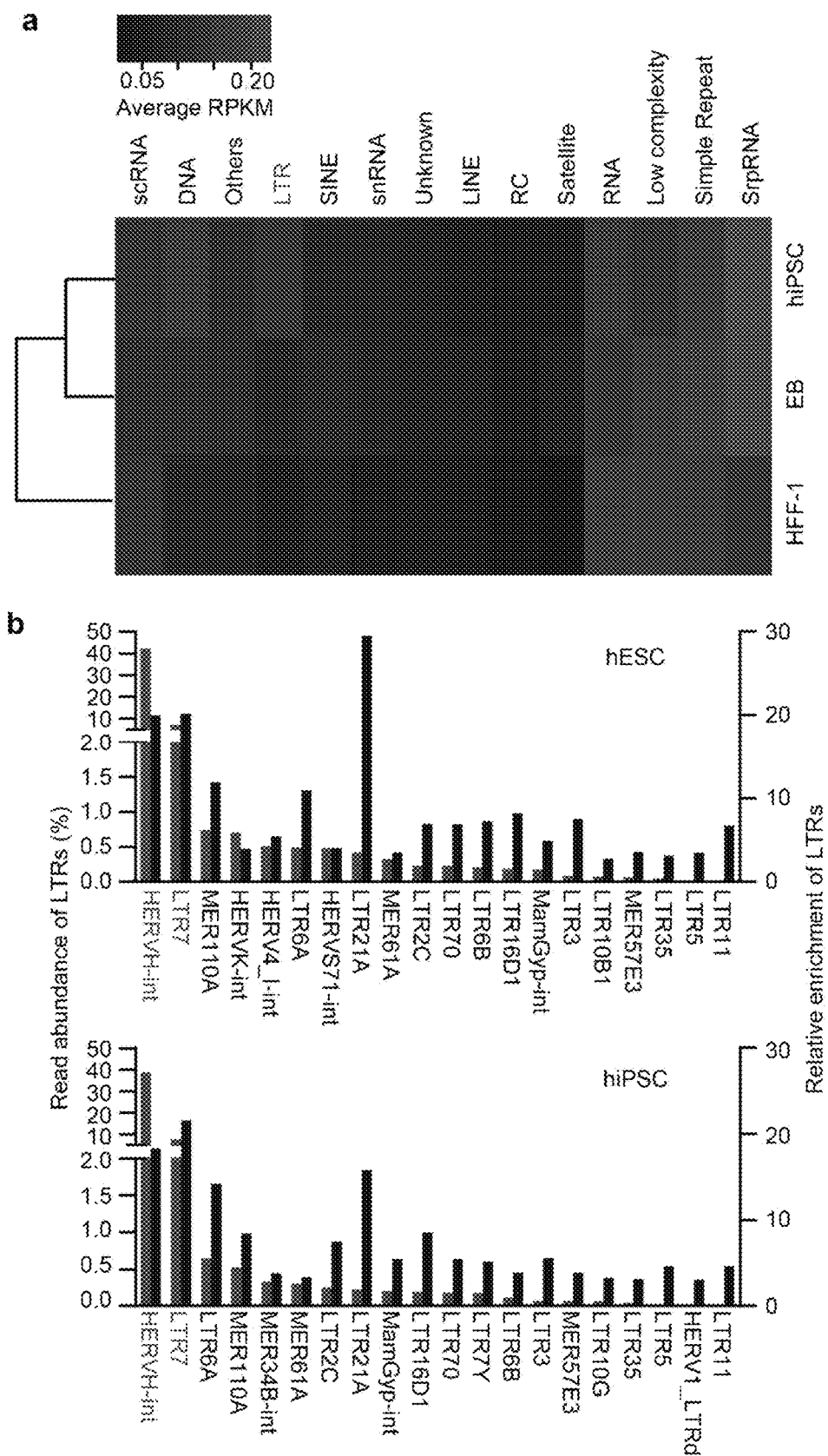
Figure 5:
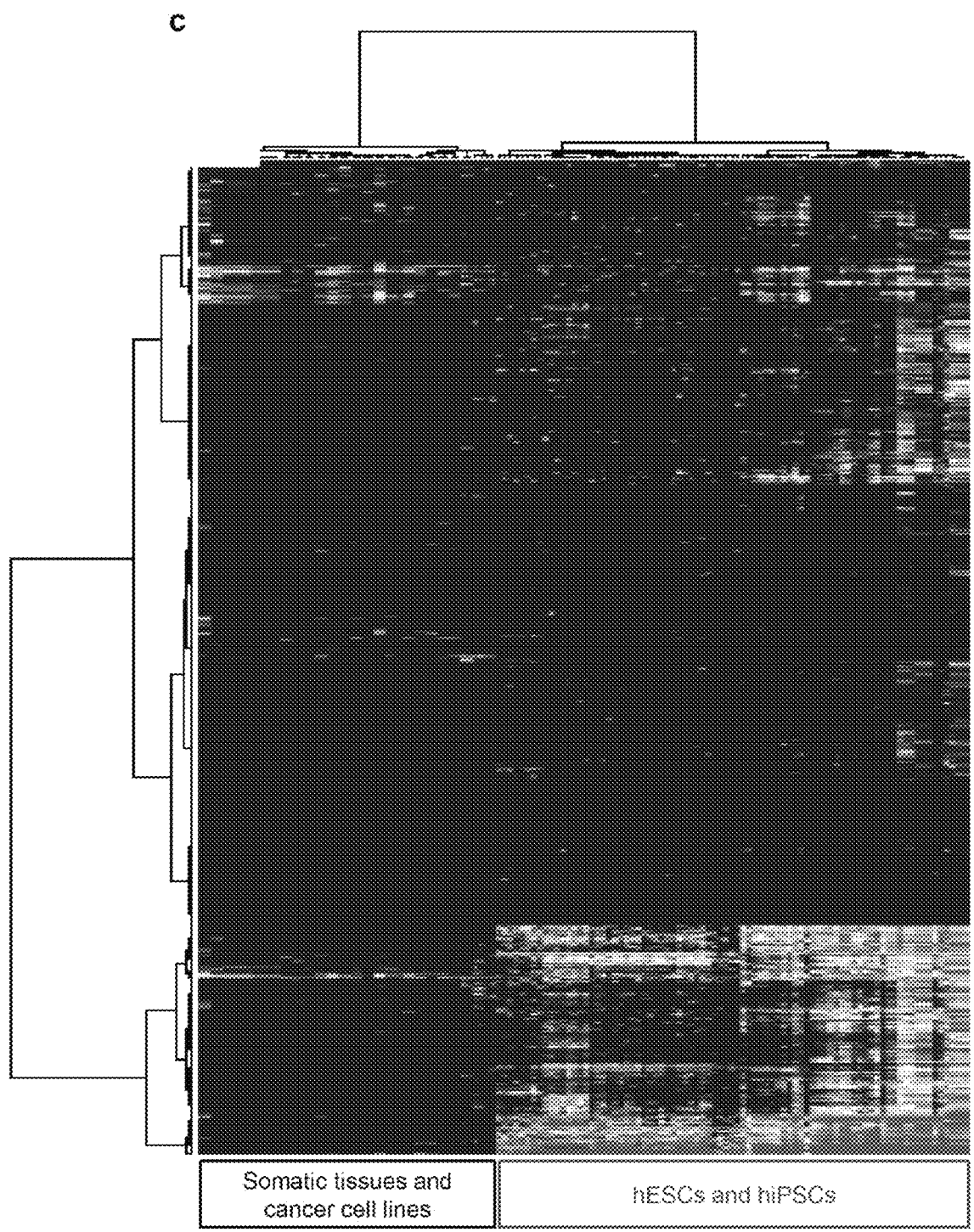
Figure 5:
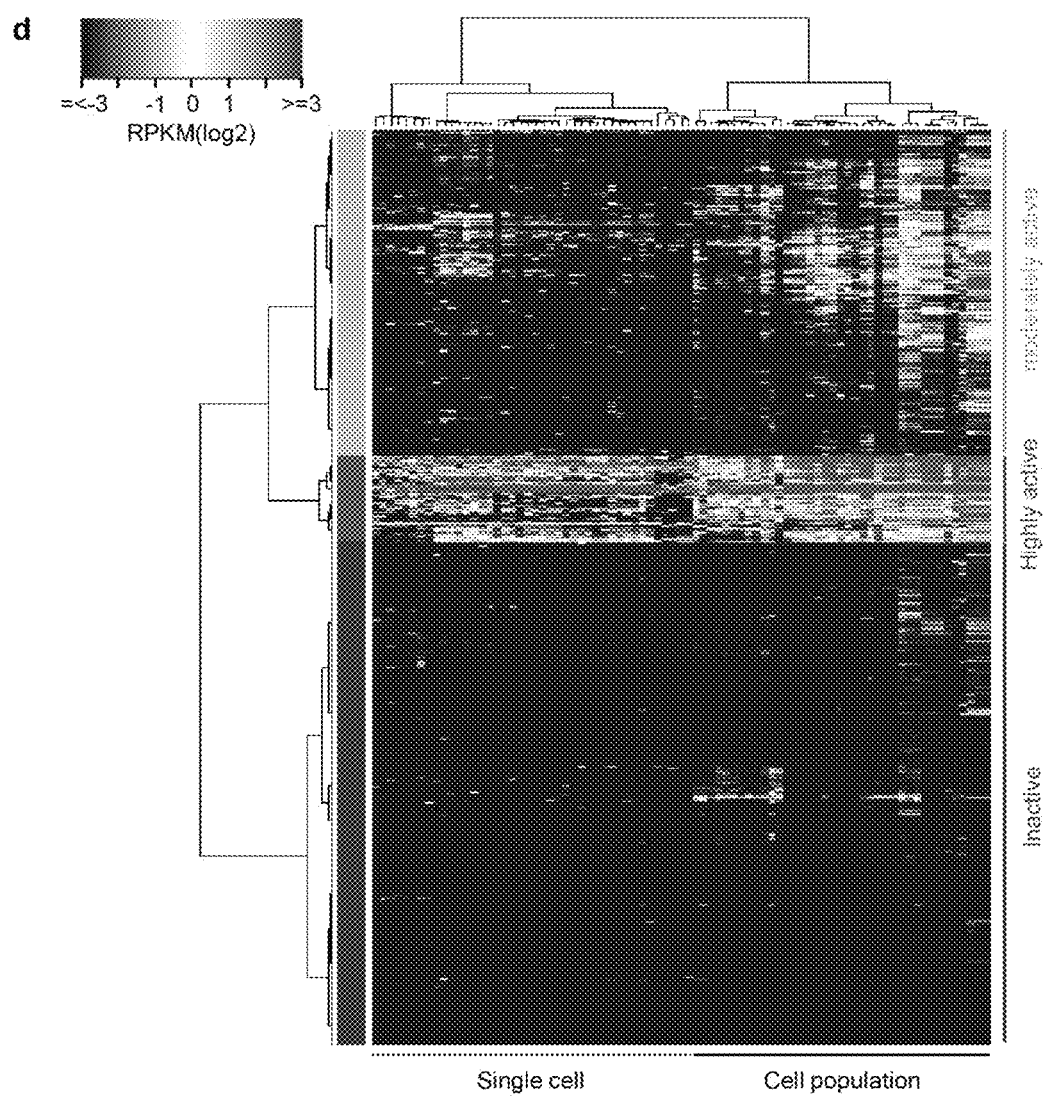
Figure 5:
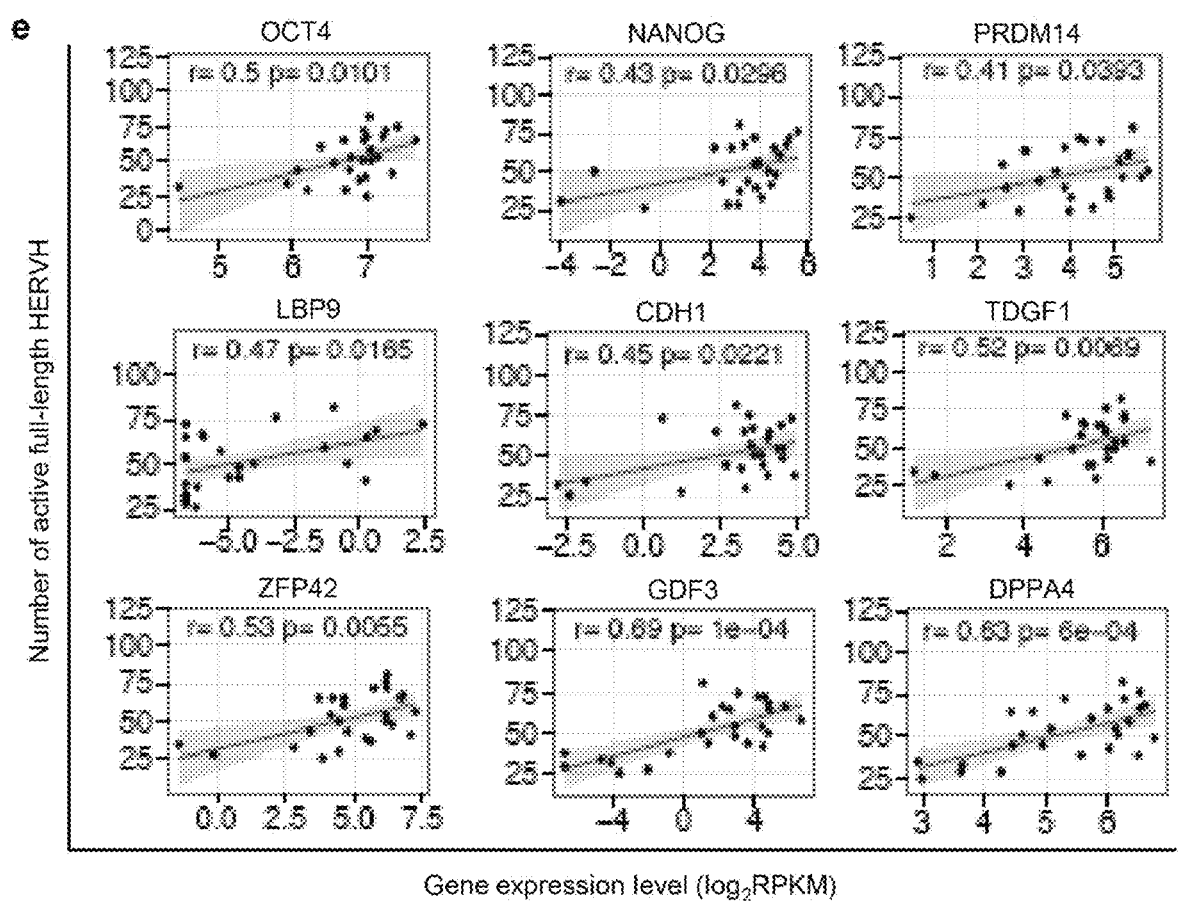

FIG. 5. HERVH is the most transcriptionally enriched TE in hPSCs a, Heatmap showing expression of repetitive element classes in human induced pluripotent cells (hiPSCs), fibroblasts (HFF-1) and hiPSC-derived embryoid bodies (EBs). b, Highly expressed (top 20) LTR-elements in hESCs (upper panel) and hiPSCs (lower panel). The red bars indicate the proportion of reads of each LTR element in total LTR-element related reads. The blue bars indicate the enrichment of each LTR element relative to the background (calculation details described in Methods). c-d, Heatmaps showing the expression profile of 1225 full-length HERVHs in various human cell types. For list of samples, and expression data see Tables S4 and S7 respectively. c, Expression profile of HERVH in 43 normal somatic-, 8 cancer cell lines/tissues and 55 hESC (H1, H6 and H9), 26 hiPSC samples, including our hiPSC[30] line. The rows represent the transcription from 1255 full-length HERVH loci. d, Expression profile of HERVHs in hPSC lines and single cells from three individual hESC clones. Based on their expression, the 1225 full-length HERVH loci are clustered into three groups (highly, moderately and inactive). Note that HERVH activity is heterogenous between single cells of an hPSC population. e, HERVH expression in single hPSCs positively correlates with the expression of key pluripotency-associated transcription factors (TFs). N.B. Sox2—not illustrated—shows no correlation (P=0.59). Each dot represents a single hESC sample[24].

Figure 6:
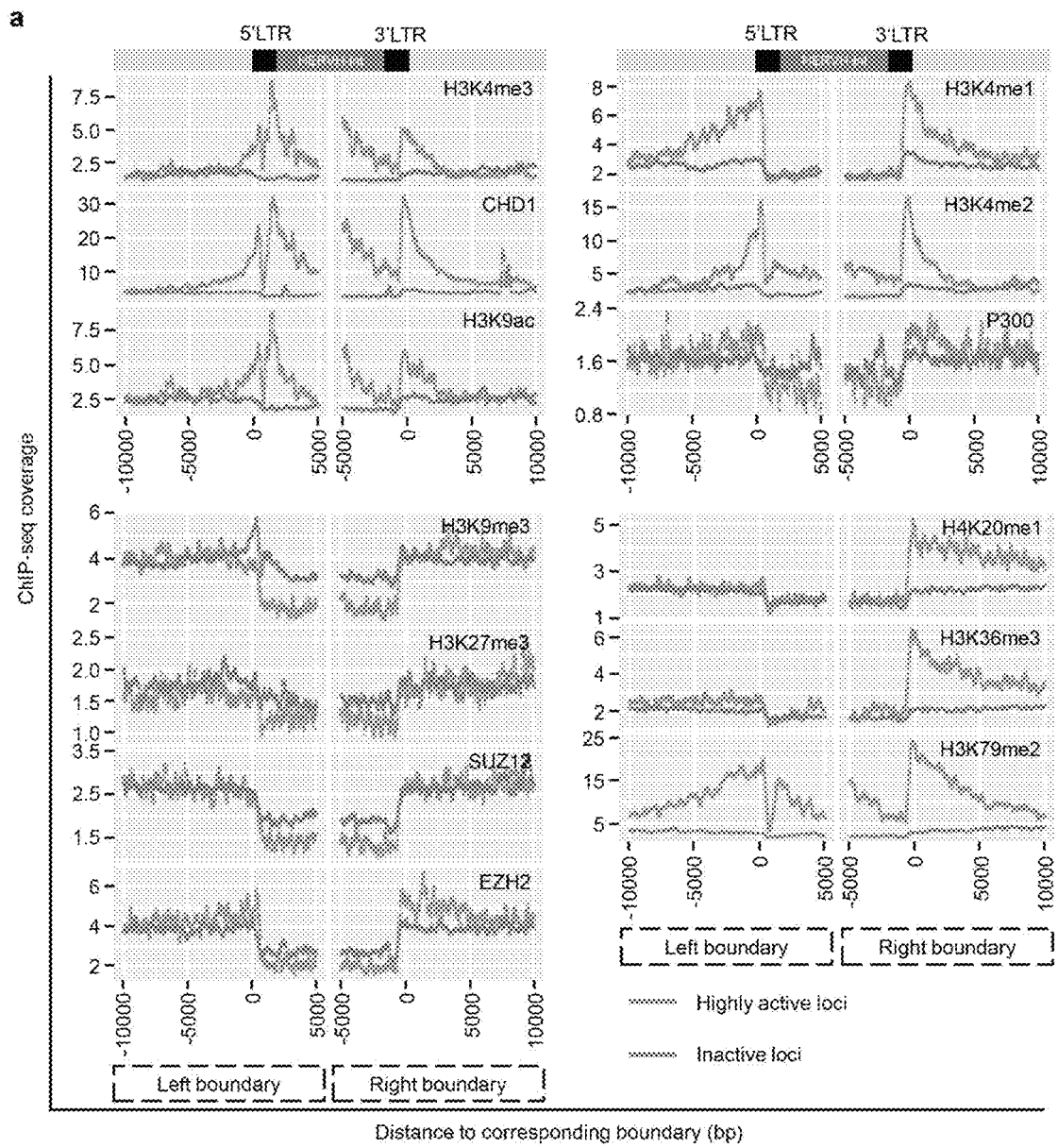
Figure 6:
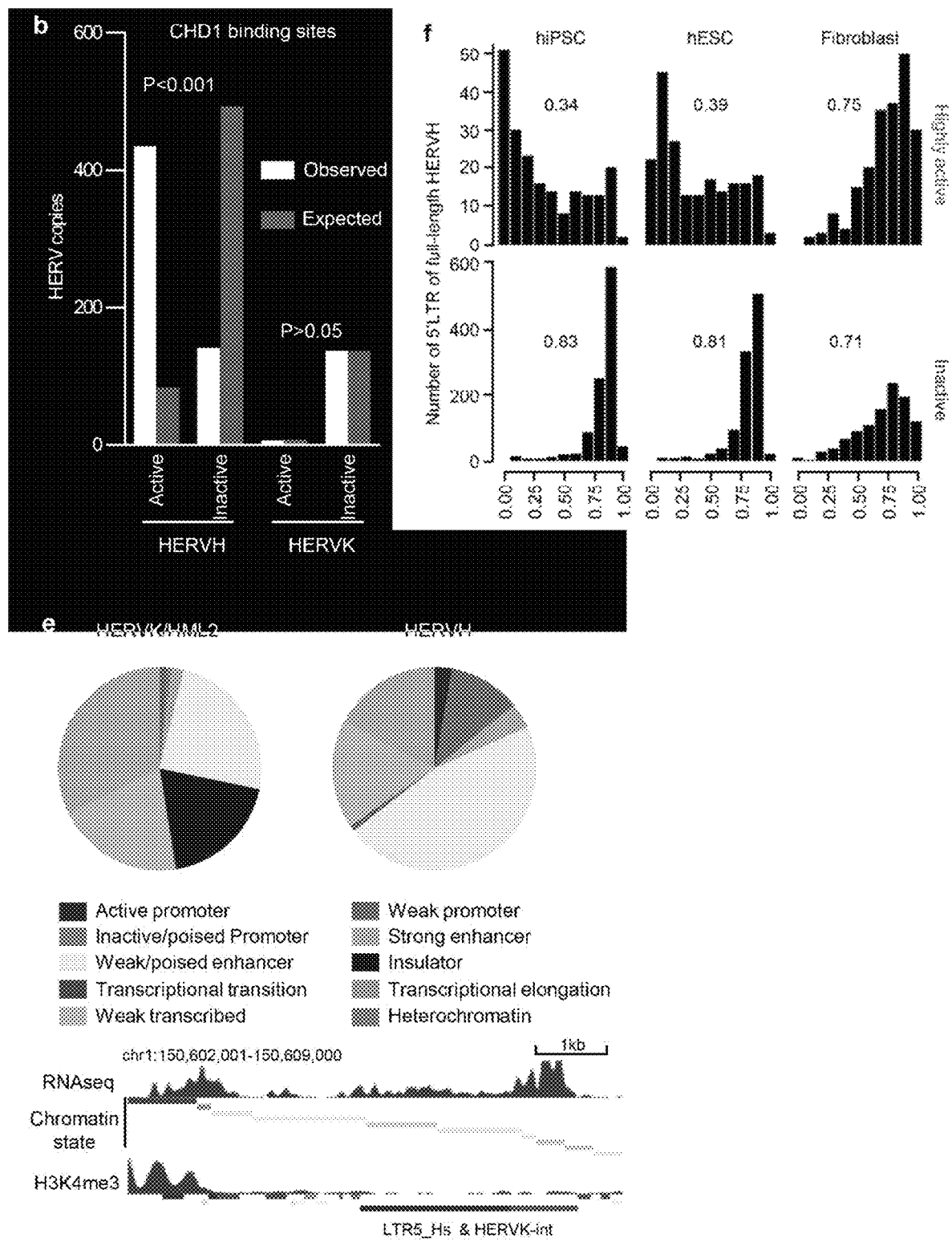
Figure 6:
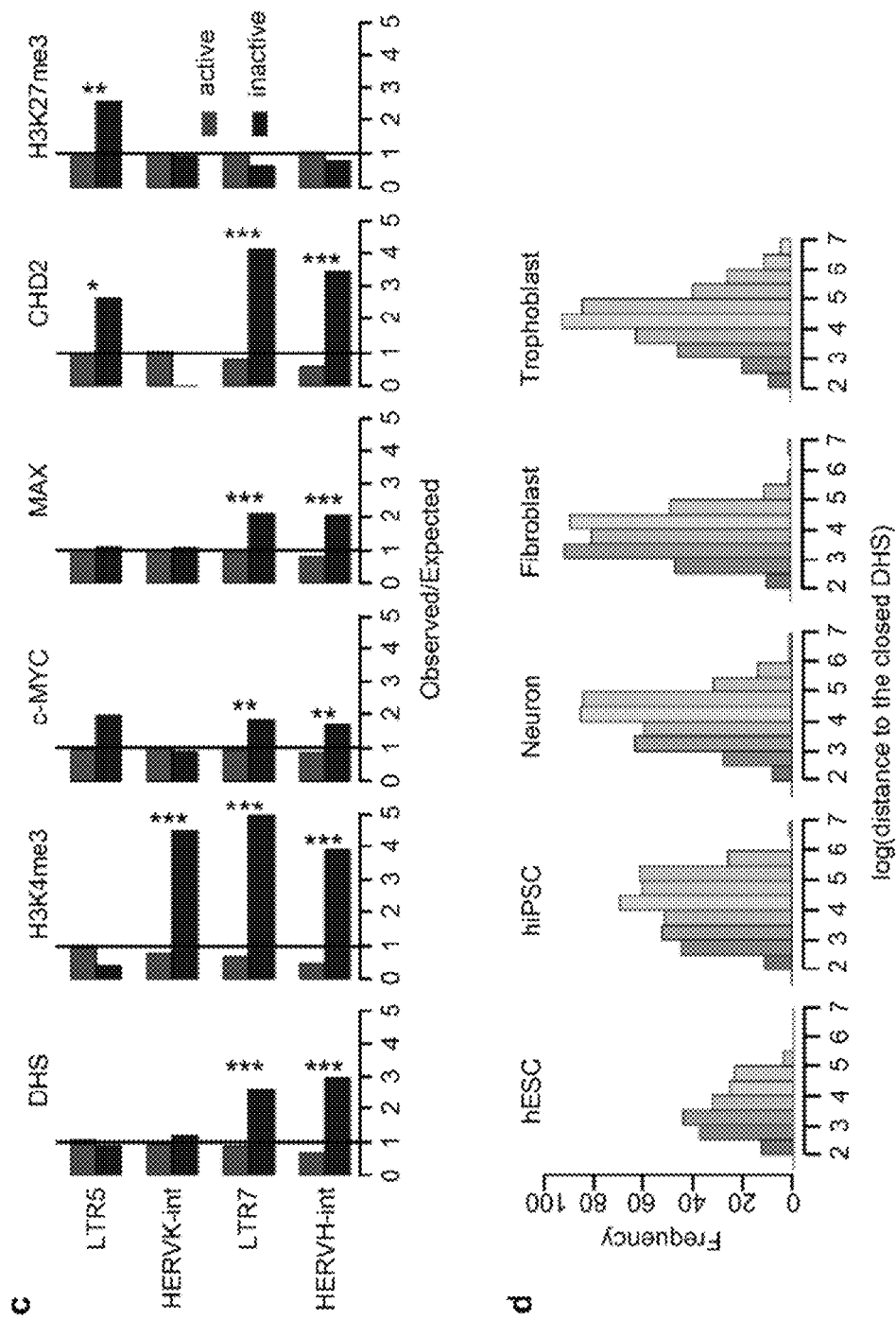

FIG. 6. HERVH shows the hallmarks of active chromatin in hPSCs.

a, Chromatin status analysis around full-length HERVHs in hESC_H1. The promoter/transcription initiation regions and the transcribed regions of active HERVH loci are associated with active epigenetic marks and chromatin modifiers. The neighbouring regions of inactive HERVH loci show the hallmarks of heterochromatin. b, Active HERVHs are enriched with CHD1's binding sites compared to inactive ones. Chi-squared tests were performed, P-values shown as statistical significance. c, Comparison of epigenetic marks and chromatin modifiers in proximity of HERVH internal sequence (HERVH-int) and LTR7. As a control, we employ HERVK-int and LTR5. We compare the number of marks within or near active and inactive versions (allowing 1.5 kb either side) of each element in ES cells. Expected numbers are derived from a null of no relative enrichment and P values determined by Chi-squared. *P<0.05, P<0.01, *P<0.001 (for data see Table S15). d, Cross-tissue comparison of the distance of the closest DHS to the active sequences not including any DHS. The distances are presented in log ratio. e, The pie charts show chromatin state segmentation for hESCs_H1 in full-length HERVK/HML2 and HERVH regions. Most of HERVK regions are repressed while a sub-population of HERVH loci is active. Chromatin status analysis of HERVK/HML2 loci reveals that transcription of the few activated HERVK loci is promoted primarily by neighbouring regulatory elements, and not by their own LTRs. The chromatin status of a representative locus is shown (the lower panel). f, Whole genome bisulfite sequencing analysis on LTR7s. Comparison of the DNA methylation status of actively transcribing (highly active) and inactive elements in three different cell types, hiPSCs, hESCs and fibroblast. Average methylation levels are shown. Data from the ENCODE project and Epigenome Atlas (Table S4).

Figure 7:
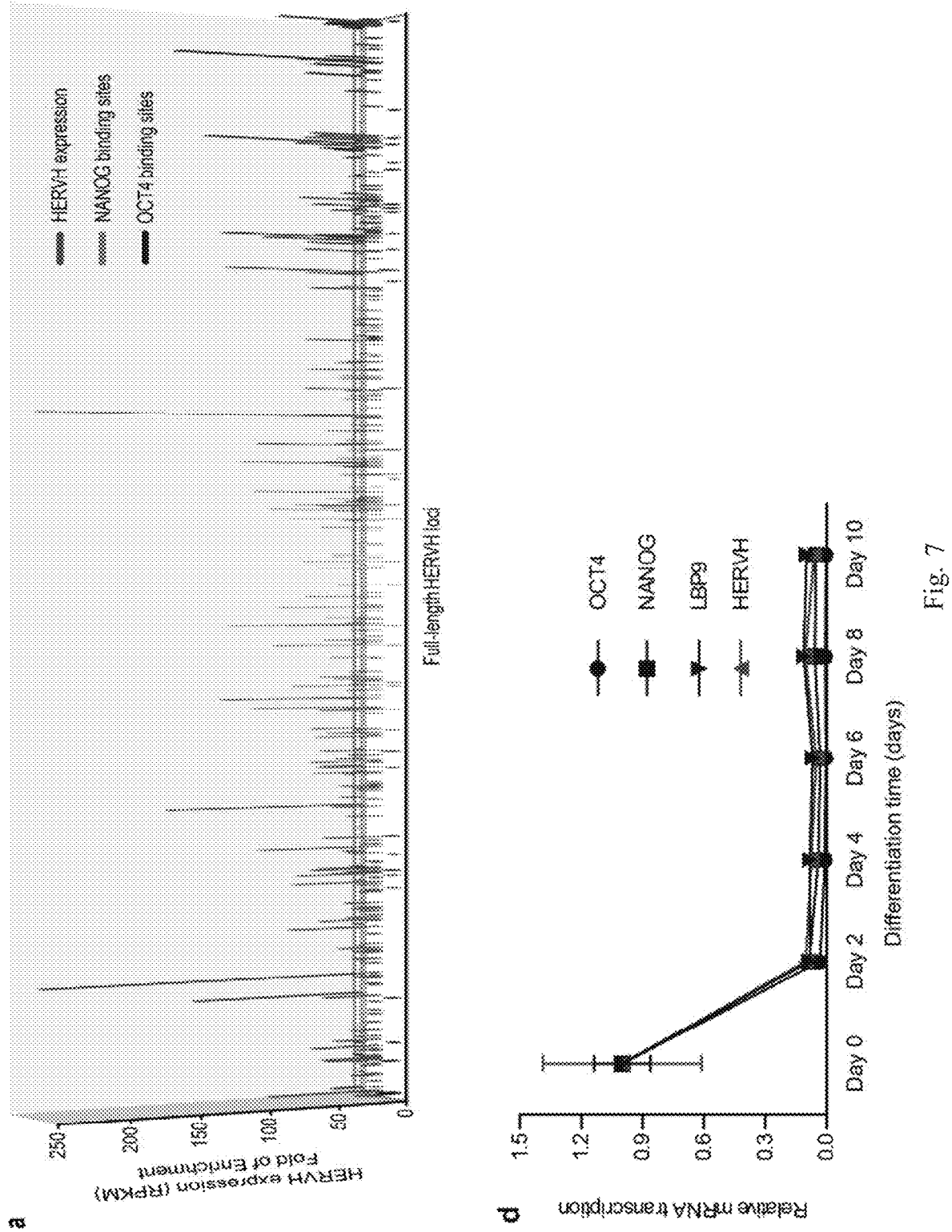
Figure 7:
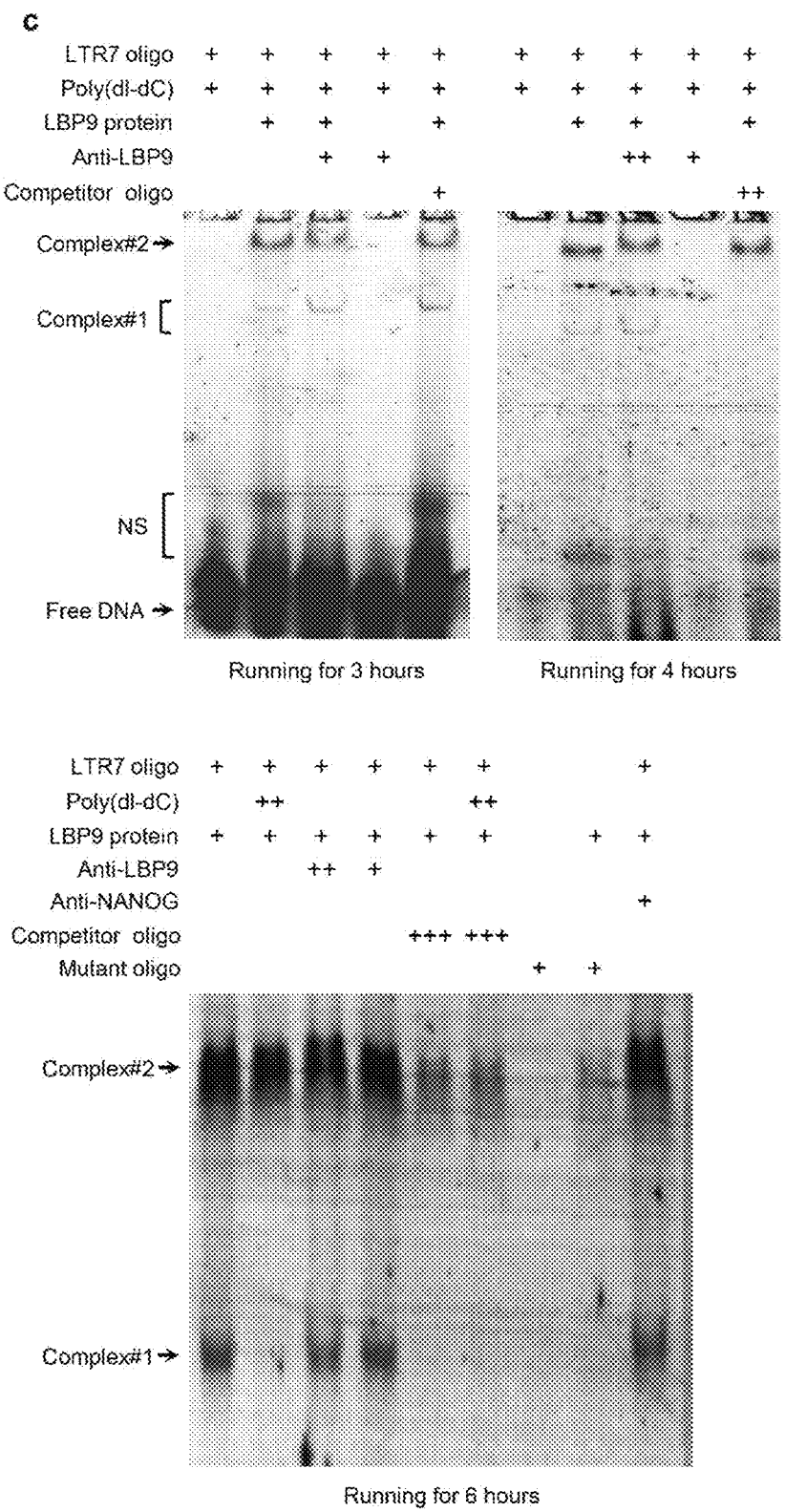

FIG. 7. Pluripotency-associated transcription factors bind to HERVH a, All 5'LTR7s of active HERVHs are associated with NANOG, while OCT4 is present in around 39. The plot combines the expression values of the 1225 full-length HERVH (RNAseq) with the fold-enrichment values of ChIP-seq data of OCT4 and NANOG in hESC_H1[3]. Each data-point reflects a single full-length HERVH element. b, Motifs found significant in CLOVER and ROVER analyses. The four comparisons are active HERVH vs GC matched control sequence, HERVH flanked by LTR7 vs those flanked by LTR7C/Y, LTR7 itself against less active HERVH and active HERVH vs active HERVK. We include only instances where the first two analyses both reported significance. Results for Tfcp2l1 alias LPB9 are shown in red. c, EMSA confirms the binding of LBP9 to LTR7 sequence in vitro. Two different complexes (C #1 and C #2) were detected in the presence of nonspecific competitor [poly(dI-dC)]. Complex #1 is lower stability (adding equal amount of competing oligo to the binding reaction doesn't destroy it, but 100× excess does). Supershift is not detected with adding anti-LBP9 antibody suggesting a lack of specificity, at least under our conditions. Complex #2 is resistant to being challenged with the competing oligo (100-fold excess), and supershifts with anti-LBP9 antibody, indicating specificity. From the low mobility we suspected Complex #2 is a large multimeric complex—this would also account for the modest but reproducible supershift. To explore the potentially multimeric nature of Complex #2, we added anti-NANOG antibody. The supershift with anti-NANOG indicates that LBP9 binds LTR7 in a complex with NANOG. ESRG-oligo 50 nM(+); poly(dI-dC), 450 ng(+), 900 ng(++); anti-LBP9, 5 μg(+), 10

µg (++); anti-NANOG 5 µg; competitor oligo, 5 nM(+), 500 nM(++), 5,000 nM(+++); mutant oligo, 50 nM; LBP9~10 µg crude extract lysate in 20 µl total reaction volume. NS, nonspecific complex. d, Relative mRNA expression levels of HERVH correlates with pluripotency-associated transcription factors (OCT4, NANOG, and LBP9) during in vitro differentiation of hiPSCs. mRNA level are normalized to GAPDH and relative to Day 0. Error bars indicate s.d. from three independent cell cultures per time point.

Figure 8:
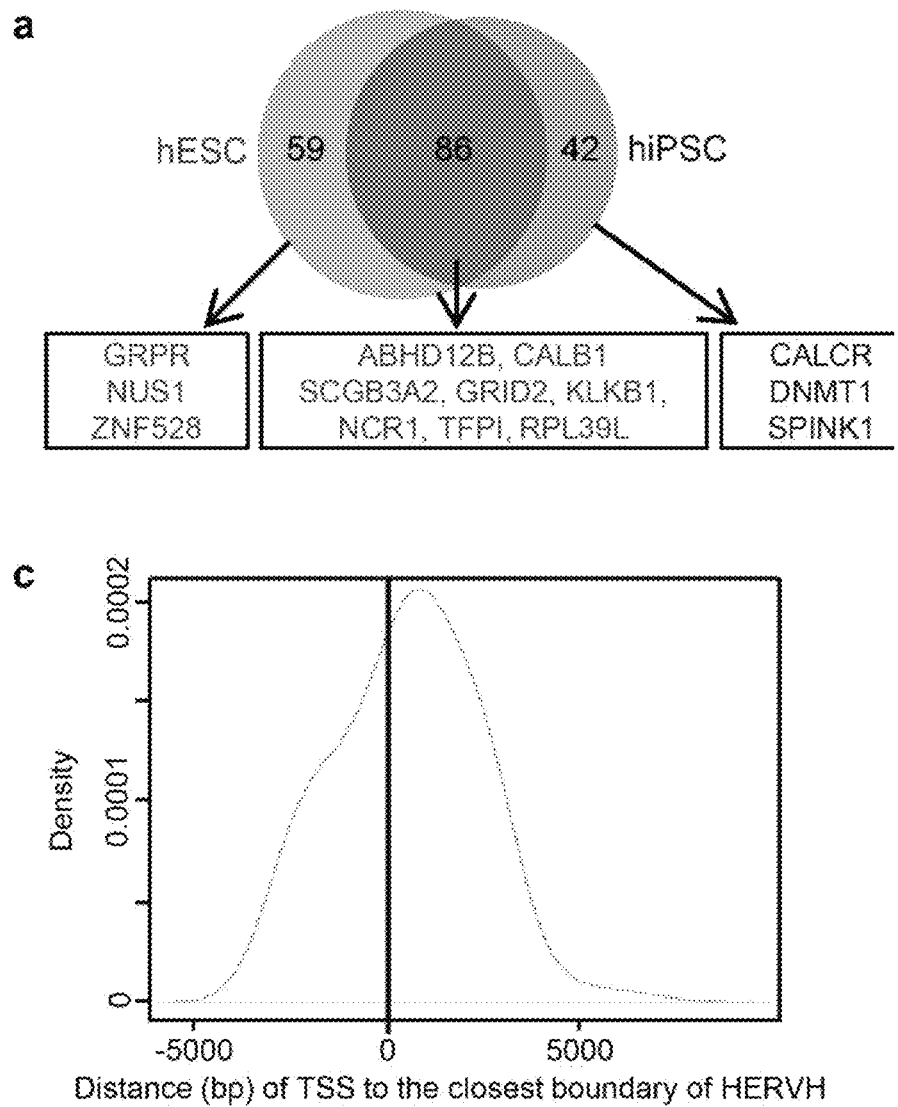
Figure 8:
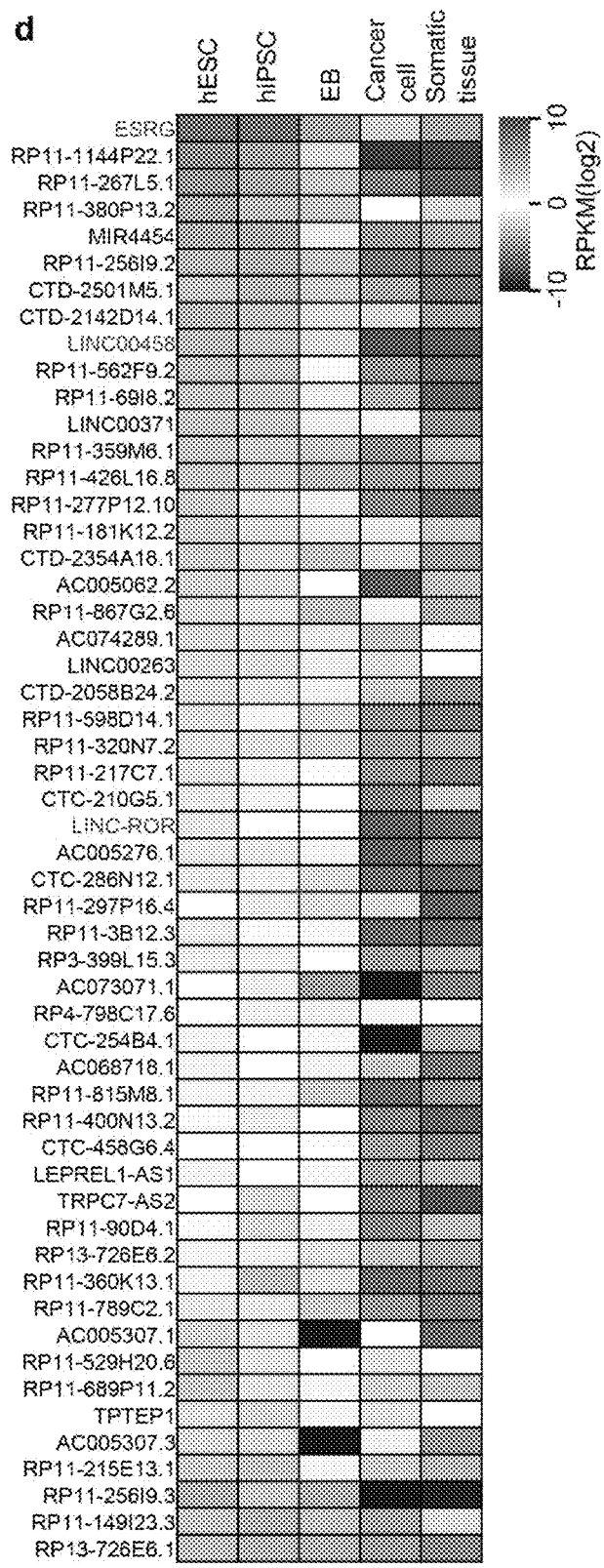
Figure 8:
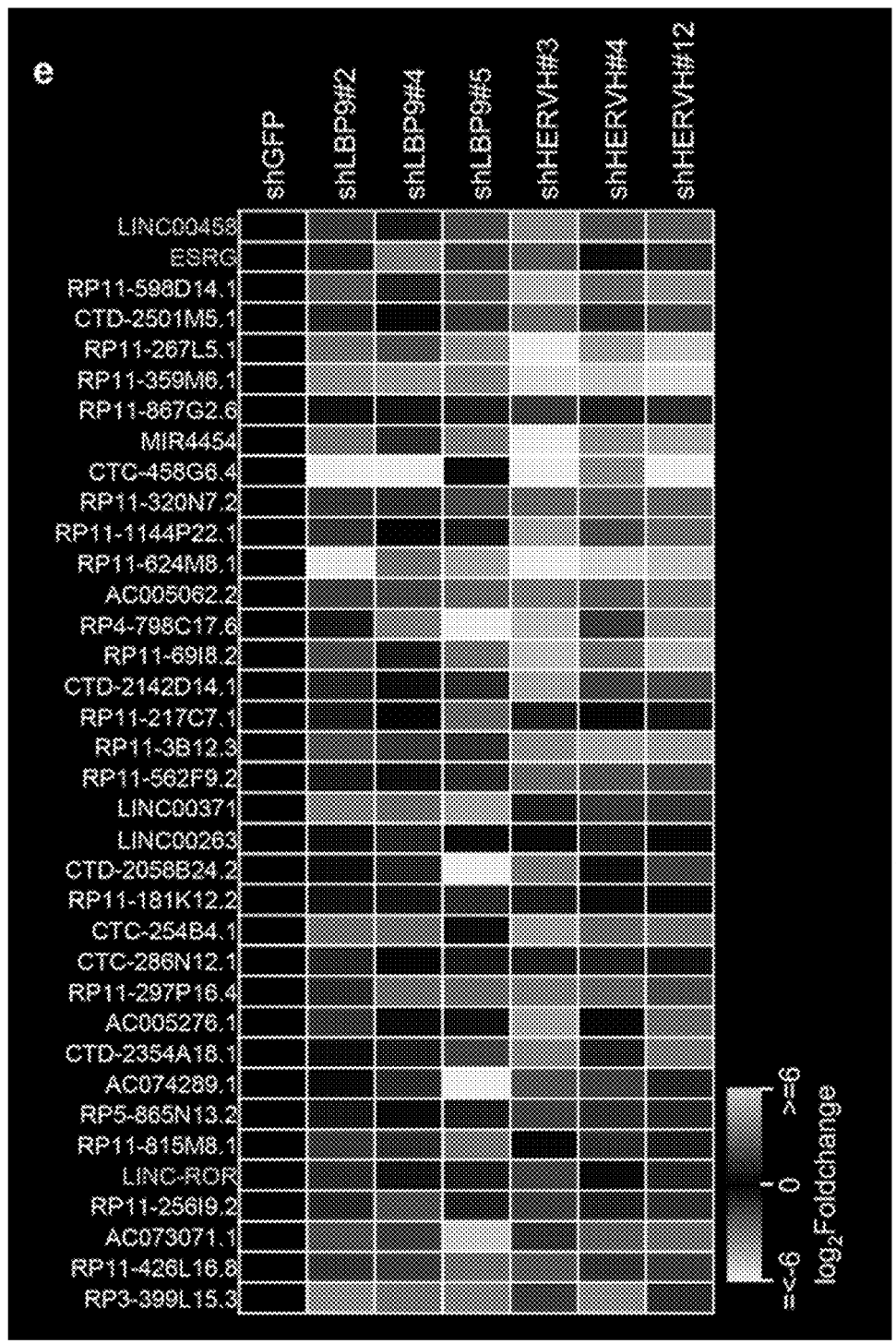
Figure 8:
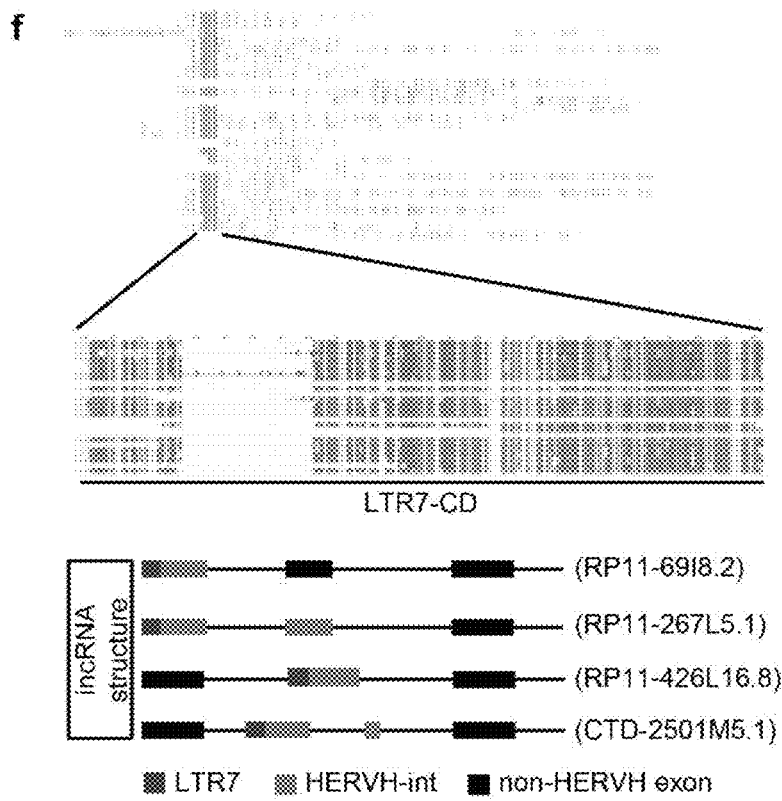
Figure 8:
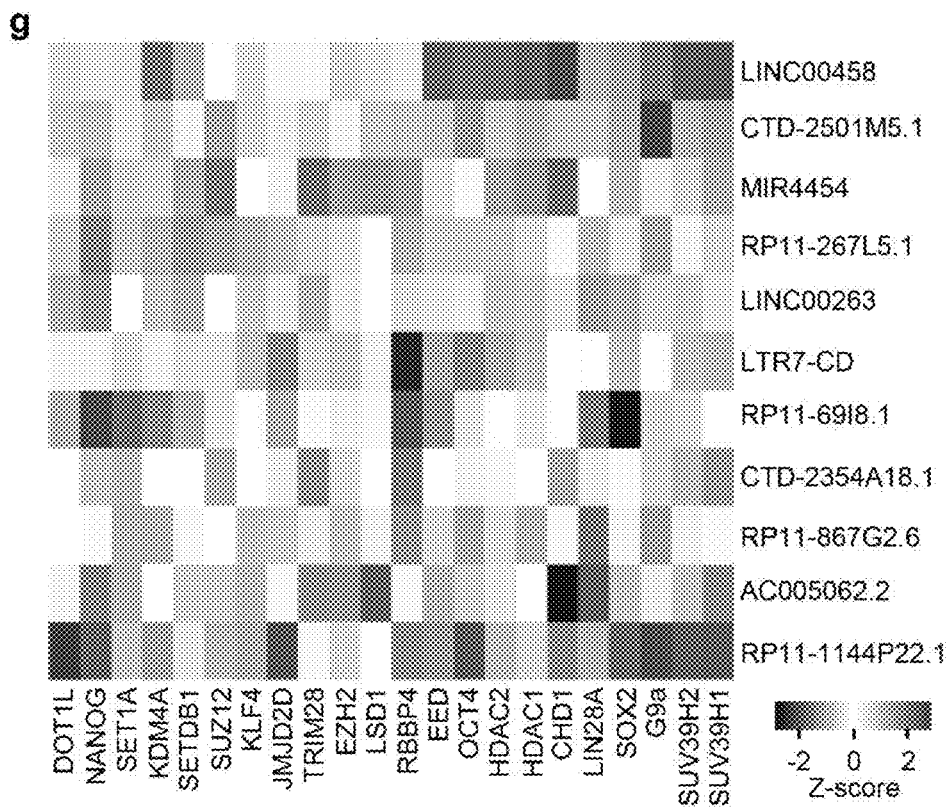

FIG. 8. HERVH driven transcription in hPSCs a, HERVH affects the neighbouring gene expression and produces HERVH-specific 'chimeric' transcripts (RNAseq reads which span HERVH and coding exons of neighbouring genes). Venn diagram shows the overlap between affected genes (see also Tables S8, S9). Examples of genes from each category are shown in boxes. b, Genes associated with HERVH function in stem cells with previously described gene functions. c, TSS distribution around HERVHs and the relationship between TSS identification and gene activity. CAGE data (from ENCODE) were analyzed to identify TSS enriched on 5' end active HERVHs. d, Expression heatmap of 54 HERVH-derived lncRNAs in hPSCs and differentiated cells. Analysis of RNAseq datasets as in FIG. E1c. Data are displayed as $\log_2$ RPKM with high and low expression shown in red and blue, respectively. EB, embryoid body (data from this study). e, Knockdown effects of LBP9 and HERVH on the highest expressed lncRNAs in hPSCs [selected from the list presented in (d)]. mRNA levels are normalized to GAPDH, and relative to shGFP expressing, undifferentiated hESC_H9. Fold-change values, relative to shGFP knockdown are shown. Note that the knockdown effects of KD-LBP9 and KD-HERVH are highly similar. f, Alignment of top 22 hPSC-specific/HERVH-derived lncRNAs predict a conserved core domain (CD, referred as LTR7-CD). Certain CDs, embedded within lncRNAs are annotated as exons, and predicted to have limited coding potential (see also Table S11). g, Heatmap of potential RNA-protein interactions (predicted by CatRAPID[31]). LncRNA were selected from FIG. E4f if they were: 1) highly expressed in hESCs; 2) down-regulated in HERVH knockdown; 3) enriched in nucleus. The Z-score describes the deviation of the studied RNA-protein interaction propensity from the ones based on randomized 100 RNAs against randomized 100 proteins (calculated by CatRAPID). The core domain of HERVH-derived lncRNAs is predicted to bind RNA-binding proteins, including pluripotency factors (e.g. NANOG), and histone modifiers (e.g. SET1A and SETDB1). High and low interaction potentials are shown in red, and blue, respectively.

Figure 9:
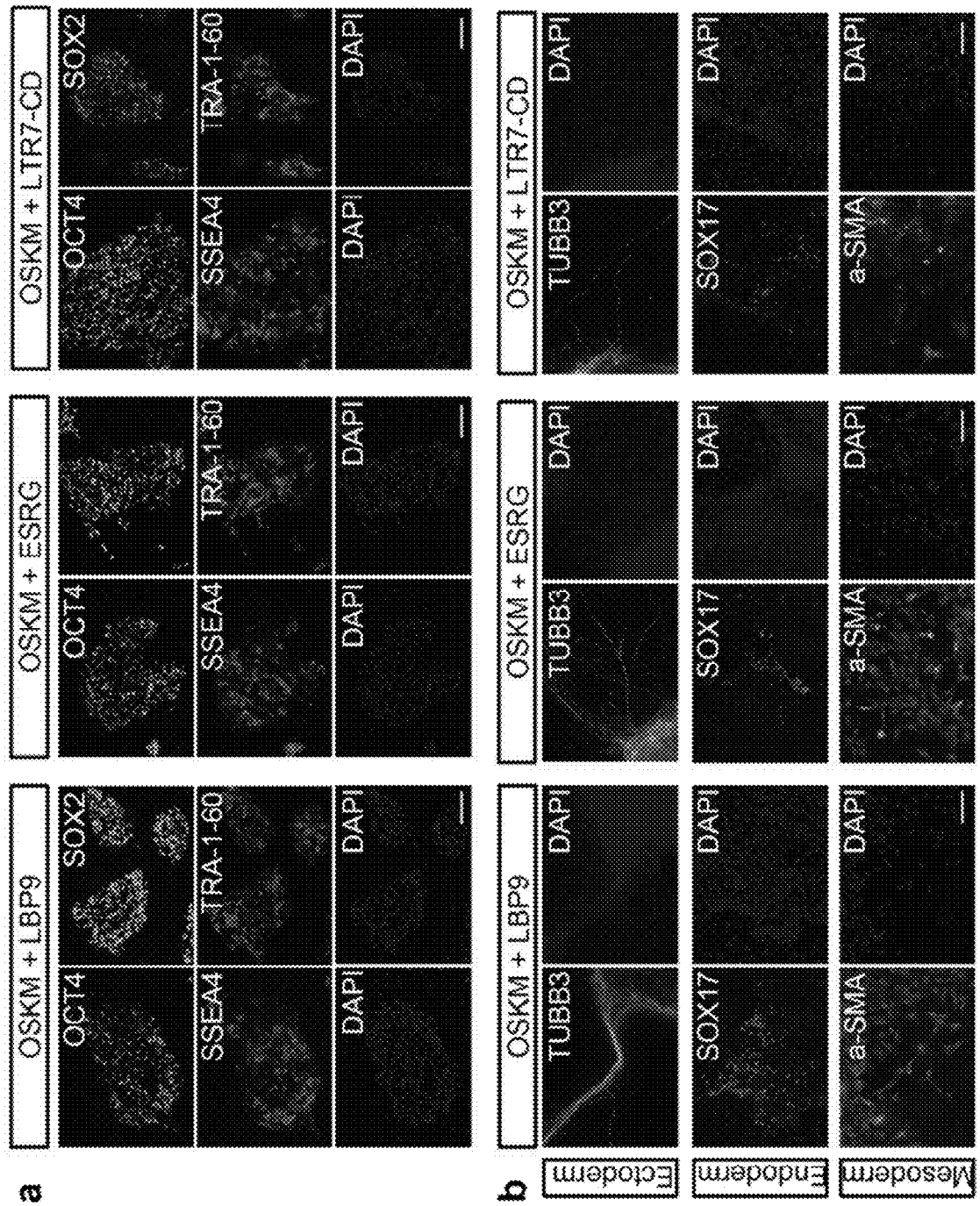
Figure 9:
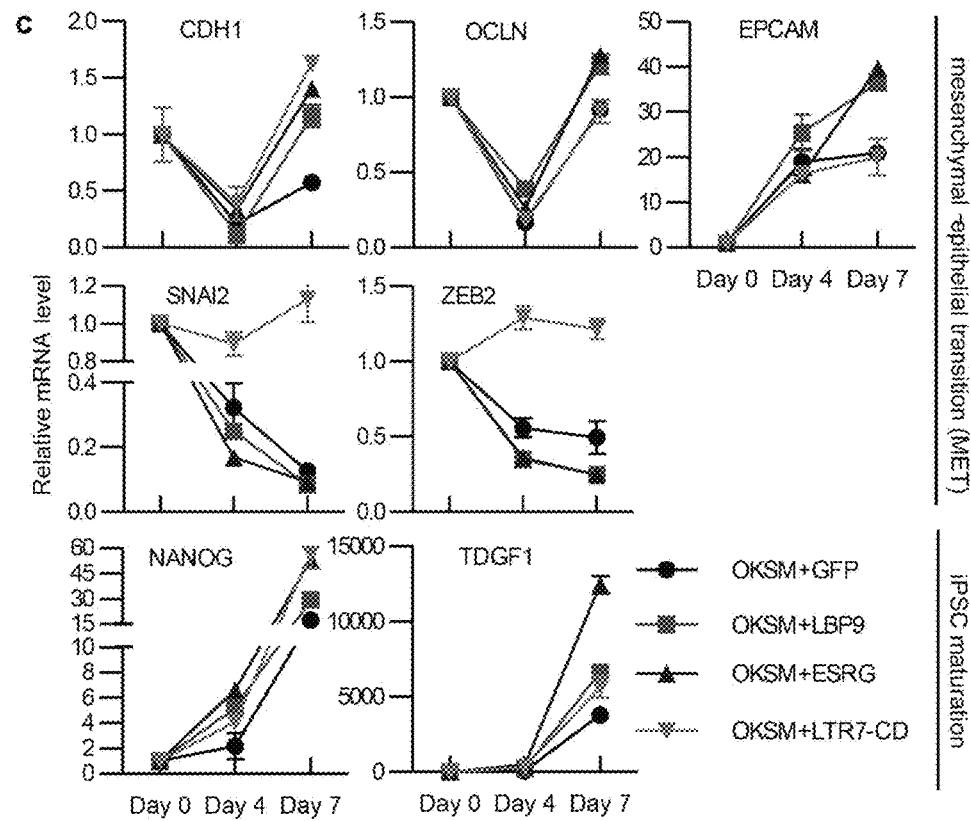
Figure 9:
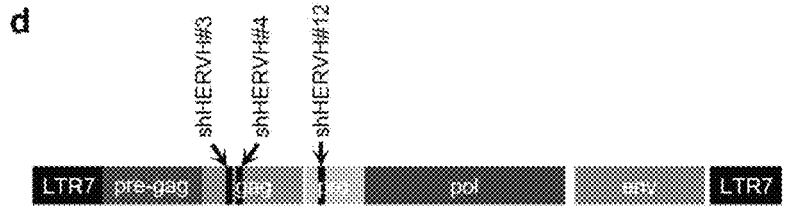
Figure 9:
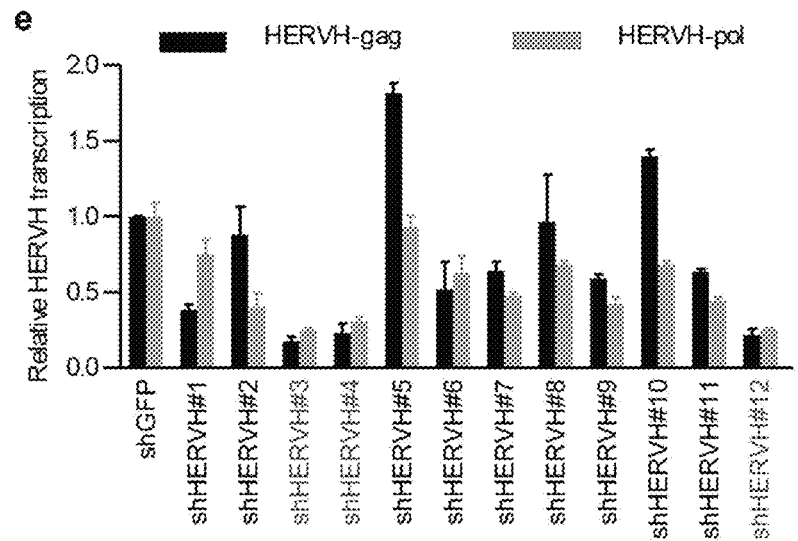
Figure 9:
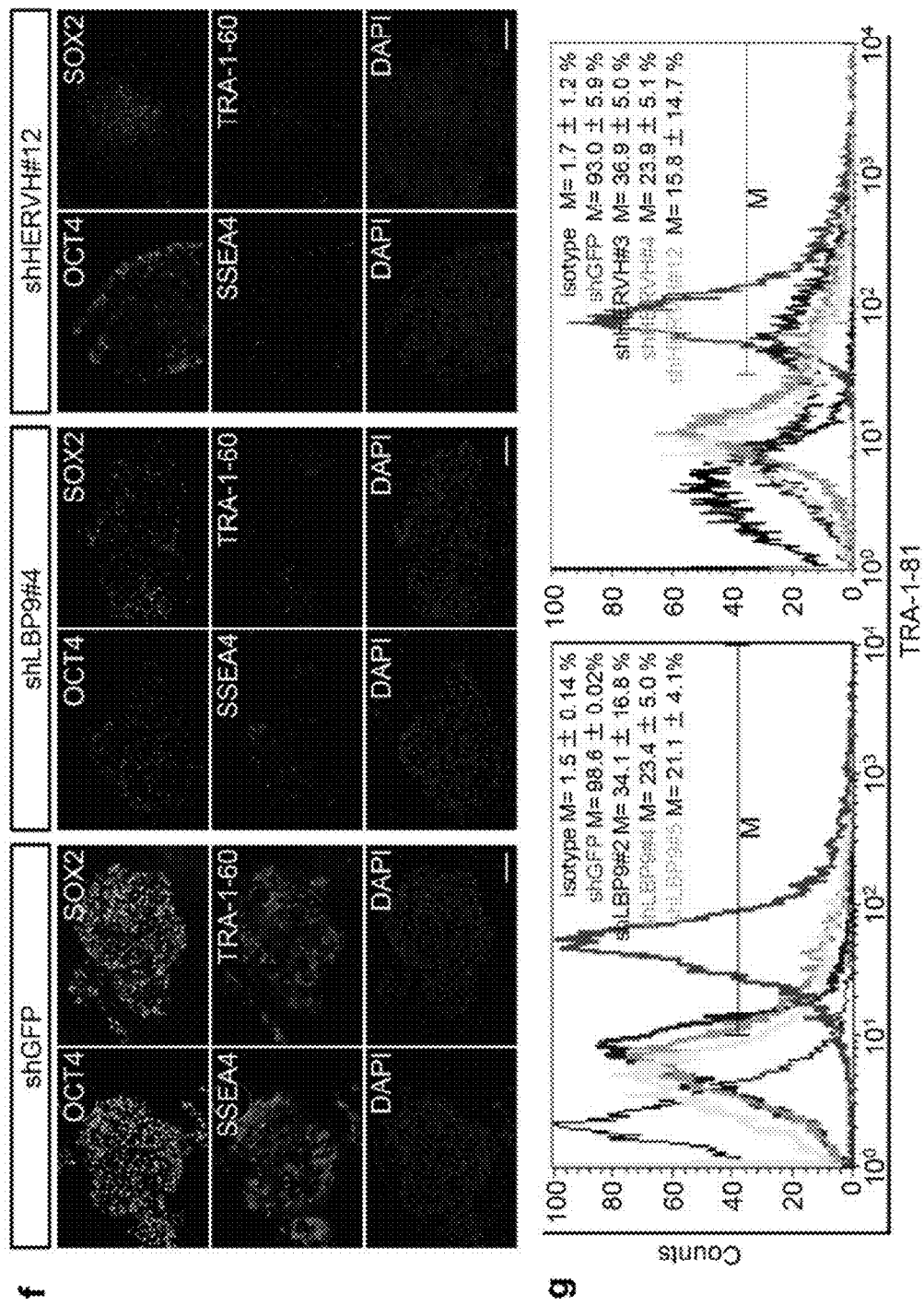
Figure 9:
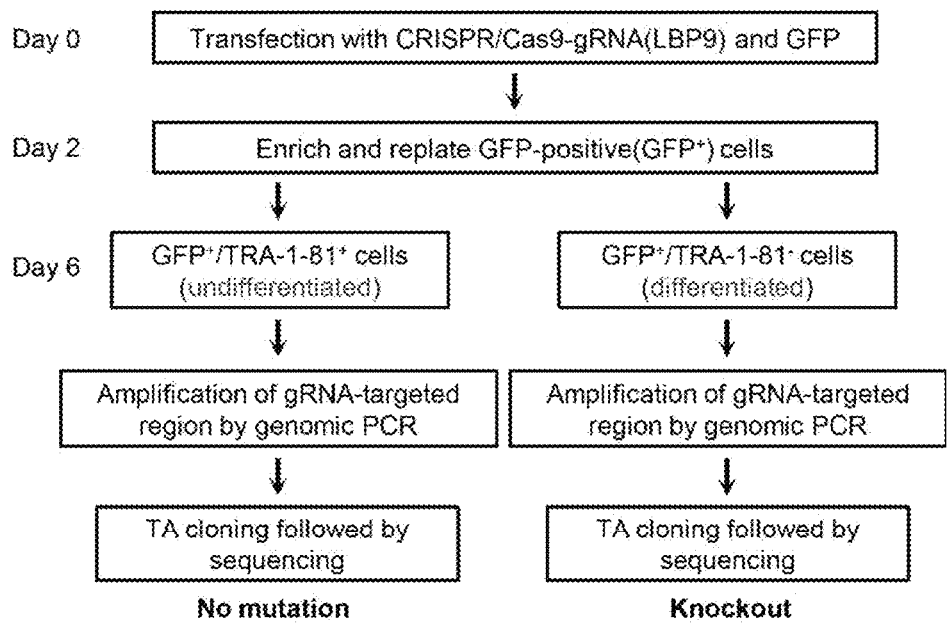
Figure 9:
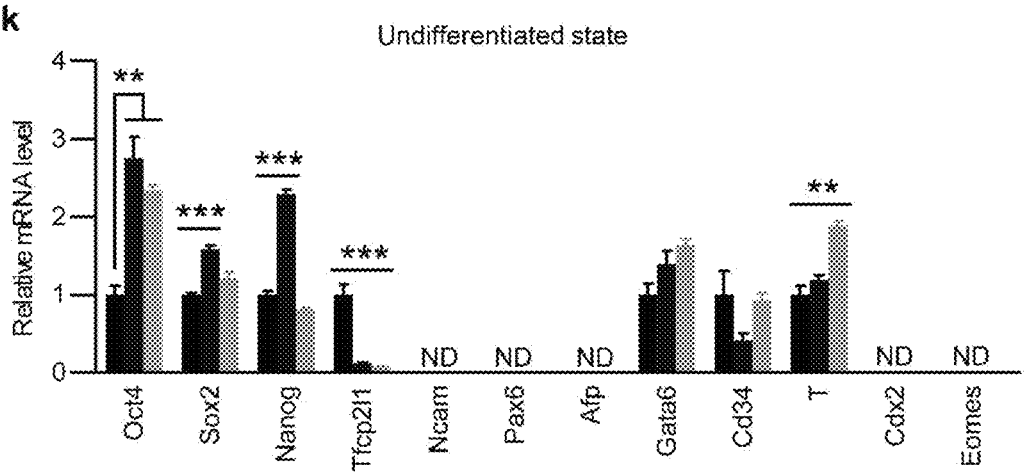

FIG. 9. LBP9/HERVH-driven transcription regulates pluripotency in hPSCs a-b, Characterization of hiPSC lines induced by OSKM+LBP9, OSKM+ESRG and OSKM+LTR7-CD by immunostaining (scale bar 100 µm). a, Immunostaining for pluripotency markers. b, hiPSCs induced by OSKM+LBP9, OSKM+ESRG and OSKM+LTR7-CD can be differentiated into three germ layer lineages in vitro. c, Relative expression values of reprogramming-associated genes in HFF-1 are shown at different time points (RT-qPCR). Data normalized to GAPDH, and relative to day 0. Error bars indicate s.d. (n=3 independent experiments with biological triplicates per experiment). d, Schematic representation of the regions of HERVH targeted by shRNA constructs, shHERVH #3, #4 and #12. Predicted direct targets of shRNAs are shown in Table S14. e, Validation of the shHERVH constructs. Stable, G418-resistant hESCs-derived colonies express various shRNA constructs, targeting HERVH. Knockdown effect was monitored by qRT-PCR detecting either HERVH-gag or HERVH-pol levels. Data shown are representative of two independent experiments with biological triplicates per experiment. shHERV #3, #4 and #12 knocked-down ~80% of HERVH compared to the control shGFP. shHERVH #3, #4 and #12 (all shown in red) are also used in experiments presented on FIG. 3c-f. f, Representative immunostaining images showing reduction of pluripotency markers (OCT4, SOX2, SSEA4, and TRA-1-60) in both LBP9 and HERVH-depleted hESC_H9s. shRNA against the GFP gene was used as the control (shGFP). Scale bar, 100 µm: g, FACS analysis to determine the percentage of TRA-1-81+ cells after depletion of LBP9 or HERVH. Three different shRNAs were employed to independently target LBP9 and HERVH, respectively. Data are presented as mean and s.d. (n=3 independent experiments with biological triplicates per experiment). h-j, Knockout of LBP9 in hESCs by the CRISPR/Cas9 technology. h, Experimental scheme to knockout LBP9 in hESCs using two guide RNAs (gRNAs), both targeting the second exon of LBP9. i, Analysis of LBP9 mutant hESC clones screened by genomic PCR. j, Sequence analysis of the TRA-1-81 sorted cells show that LBP9 mutants are found in differentiated (TRA-1-81-) but not in undifferentiated (TRA-1-81+) hESCs (representative samples). k, In contrast to human, Tfcp2l1 (mouse LBP9) depletion by shRNA does not affect self-renewal (left panel) in mouse ESCs in LIF/serum condition. Tfcp2l1-depleted mESCs were then differentiated into embryoid bodies (right panel), and endoderm and mesoderm markers were more expressed compared with shGFP mESC-derived embryoid bodies, indicating that Tfcp2l1-depleted mESCs have a bias to differentiate to endoderm and mesoderm (qRT-PCR analyses). Data are normalized to GAPDH, and relative to shGFP expressing, undifferentiated mESCs. Error bars indicate s.d. ND indicates undetectable. *P<0.05, P<0.01, *P<0.001; t-test (n=3 independent experiments with biological triplicates per experiment).

Figure 10:
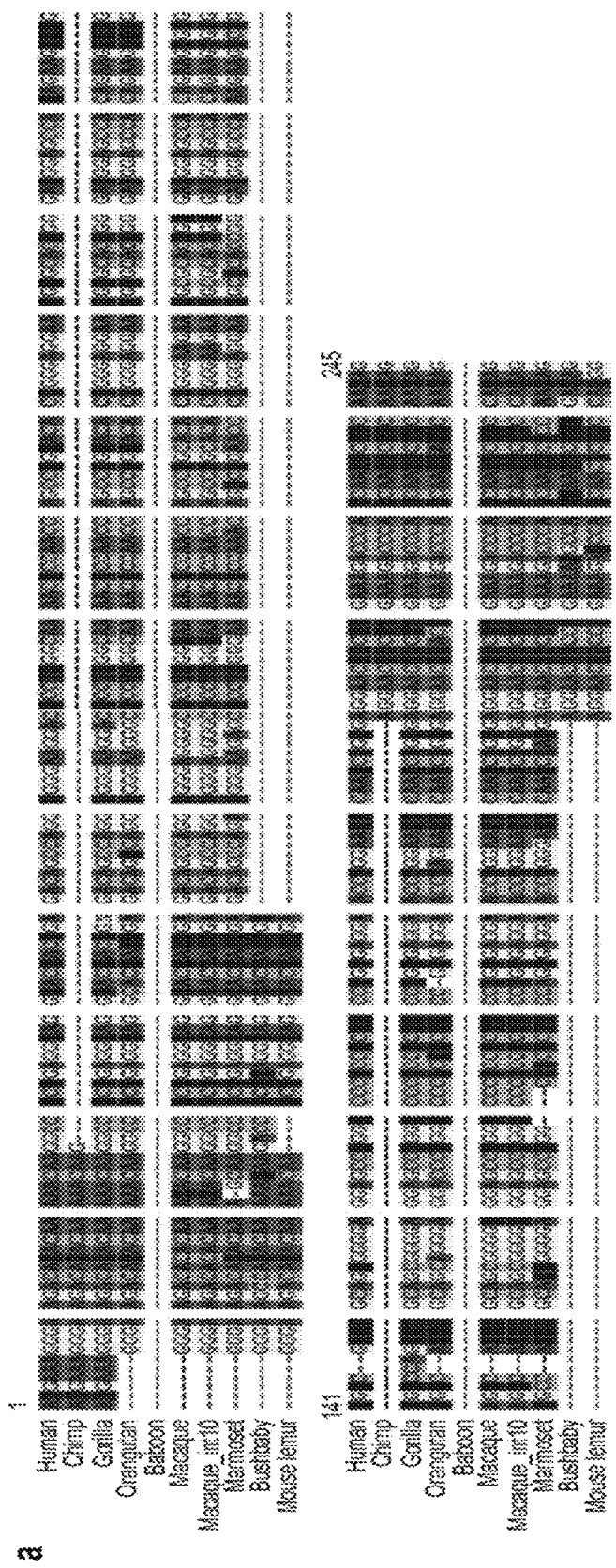
Figure 10:
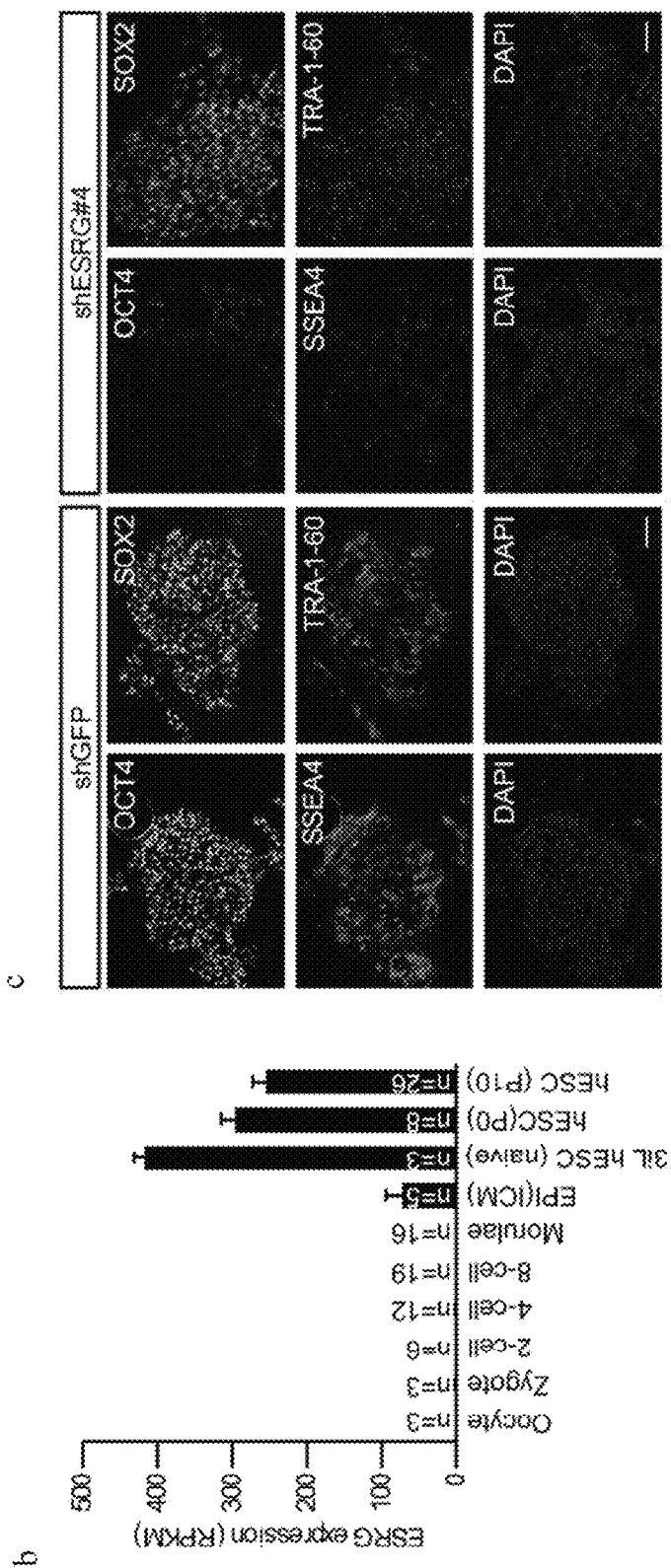
Figure 10:
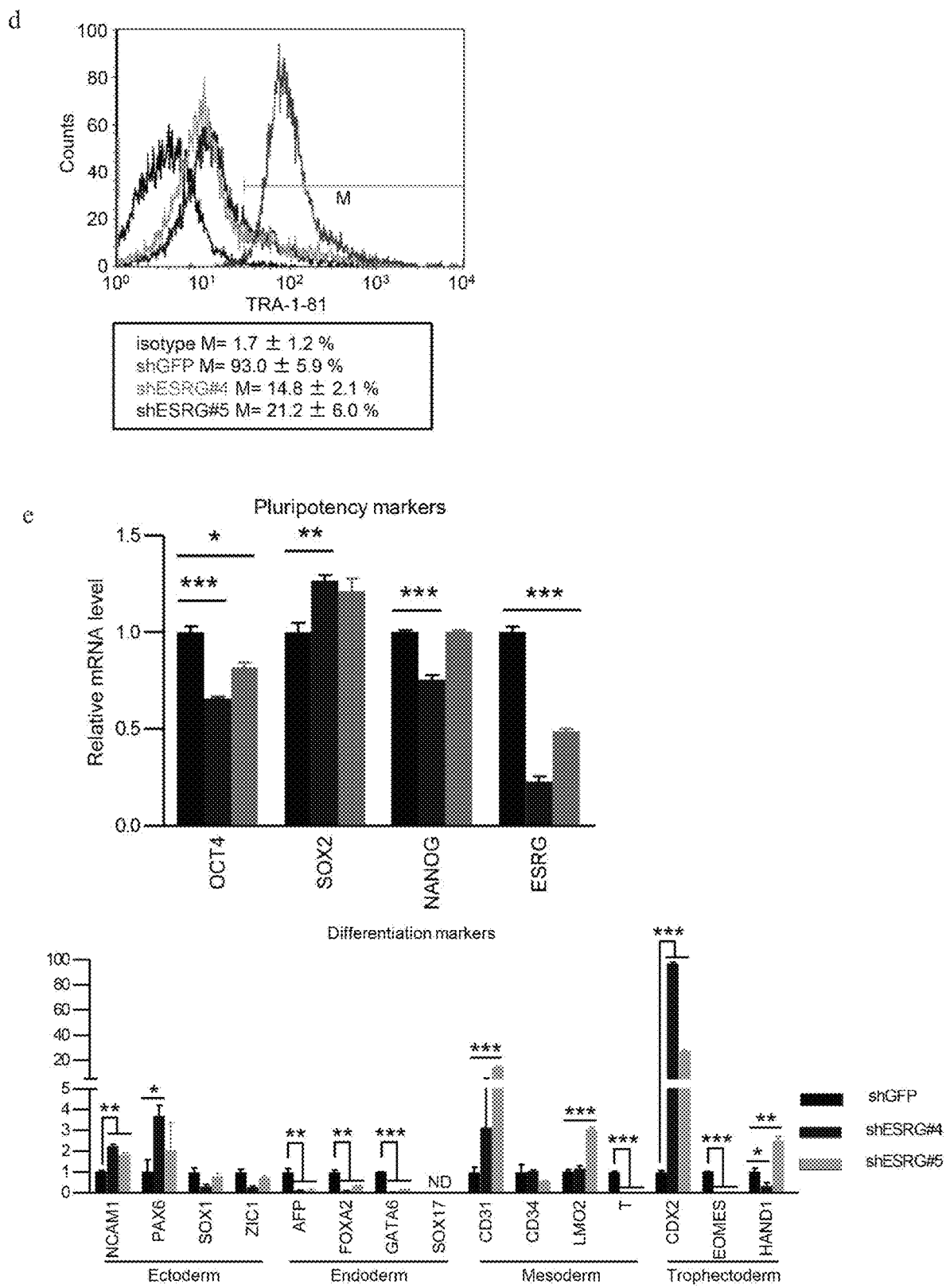
Figure 10:
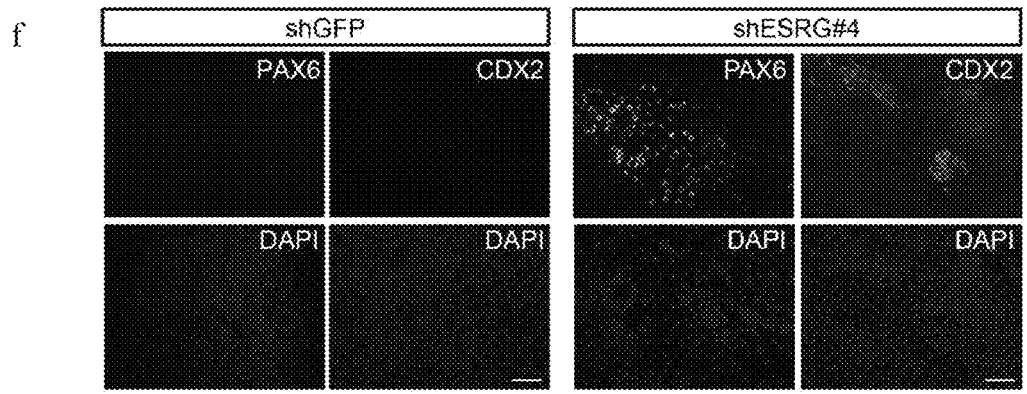

FIG. 10. ESRG is required for maintenance of human pluripotency.

a, Multi-alignment of ESRG putative open reading frame (ORF) from various primates. The ORF is intact in humans alone. All primate introns are shorter than the human one (which is 142.51 bp). The difference is dominantly accounted for by a single large insertion in the human sequence (circa 2,000-7,500 bp) which comprises the bulk of the ESRG transcript (for alignment see Supplementary Data 1). b, Expression of ESRG during human embryogenesis[24] and in hESC cultures[3] (P, passage number). c-f, Characterization of the effects of ESRG depletion on hESC_H9s. Note that knockdown of ESRG was performed by two different shRNA constructs, #4 and #5, respectively. shRNA against GFP served as a control. c, ESRG depletion compromises hESC self-renewal, indicated by the significant decline of the expression of pluripotency markers, OCT4 and SSEA4. The expression TRA-1-60 was decreased as well, while SOX2 was unaffected. The representative images show immunostaining of pluripotency markers. Scale bar, 100 µm. d, FACS analysis of TRA-1-81 expression in ESRG depleted hESCs by two different shRNA constructs. Data are shown as mean and s.d. (n=3 independent experiments with biological triplicates per experiment). e, qRT-PCR analyses of ESRG knockdowns using selected markers (left, pluripotency; right, differentiation). Commitment to trophectoderm was the most apparent, characterized by the significant change in the expression of CDX2 in the ESRG-depleted cells. Data, representative of three independent experiments with biological triplicates per experiment, are normalized to GAPDH, and relative to shGFP expressing, undifferentiated hESCs (hESC_H9s). Mean and s.d.; *P<0.05, P<0.01, *P<0.001; t-test. f, Representative images of immunostaining showing expression of PAX6 (neuroectoderm) and CDX2 (trophectoderm) in ESRG-depleted hESCs_H9. Scale bar, 100 µm.

Figure 11:
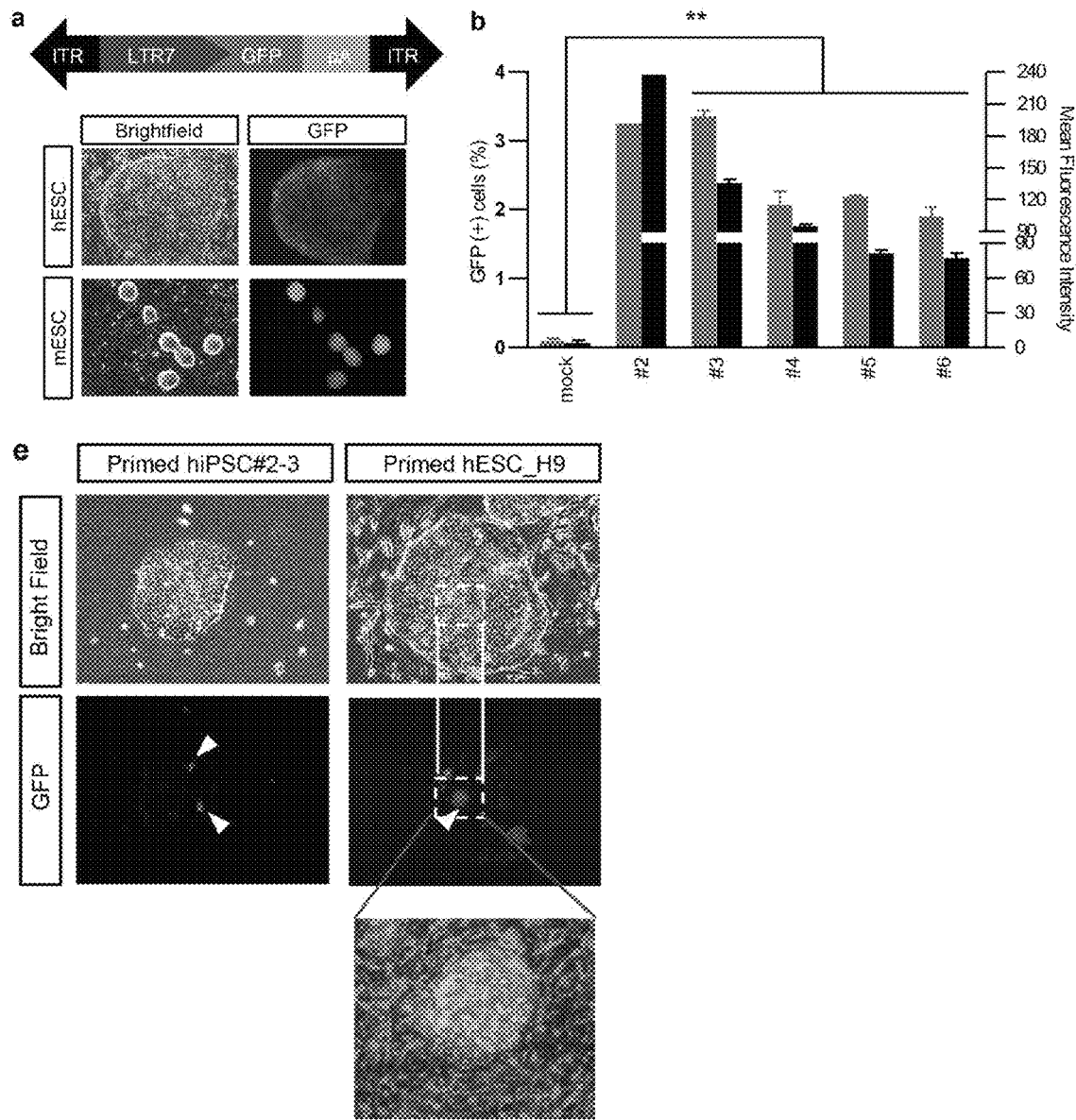
Figure 11:
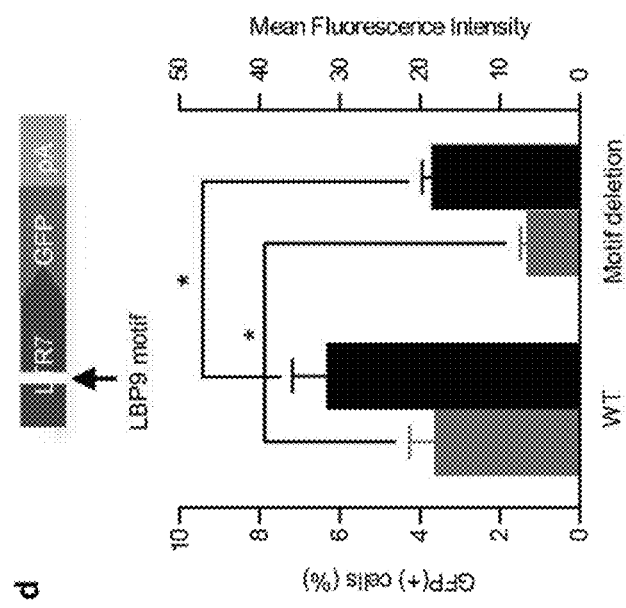
Figure 11:
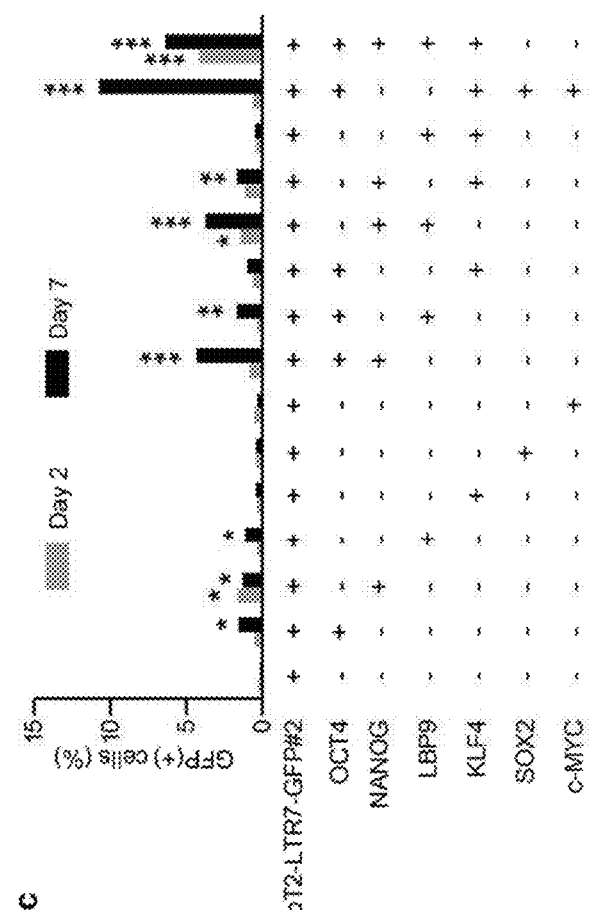
Figure 11:
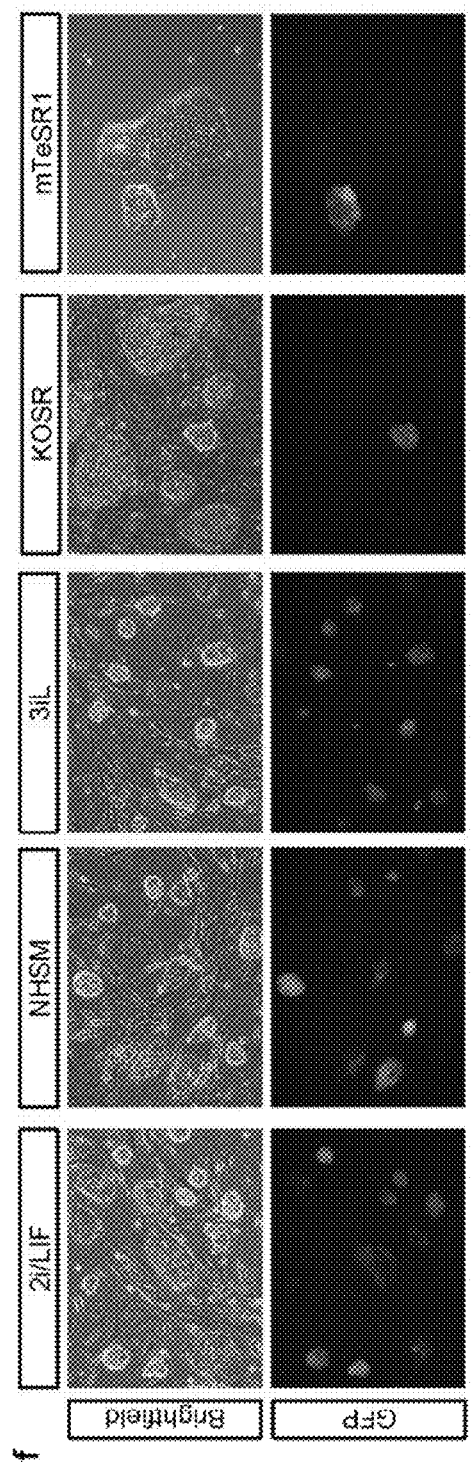
Figure 11:
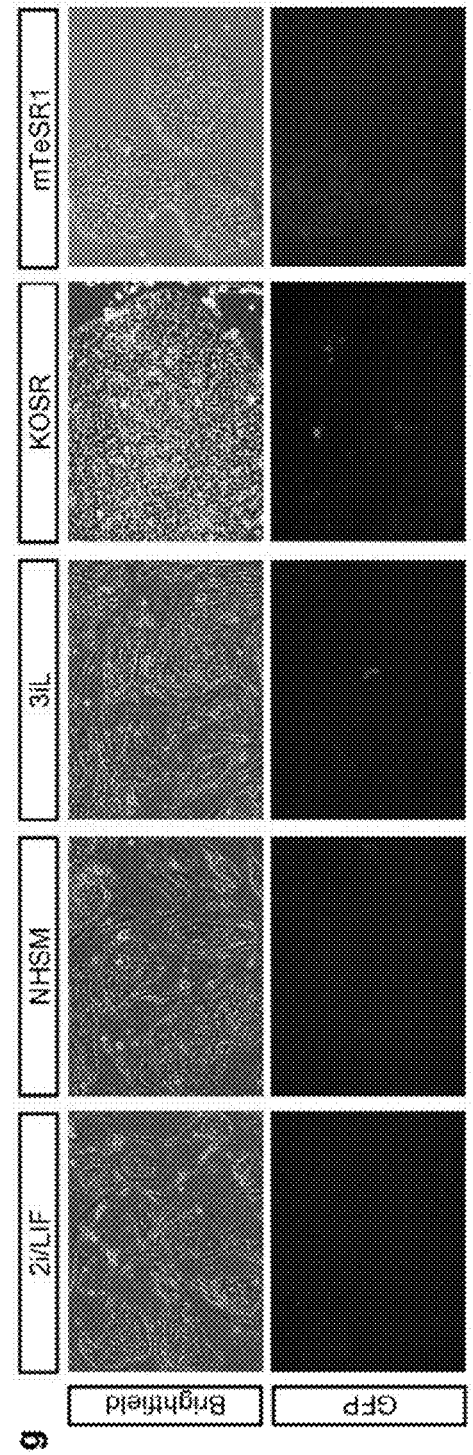
Figure 11:
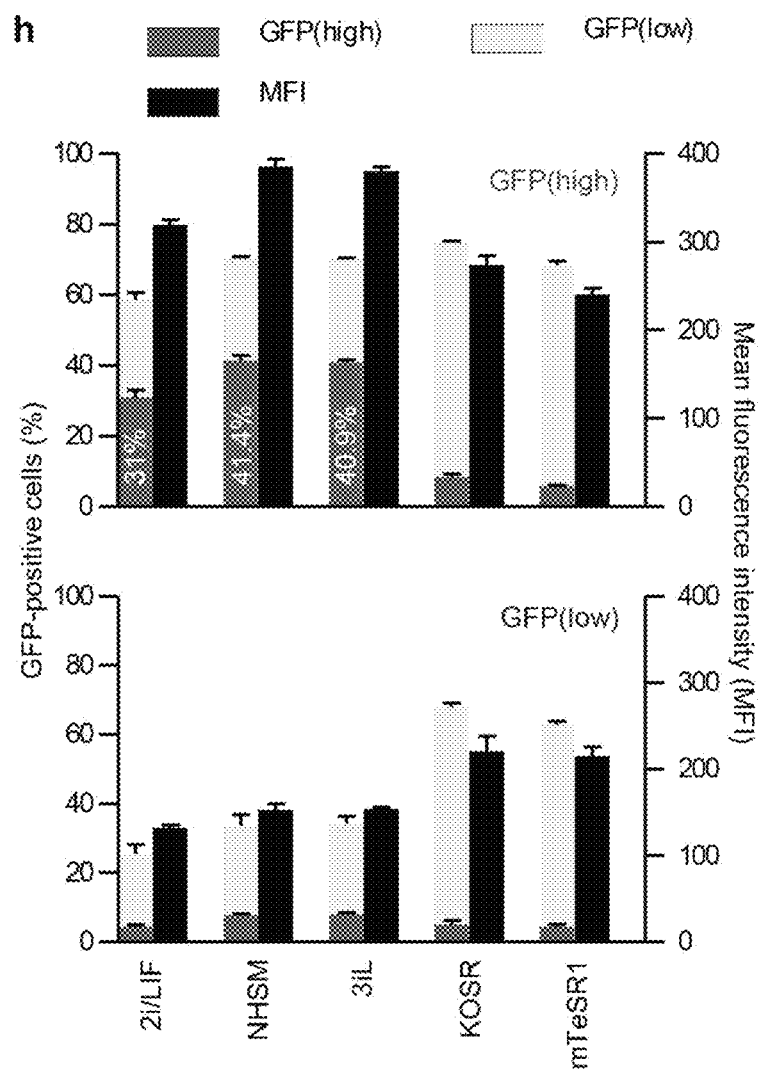
Figure 11:
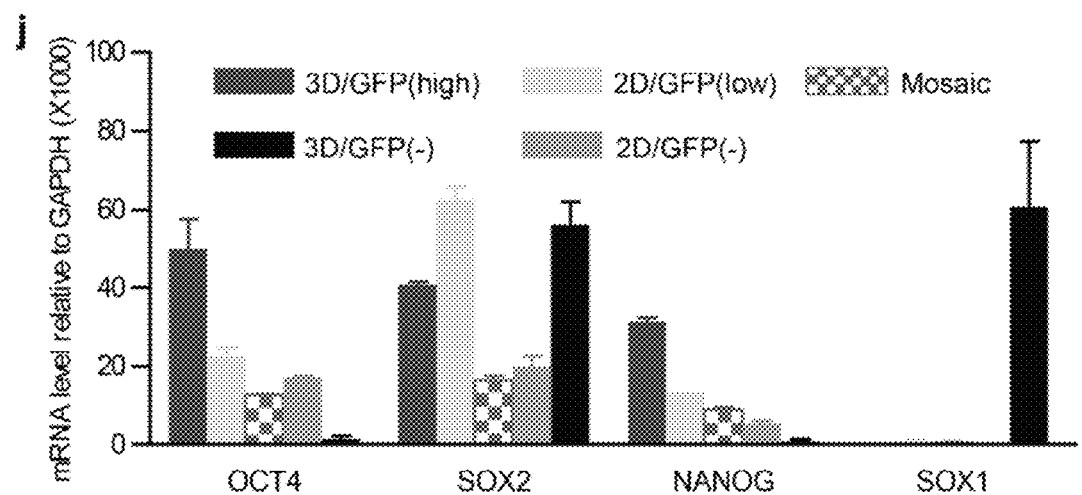

FIG. 11. The reporter assay a, Schematic of the reporter construct, pT2-LTR7-GFP #2 comprising of an LTR7 region amplified from the ESRG locus, fused to GFP-polyA, and flanked by inverted terminal repeats (ITRs) of the SB transposon-based integration vector[22]. A reporter line was established by co-transfecting pT2-LTR7-GFP #2 with SB100X into HFF-1. GFP signal is detectable in both mouse and human transgenic ESCs. Representative pictures of pT2-LTR7-GFP #2-marked hESC_H9s and mESCs are shown. In the human case we show a FACS sorted single colony. In mouse, as all cells express, we show multiple unsorted colonies. b, Multiple LTR7s responding to the fibroblast-iPSC transition are capable of driving the GFP reporter. Compared to the positive control #2 (pT2-LTR7-GFP #2), four additional responsive LTR7s (#3-6) amplified from different genomic loci were tested in the reporter assay (transfected into hiPSCs). The GFP signal of the 5 clones correlates to the RPKM values of the RNAseq (not shown). Mock is a negative control transfected with the empty vector (pUC19). Percentage of GFP(+) cells (green) and mean fluorescent intensity (black) are shown. Data were obtained from three independent experiments. Error bars indicate s.d.; **P<0.01, t-test. c, Reporter assays to validate candidate TFs driving transcription from LTR7/HERVH. GFP signal is detectable in the fibroblast-derived reporter line by FACS, following forced expression of NANOG, LBP9, OCT4, KLF4 SOX2 and c-MYC constructs. Quantification was performed at Days 2 and 7 post-transfection. Control was transfected with the empty vector (pUC19). Data were obtained from two independent experiments, *P<0.05, P<0.01, * P<0.001; two way ANOVA followed by Bonferroni test. A synergism between NANOG and LBP9 is indicated. d, Schematic representation of a reporter construct (pT2-LTR7-GFP #1: wild type; WT) and its mutated version, where the LBP9 motif was deleted, were transfected into hiPSCs. FACS quantification of the GFP signal derived from WT and motif-deleted cells. Percentage of GFP(+) cells (green) and mean fluorescent intensity (black) are shown. Data were obtained from three independent experiments. Error bars indicate s.d.; t-test, *P<0.05. e, pT2-LTR7-GFP #2 marked, mosaic, primed hPSC colonies in conventional hESC medium consist of cells expressing HERVH at various levels, but contain GFP(high) cell populations with mESC morphology (indicated by white arrowheads). Representative hiPSC (left panel), hESC_H9 (right panel) colonies are shown. A GFP(high) cell population is magnified. f-h, FACS sorted GFP(high) and GFP(low) hESC_H9 cells were cultured in 2i/LIF, NHSM[4] and 3iL[3] conditions, respectively. f-g, Representative images of GFP(high) and GFP(low) cells cultured in the different conditions at Day 3. f, Morphology and GFP fluorescence of GFP(high), 3D colonies were comparably maintained in the three different naïve culture conditions, but not in primed culture conditions (KOSR and mTeSR1). g, Representative images show flat, GFP-negative colonies derived from GFP(low) hESCs_H9s cultured in either of the different culture conditions. h, Quantification by FACS of GFP-positive cells on Day 6 of culturing in 5 media conditions: 2i/LIF, NHSM[4], 3iL[3], KOSR and mTeSR1. We cultured both GFP(low) and GFp(high) cells prior to sorting. Longer-term culturing of GFP(high) naïve cell is most compatible with 3iL[3] culture condition (not shown). Percentage of GFP(high), GFP(low) cells (bright and pale green) and mean fluorescent intensity (black) are shown. KOSR, knockout serum replacement medium. Error bars, s.d.; n=3 independent cell cultures, representative of two independent experiments. i-j, Heterogeneity of GFP(high) cells cultured in different conditions. i, The percentages of different hESC colonies derived from the same initial GFP (high) population in different culture conditions. 3D/GFP (high), domed colony with strong GFP signal; 2D/GFP (low), flat colony with weak GFP signal; Mosaic, colonies containing, at least two cell types of GFP(high) and either GFP(low) or GFP(−); 3D/GFP(−), domed colony without detectable GFP signal; 2D/GFP(−), flat colony without detectable GFP signal. i, 388-462 colonies were characterised per culture condition, Using fluorescence microscopy. j, qRT-PCR analysis of expression levels of core pluripotency-associated transcription factors in different colony types under the 2i/LIF condition. Total RNA isolated from 10-15 colonies per colony type, was reversely transcribed for qPCR. Error bars indicate s.d. (n=3, technical replicates).

Figure 12:
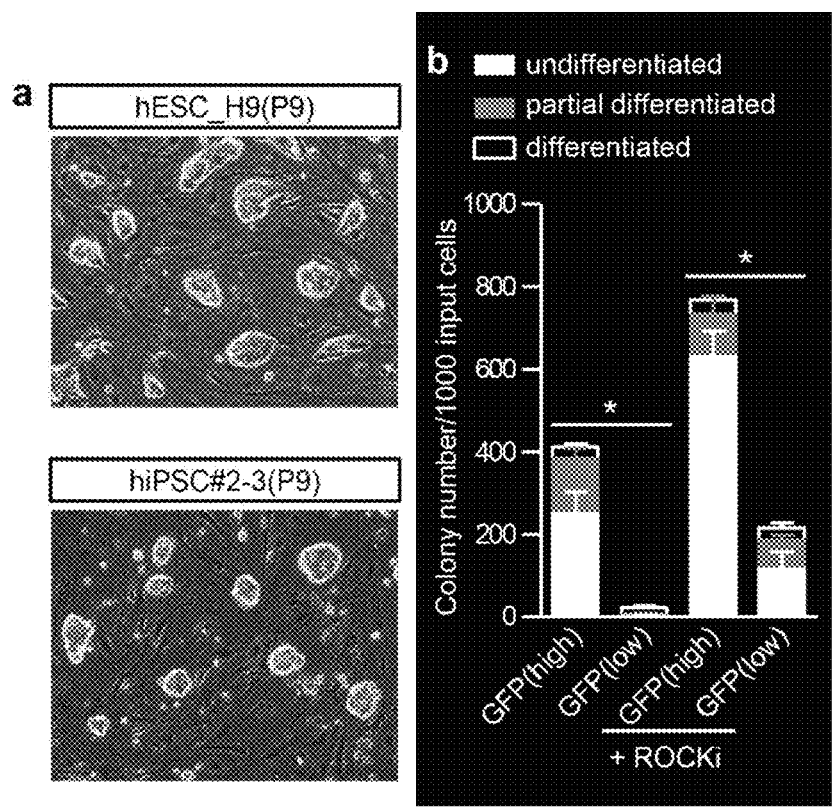
Figure 12:
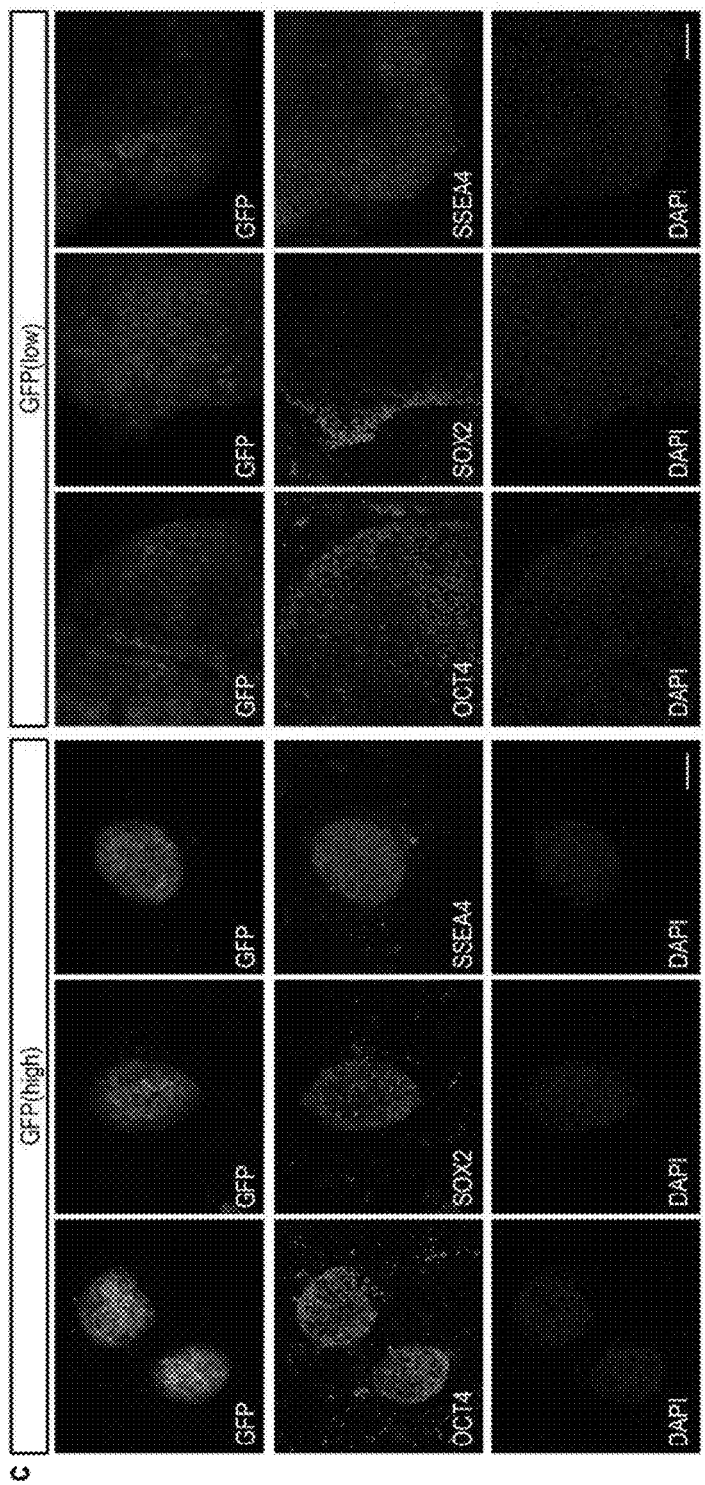
Figure 12:
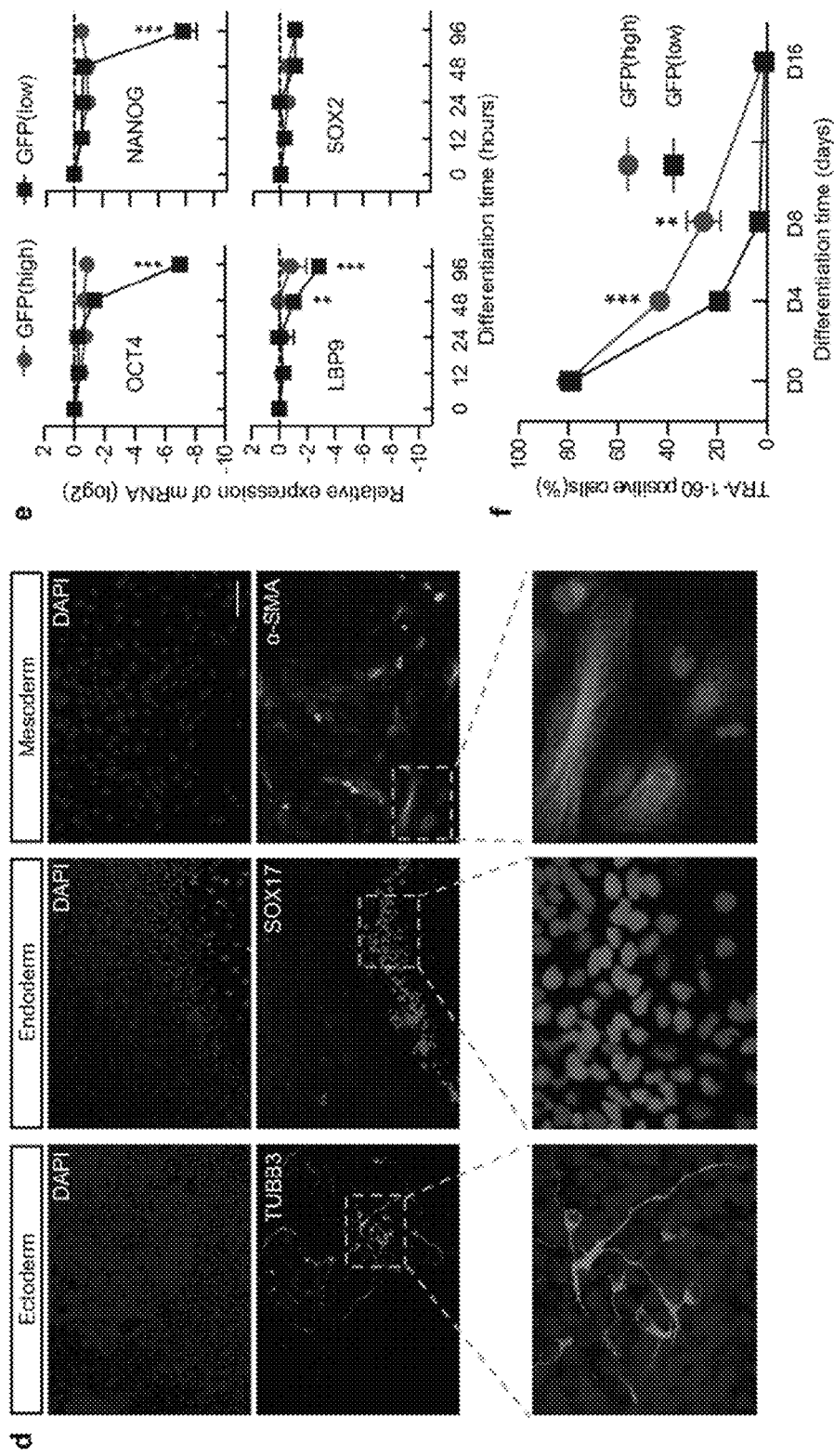
Figure 12:
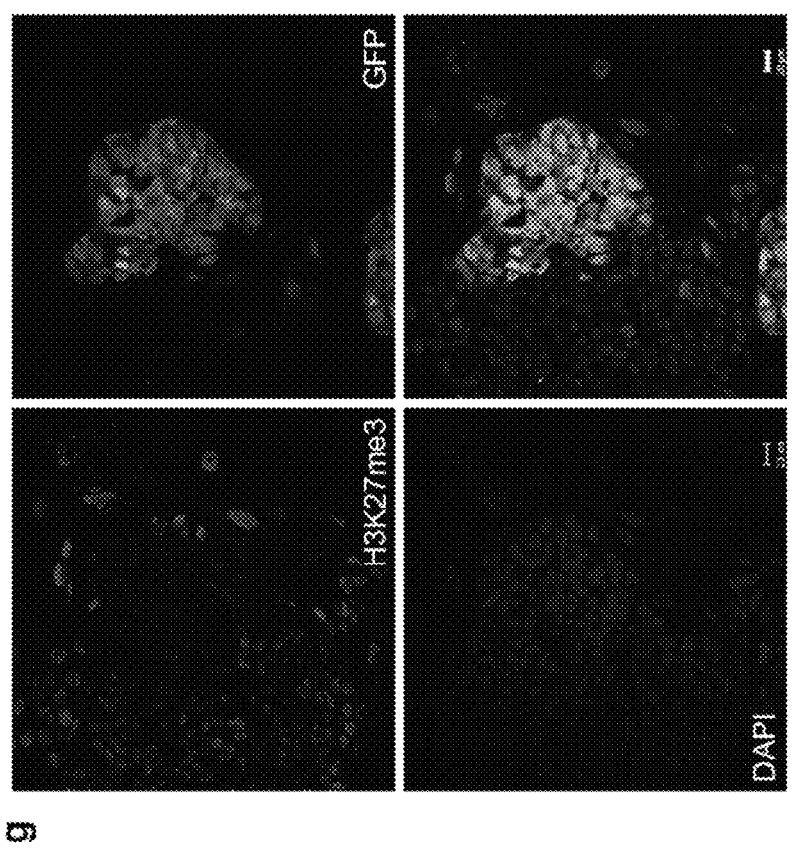
Figure 12:
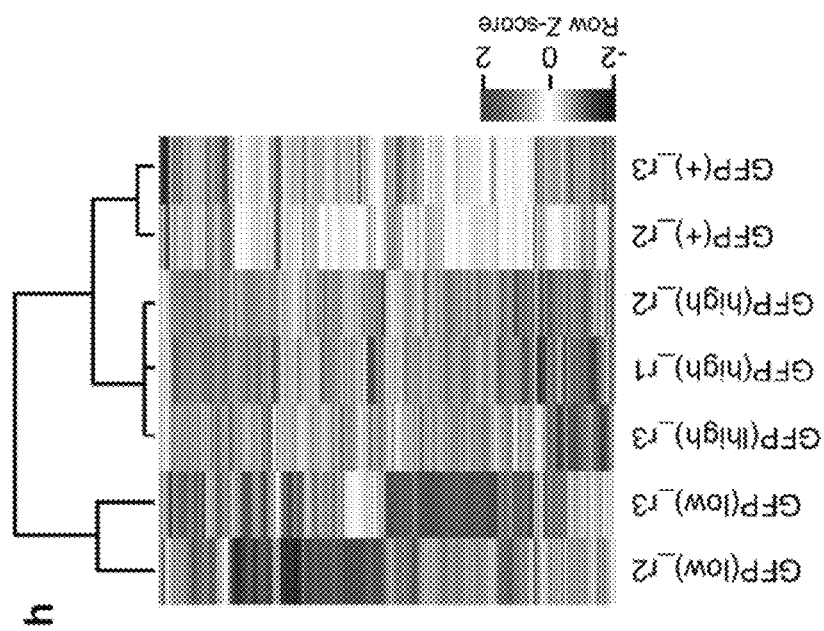

FIG. 12. Characterisation of LTR7-GFP-marked hPSCs a, Genetically labelled (pT2-LTR7-GFP #2) human naïve hESC_H9s and hiPSCs can be maintained in 2i/LIF medium for a longer period of time (followed by passage number=P9, >30 days) by re-plating (every 4-5 days), and by occasional sorting for the GFP marker. For optimal long-term culturing conditions, note also FIG. S7h. b, Single-cell cloning efficiency of GFP(high) vs GFP(low) hESCs_H9s. ALP-stained colonies were counted one week after plating 1,000 cells of a single cell suspension [with or without ROCK inhibitor (ROCKi)]. Data were obtained from three independent experiments. Error bars indicate s.d., *P<0.01, t-test. c, Both GFP(high) and GFP(low) hESCs_H9s are immunostained by the indicated pluripotency markers (OCT4, SOX2, SSEA4). Scale bar, 100 µm. d, GFP(high) cells can be differentiated, and display the markers of the three germ layers. Scale bar, 100 µm. e, qRT-PCR analysis of pluripotency-associated transcription factors during in vitro differentiation of GFP(high) and GFP(low) hESC_H9s. FACS-sorted GFP(high) and GFP (low) cells were cultured in human 2i/LIF medium and in conventional hESC medium for 3 days, respectively before differentiation was triggered. Error bars indicate s.d. (n=3 independent experiments with biological triplicates per experiment), P<0.01, *P<0.001, t-test. f, FACS quantification of TRA-1-60-positive cells in differentiated GFP (high) and GFP(low) cells (statistics as above). Error bars indicate s.d. (n=3 independent experiments with biological triplicates per experiment), t-test for each time point, P<0.01, *P<0.001. g, Representative confocal image obtained after immunostaining for H3K27me3 on a chimeric hESC_H9 colony. GFP(high) cells (green) are marked with lower density of H3K27m3 (red) than GFP(low) and GFP(−) cells, indicating a higher histone methylation status in the absence of GFP Scale bar, 20 µm. h, Global expression comparison between GFP(high), GFP(+) and GFP(low) cells. Hierarchical clustering of the mean expression values of global gene expression using Spearman's correlation (heatmap). Biological replicates are shown. i, Mapping of the integration site of the pT2-LTR7-GFP #2 reporter in GFP(high) cells. The single copy of the reporter is integrated on Chr20 (red box) in a transcriptionally active area, marked by H3K36me3 and H3K79me2. j, Karyotype analysis result indicating the normal karyotype of hESC_H9 which were used in the present study.

Figure 13:
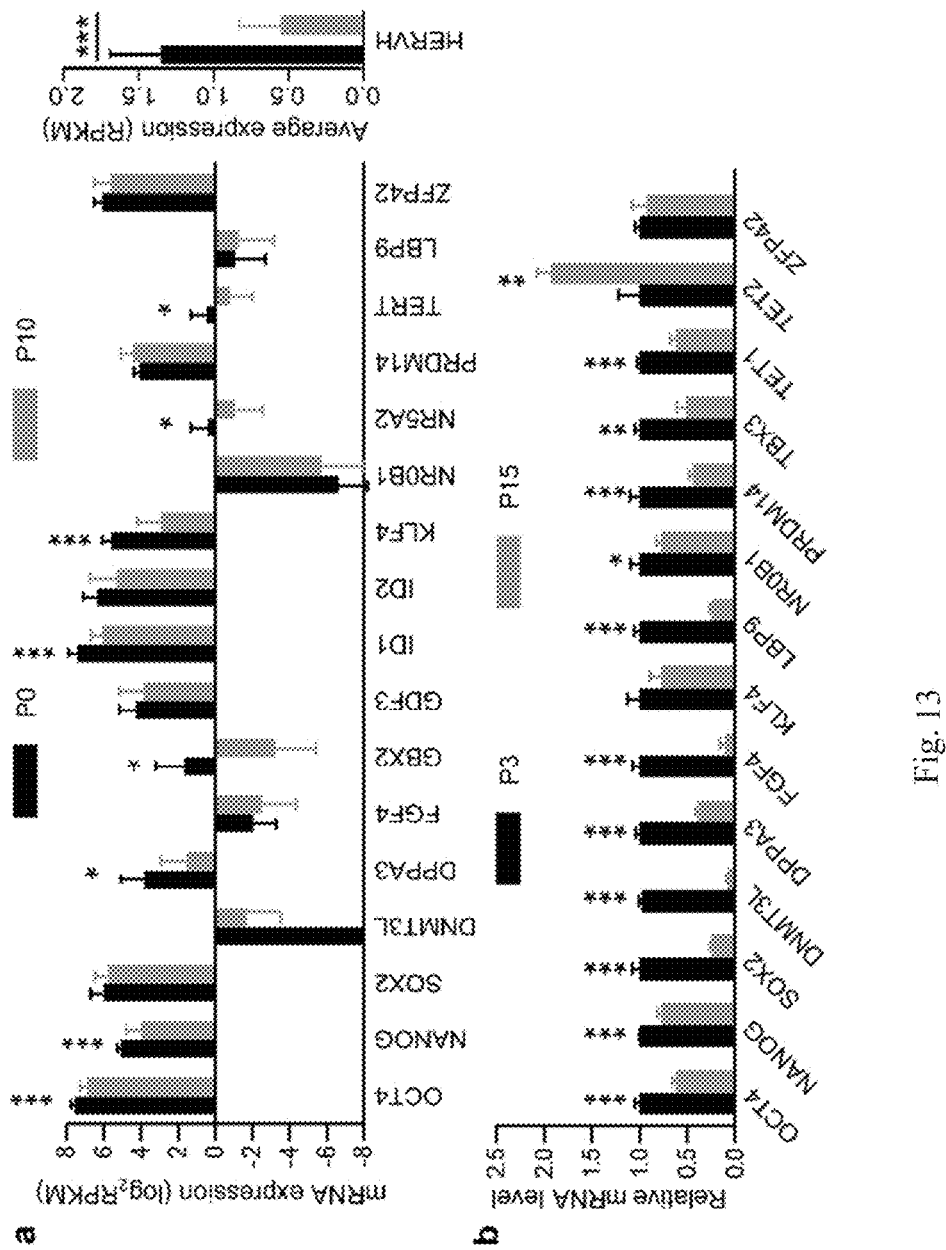
Figure 13:
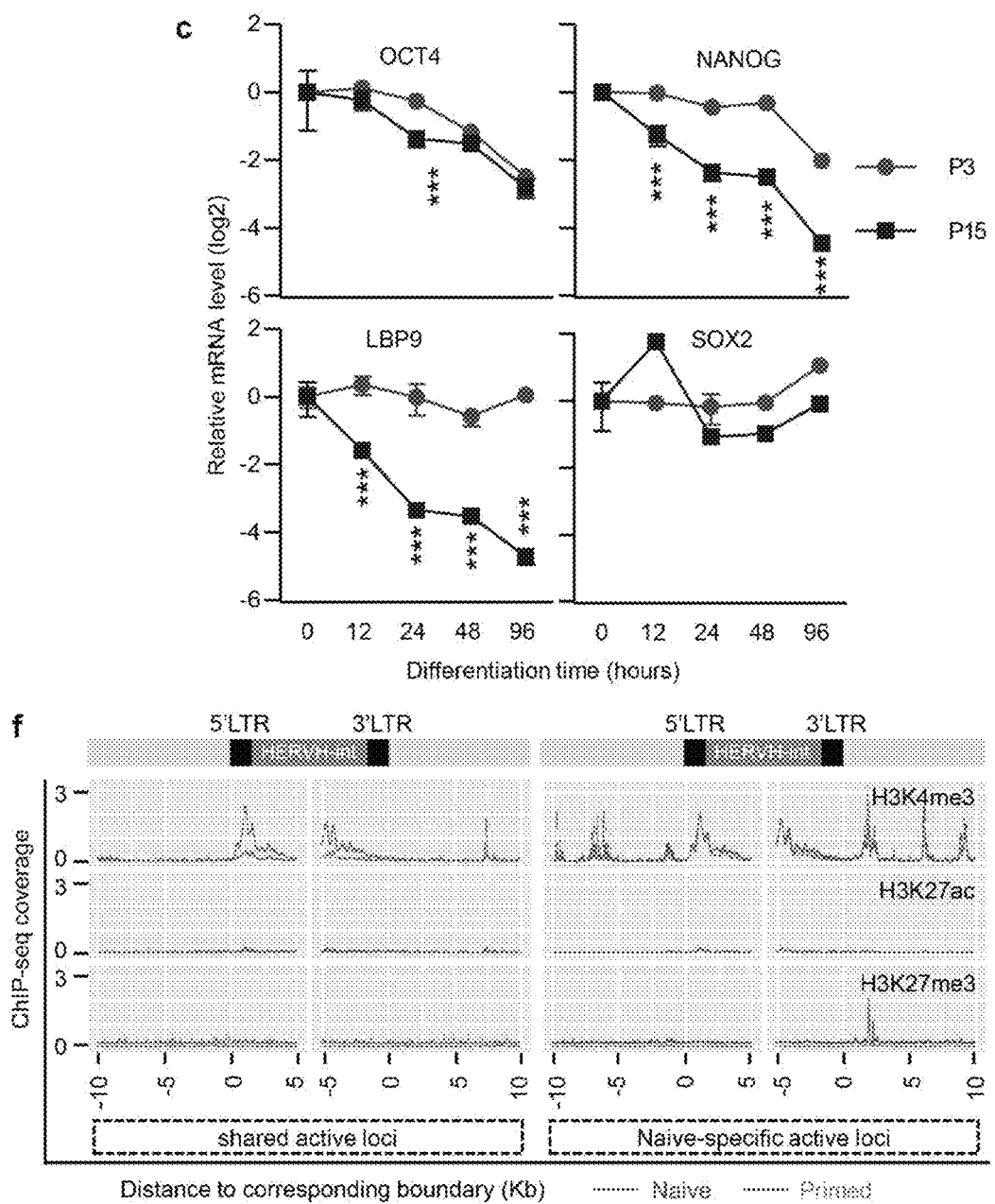
Figure 13:
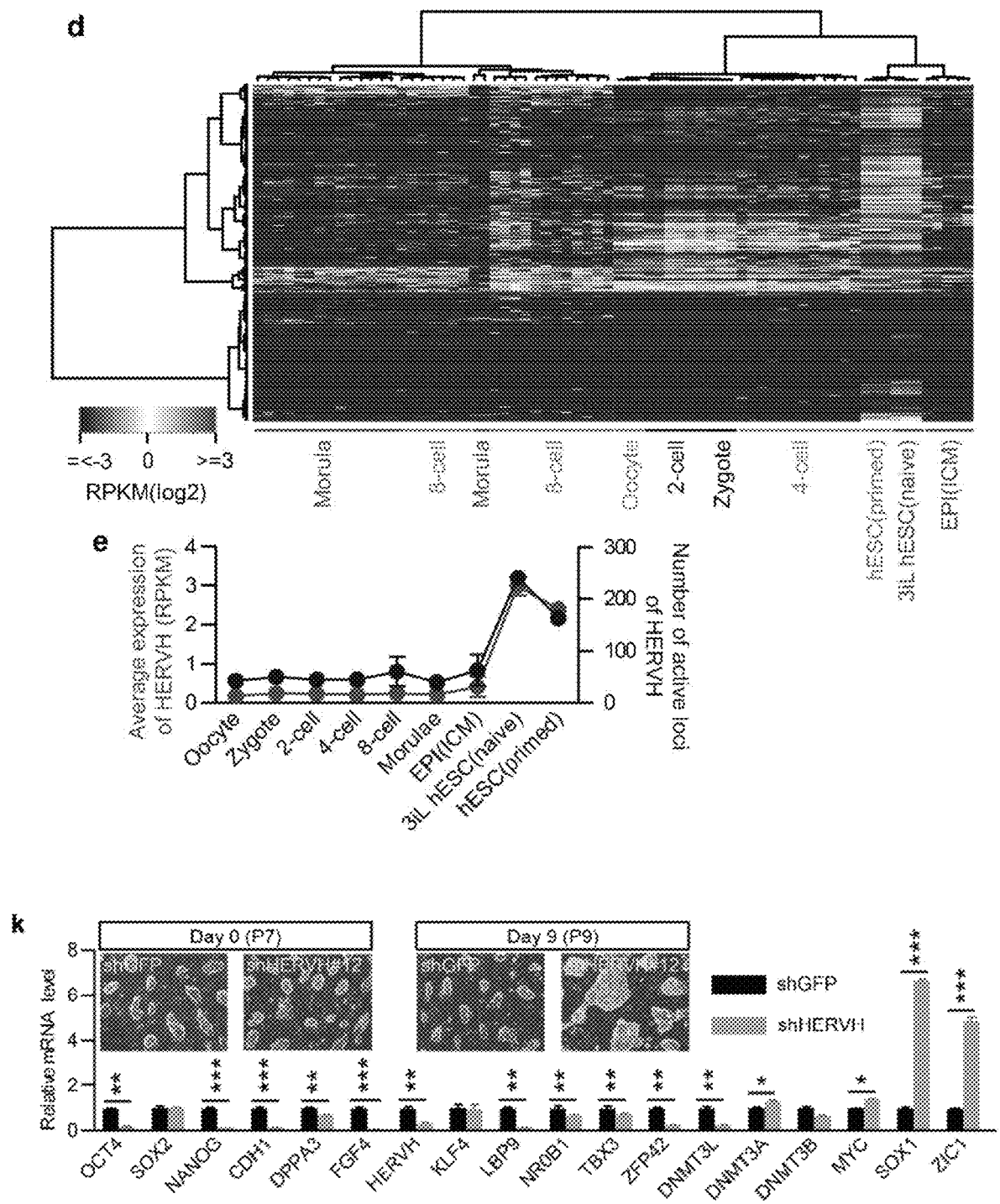
Figure 13:
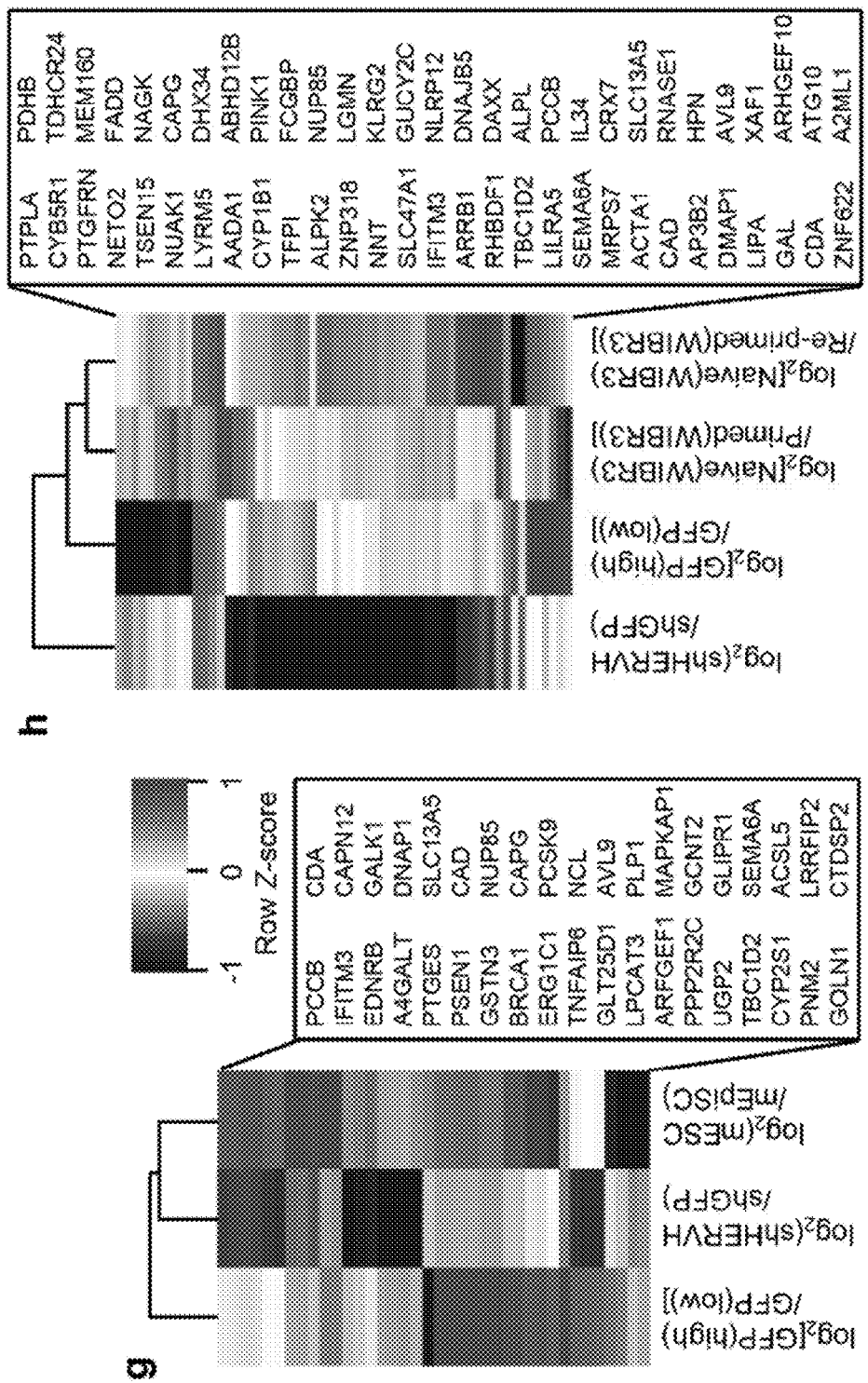
Figure 13:
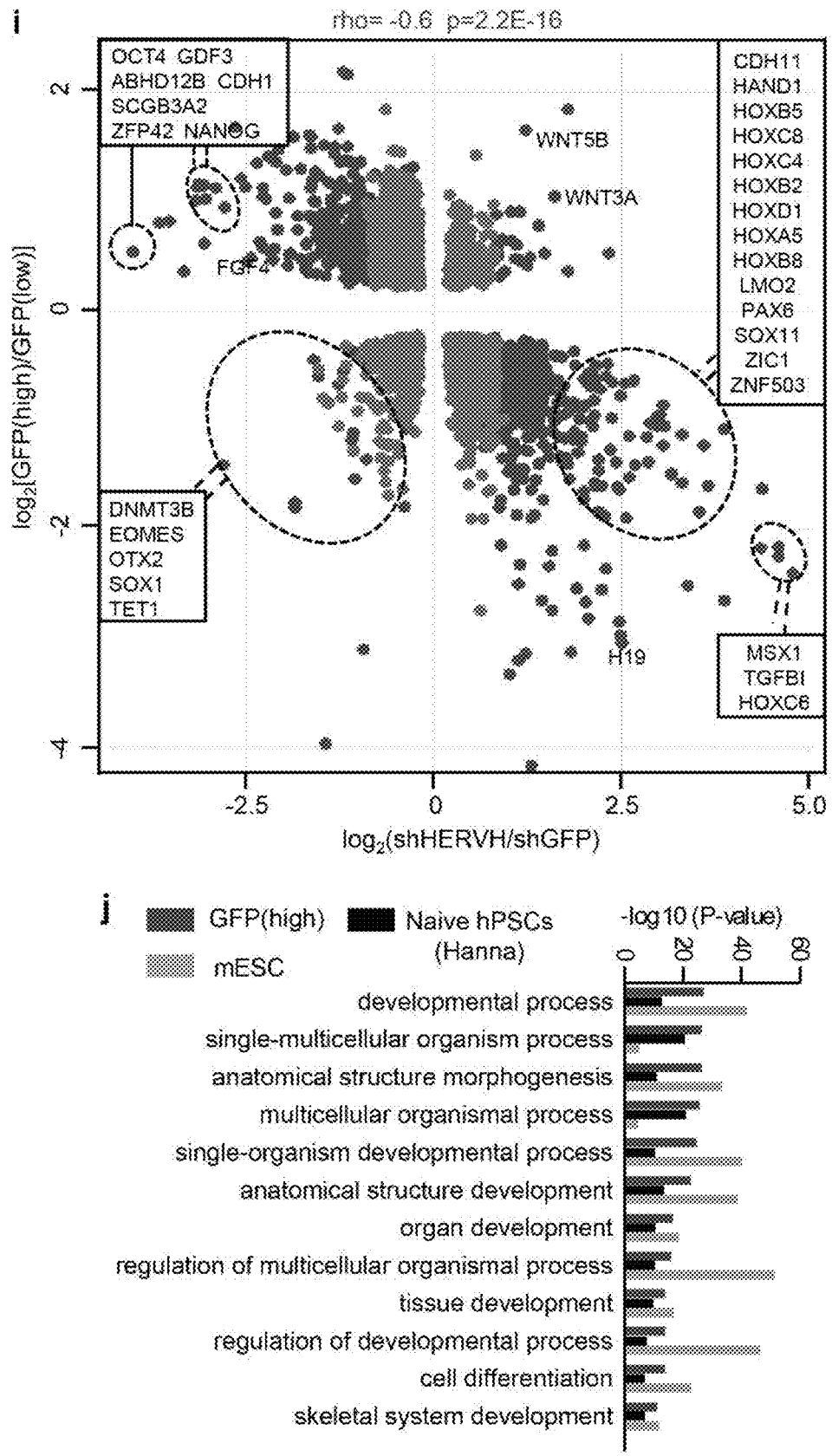

FIG. 13. Transcription driven by HERVH defines naïve-like state of hPSCs a, Expression of pluripotency-associated transcription factors in undifferentiated early (P0) and late passage (P10) hESCs[24]. At P10, n=26, at P0, n=8. t-test, *P<0.05, ***P<0.001. b, qRT-PCR analysis of pluripotency-associated transcription factors in undifferentiated early (P3) and late passage (P15) hiPSCs[30], normalized to levels at P3. c, qRT-PCR analysis of pluripotency-associated transcription factors during in vitro differentiation of early (P3) and late passage (P15) hiPSCs. P, Passage number. t-test within each time period. d, Heatmap showing differential HERVH transcription during human embryogenesis[24] and in cultured hESCs[3]. The raw RNAseq data downloaded from GEO (GSE36552) and ArrayExpress (E-MTAB-2031) were analyzed to monitor HERVH expression. The rows represent the expression of 1225 full-length HERVH loci. e, The average transcription of and number of active HERVHs during human embryogenesis and in cultured hESCs. f, Chromatin status comparison around full-length HERVHs between naive and primed hESC_H1s[3]. While there are no differences in shared HERVH loci, which are transcribed in both naive and primed hESCs, the 5'LTR of naive-specific HERVH loci are marked with H3K4me3. g, Heatmap showing the comparison with mESC versus mouse epiblast stem cells (mEpiSCs[32]) of HERVH neighbor genes. Log 2-fold change values of orthologous genes were subjected to hierarchical clustering (Pearson correlation, centroid linkage, k=3). Genes selected as above, clustering as h. h, The expression of neighboring genes to HERVH in different human cell types, including GFP(high), HERVH-depleted hPSCs, published naïve hPSCs (naïve(WIBR3)) and primed hESCs (reprimed(WIBR3))[4]. The heatmaps shows the comparison of row-normalized differential expression levels at log 2 scale of fold changes of GFP(high) vs GFP(low), shHERVH vs shGFP, Naïve WIBR3 hESC vs primed and re-primed WIBR3 (GSE46872). Genes shown are those differentially expressed within every pairwise comparison (differential expression defined by log 2 modular change>1, with FDR cutoff at 0.01). Isoforms expression merged to single gene. Samples are represented in the order of euclidean distance were clustered using Spearman's correlation and centroid linkage. i, Scatter plot showing the differentially expressed genes between GFP(high) and GFP(low) are negatively correlated with the ones between HERVH-depleted hESCs and WT hESCs. The enlisted genes are enriched in GFP(high) vs GFP(low) are specific to naïve state (upper right), while genes down-regulated by HERVH depletion are specific to primed hESCs or lineage commitment (lower). Red dots indicate differentially expressed genes, which are used for gene ontology analysis (j). Representative cluster are shown. j, Gene ontology (GO) categories for down-regulated genes in GFP(high) compared to GFP(low) as well as naive hPSCs and mESCs vs primed cells[4,32]. k, Depletion of HERVH induced reduction of key transcription factors for naive hPSCs in the 2i/LIF medium. The representative images show the effects on GFP(high) cell morphologies upon depletion of HERVH. Scale bar, 100 µm. mRNA levels are normalized to GAPDH, and relative to shGFP expressing, undifferentiated hESC_H9. In b, c and k, error bars indicate s.d. (n=3 independent experiments with biological triplicates per experiment), t-test, *P<0.05, P<0.01, * P<0.001

Figure 14:
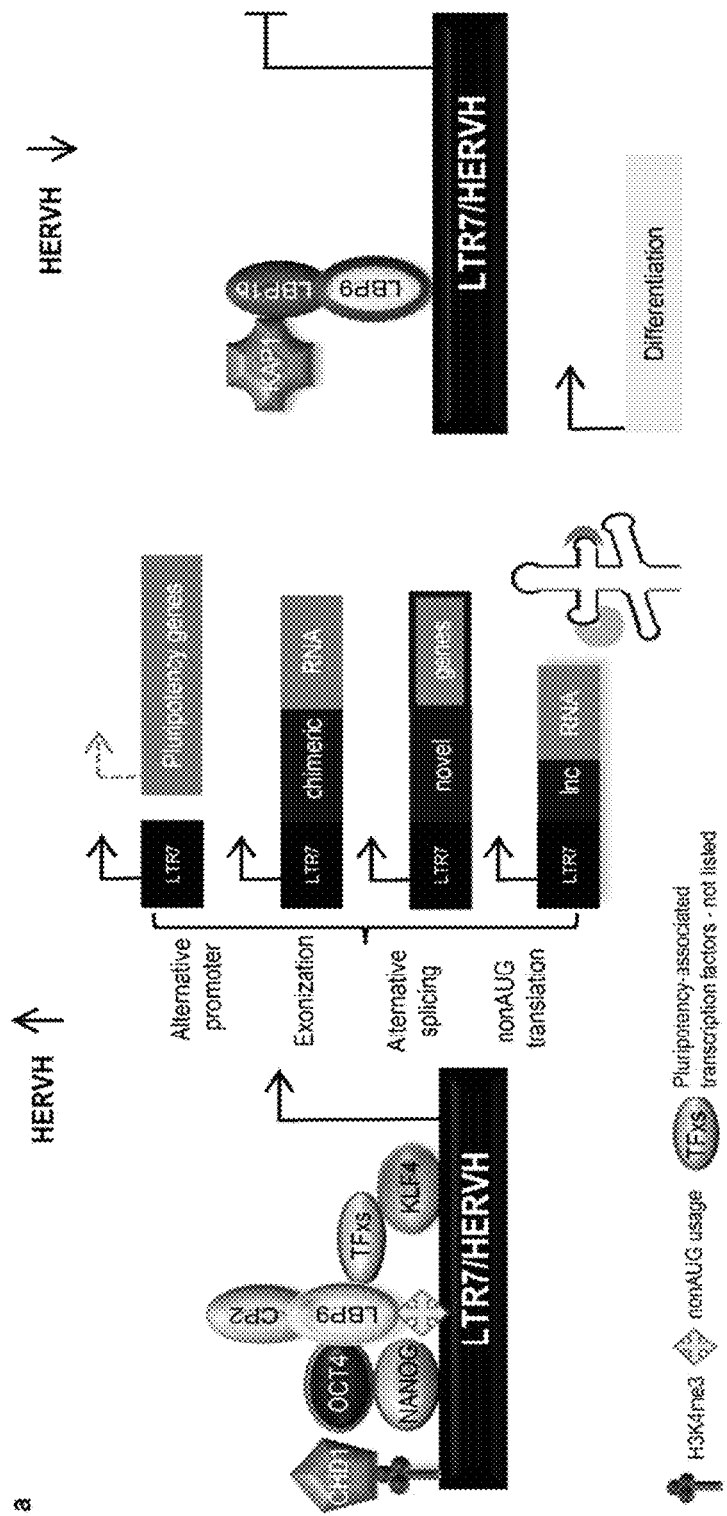
Figure 14:
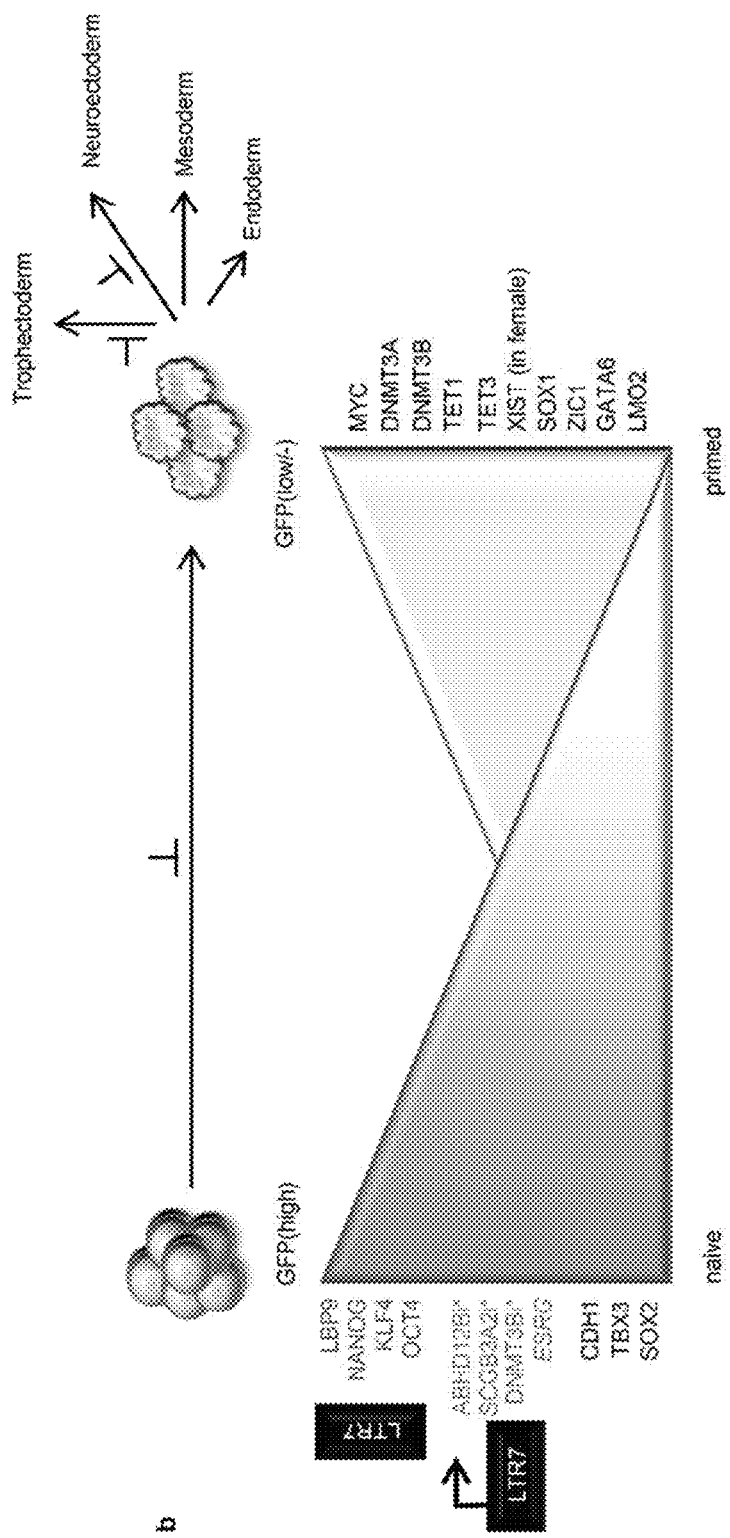

FIG. 14. HERVH drives a primates-specific naive pluripotency: a model a, HERVH clusters naïve TF binding sites. LBP9 is a modulator of the CP2 TF family[28], and can form heteromeric, activator or repressor complexes with other family members, CP2, LBP1 b, respectively. The activator complex interacts with OCT4[16] and promotes pluripotency. In addition we provide evidence for LBP9/NANOG interaction. Activated HERVHs generate numerous novel, stem cell specific alternative gene products. HERVH incorporates a set of regulatory lncRNAs into the network and defines novel pluripotent genes through alternative splicing (in conjunction with CHD1) or alternative nonAUG usage (in conjunction with other members of the CP2 family[33]). LncRNAs, some with a conserved domain (cruciform structure), interact with both pluripotency and chromatin modifying proteins (in green and blue). HERVH inhibits differentiation, while HERVH-derived products contribute to maintain pluripotency. LBP1 b interacts with KRAB-associated protein 1 (KAP1 alias TRIM28), a repressor of ERVs during differentiation[34]. b, GFP(high) cells form dome-shaped (3D), while GFP(low) form flat (2D) colonies. Left: Up-regulated genes in GFP(high) cells include (i) naïve TFs associated with HERVH (brown); (ii) LTR7/HERVH driven novel isoforms of genes (*) and novel genes (e.g. ESRG) (green); (iii) naïve TF factors shared between mice and human (blue); Right: Up-regulated genes in GFP(low) are associated with lineage-commitment.

Figure 15:
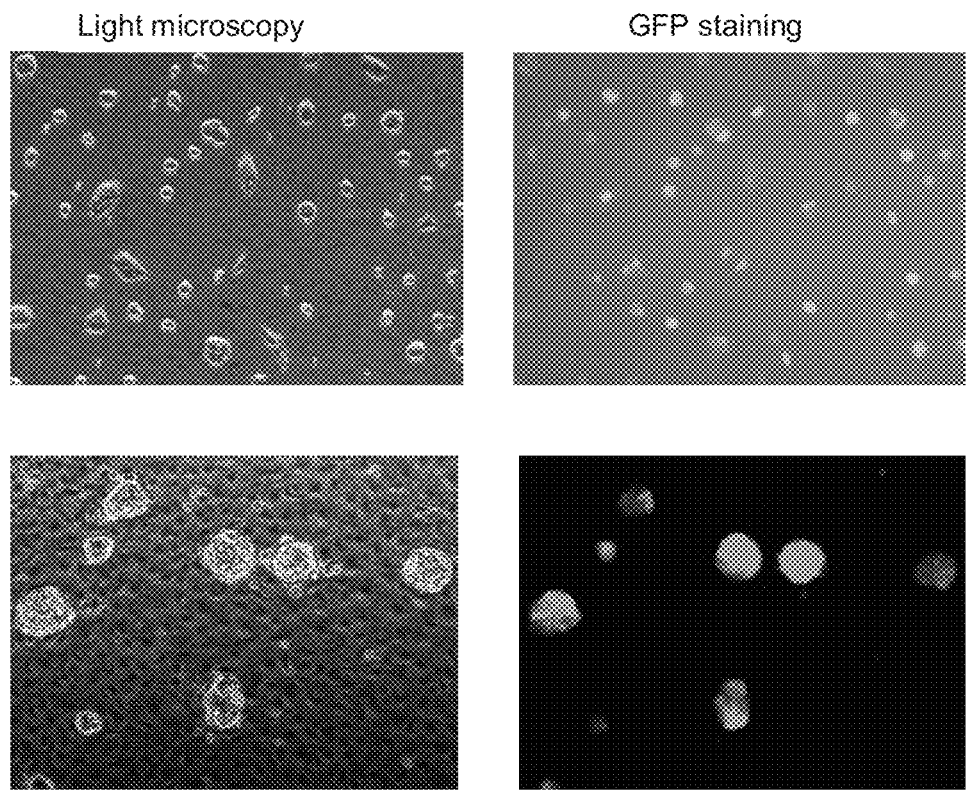

FIG. 15. Microscopic images of naïve PSCs grown in optimized medium

Naïve PSCs were transformed with the LTR7-GFP vector as described herein and cultivated in the 4i medium as described herein. GFP expression and colony formation are shown.

Figure 16:
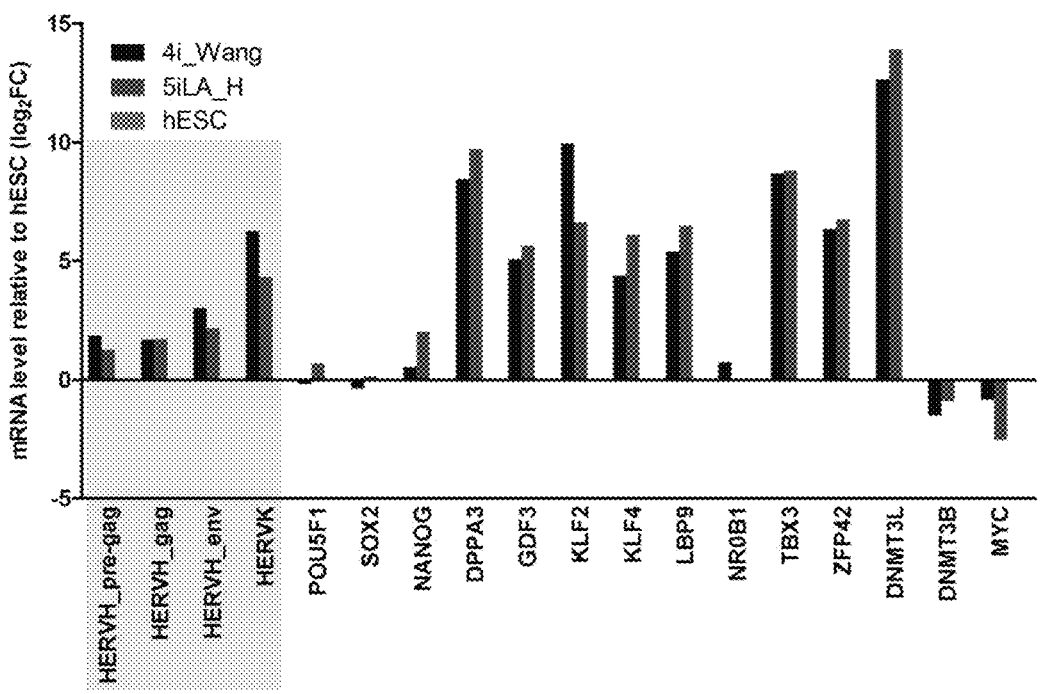

FIG. 16. Comparison in SC marker expression in naïve PSCs grown in various optimized mediums Naïve PSCs were cultivated in the 4i medium as described herein, in addition to the 5i L/A medium as described in Reference 27 (Theunissen et al.), and expression of various SC markers was carried out in a comparative analysis. Expression of LTR7 sequences is shown in the first four transcripts from the left in both culture conditions. The next three markers are indicators for any given kind of pluripotency, whereas the following markers are more specific for naïve stem cells. The last two transcripts (furthest right) are markers for primed cells.

Figure 17:
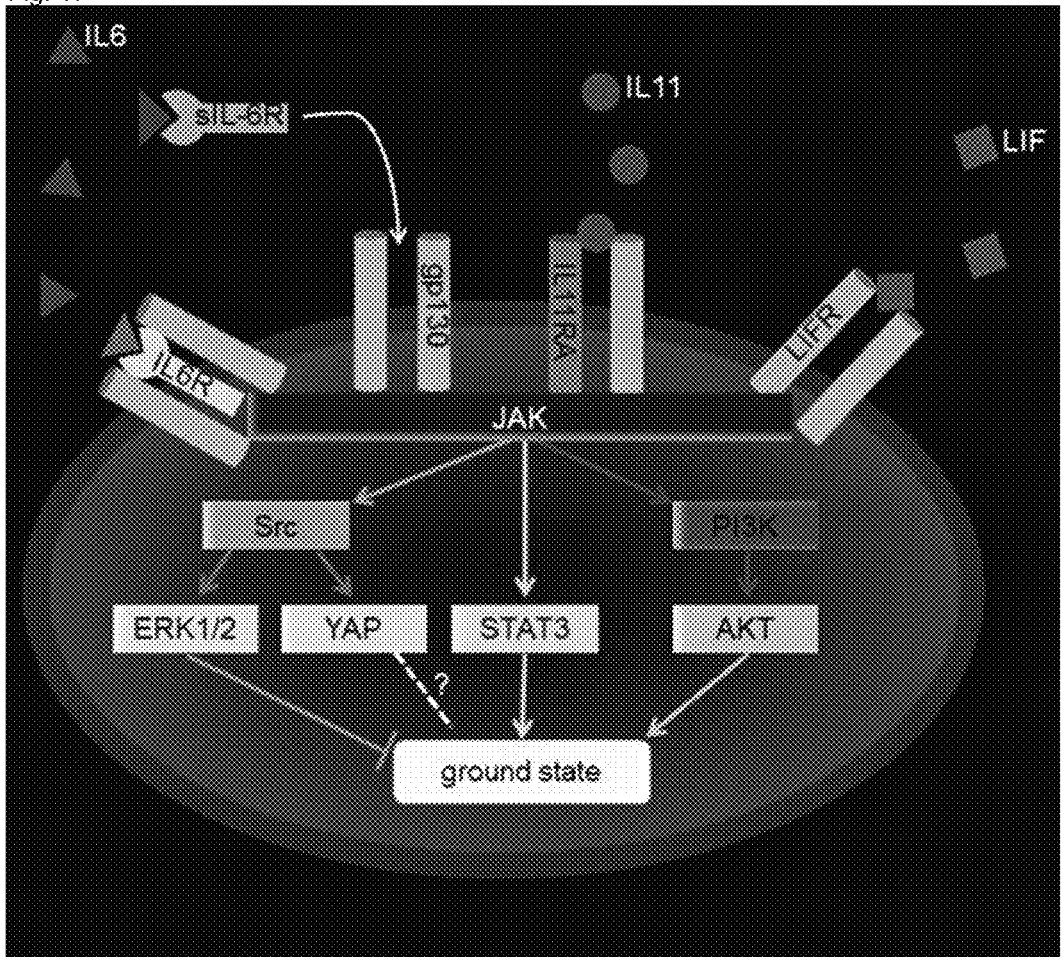

FIG. 17. Schematic representation of the effect of IL-6, IL-11 and LIF on JAK signalling and maintenance of the ground state in naïve PSC.

Figure 18:
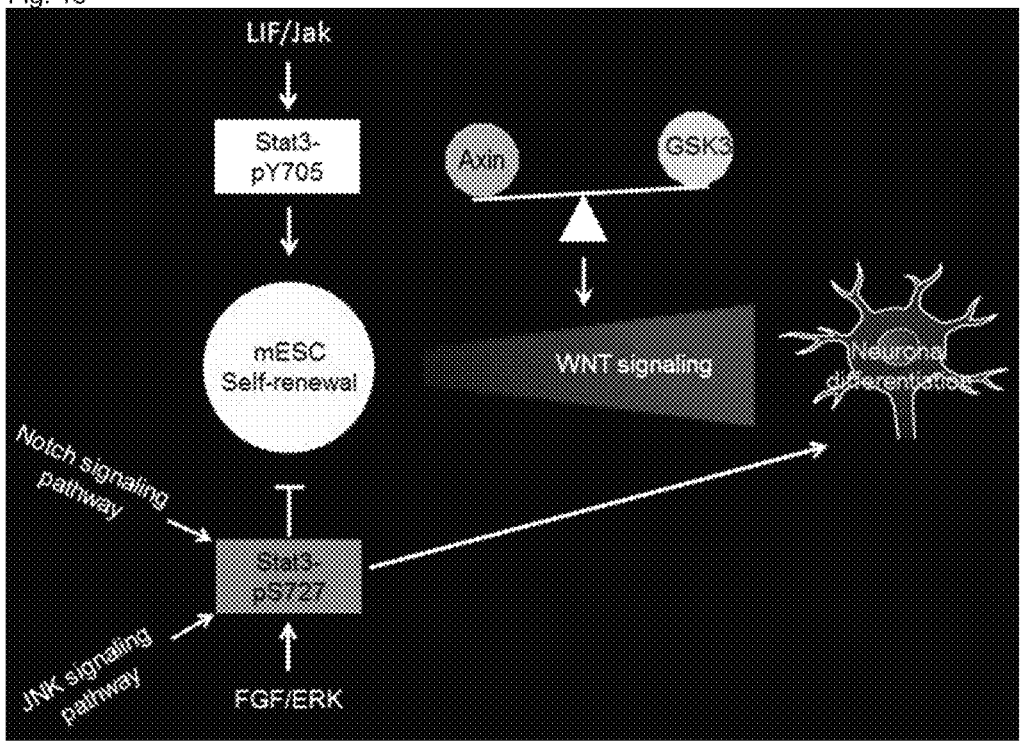

FIG. 18. Schematic representation of the effect of STAT3 on SC self-renewal and the balance of Wnt signalling.

Figure 19:
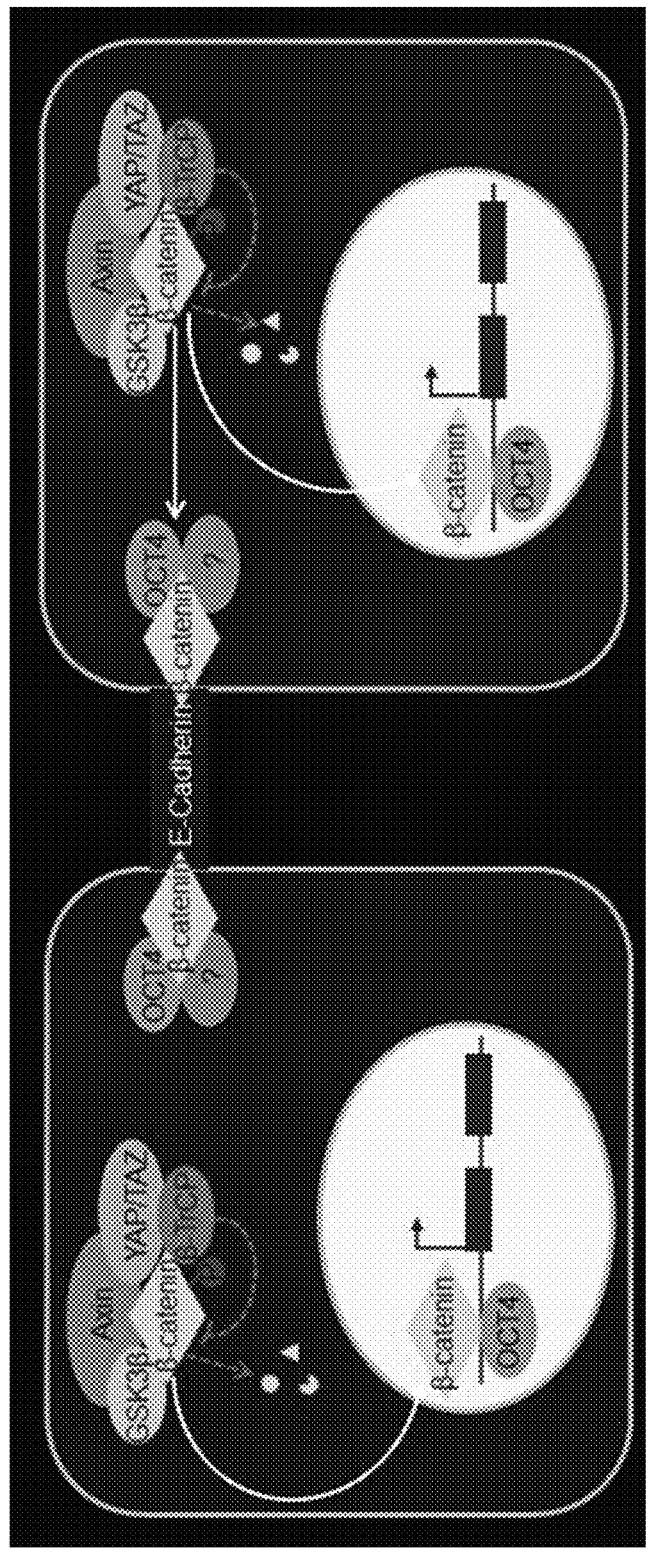

FIG. 19. Schematic representation of the effect of Beta-Catenin in transcriptional modulation in addition to cytosolic function in complex with E-Cadherin.

Figure 20:
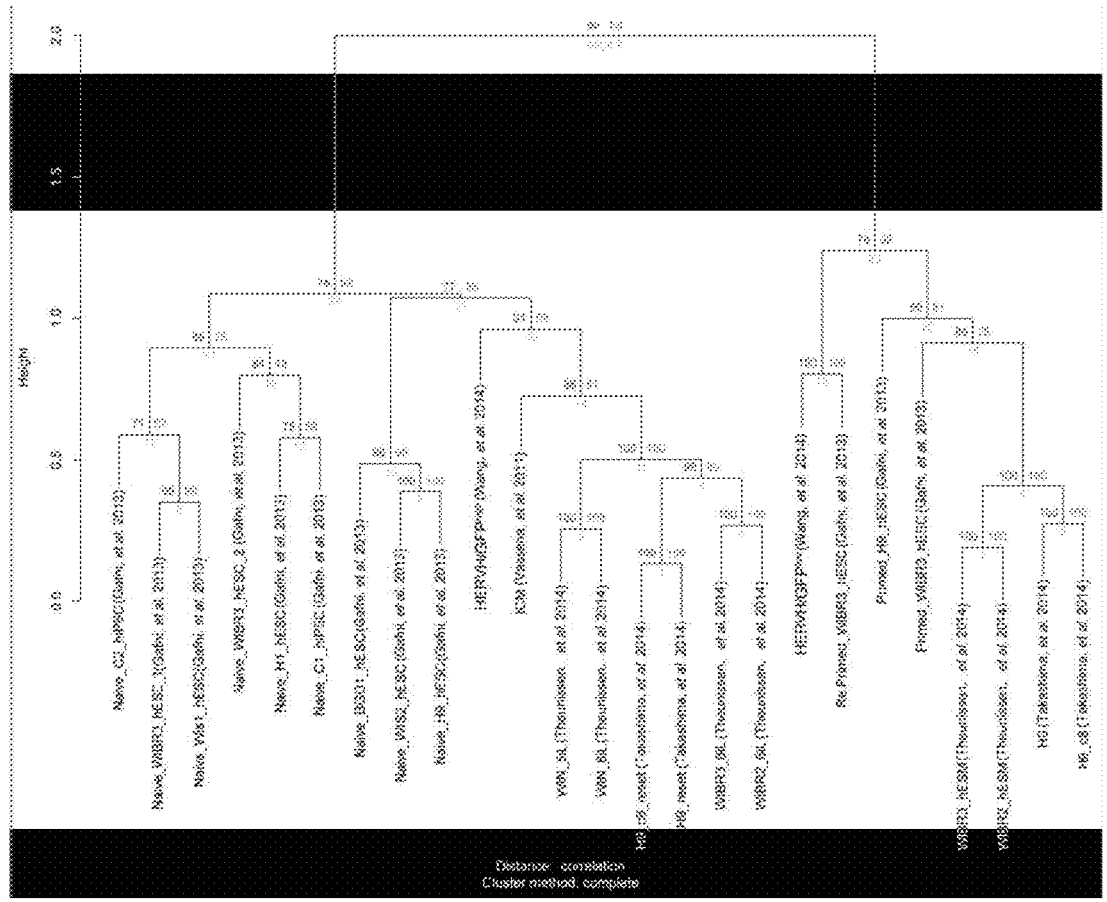

FIG. 20. Cluster dendrogram with AU/BP values (%)

Demonstrates a clustering of various naive PSCs cultivated in various conditions. The 4i condition of the present invention enables the production of cells that show strong similarity to the cells of the inner cell mass, thereby demonstrating the advantages of the present invention.

EXAMPLES

The examples provided herein relate to various preferred embodiments of the invention not intended to be limiting to the invention described herein.

Figure 1:
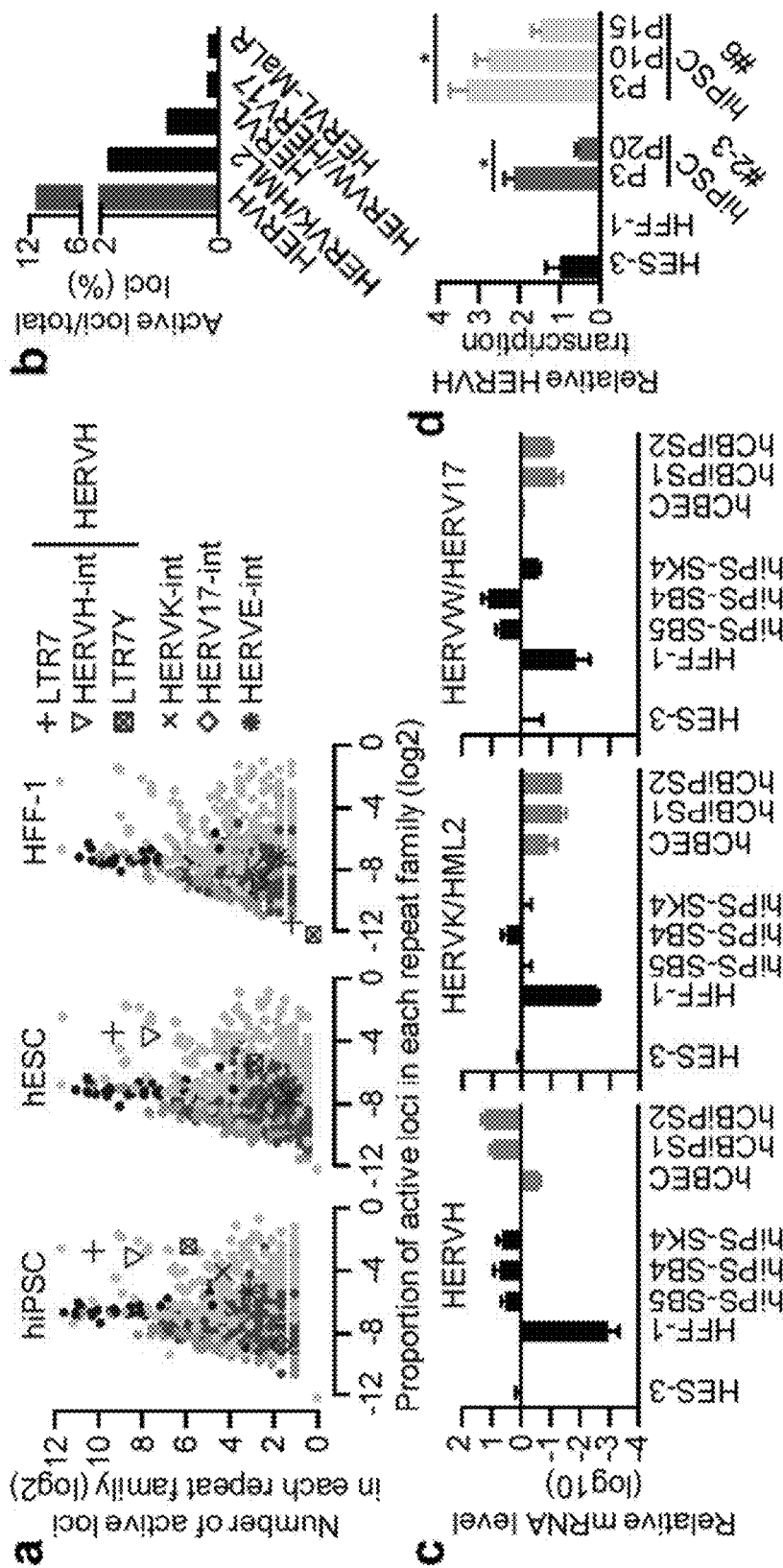
FIG. 1. HERVH is a specific marker of human pluripotent stem cells (hPSCs)

While many genes are involved in pluripotency, transposable element (TE) transcription, particularly involving ERVs, has wired different genes into the network in humans and mice[7]. Given a role for ERVs in pluripotency[8-10], we surveyed RNAseq data of human pluripotent stem cells (hPSCs), notably hESCs and hiPSCs finding that several TEs are expressed at higher levels in hPSCs, ERV1 type of long terminal repeat (LTR) retroelements being foremost, of which HERVH was the most highly expressed[8,11] (FIGS. 1a-b, 5a-b). Uniquely aligned reads indicate that 550 of the 1225 full-length HERVH genomic copies are transcribed in hPSCs (FIGS. 5c-d). Raised transcription was associated with elements containing consensus LTR7 rather than diverged variants (LTR7B/C/Y). Lower expression of other ERVs (FIG. 1b) was confirmed via qRT-PCR (FIG. 1c). We focused on HERVH, as this was the only one detected by qRT-PCR in all hiPSC lines analysed (FIG. 1c). Results are robust to use of reads that map to more than one location.

To address how specific HERVH transcription is to hPSCs we compared RNAseq datasets of hPSCs and multiple differentiated cells and tissues (FIG. 5c). In agreement with our hiPSC data, HERVH transcription was highest in hPSC lines. The majority of the transcribed loci are identical between hiPSCs and hESCs (FIGS. 5c-d). HERVH transcription levels are much lower in both differentiated cells and cancer cell lines (FIG. 5c).

HERVH transcription levels are higher in hiPSCs at early passages following reprogramming (FIG. 1d), indicating that the reprogramming process itself might induce HERVH expression. At later passages the transcription of HERVH in hiPSCs approaches hESC levels.

Consistent with HERVH transcription in hPSCs, ChIP-seq data show that, in contrast to HERVK and inactive HERVHs, active HERVHs are marked with transcriptionally active histone marks[11,12] (H3K4me1/2/3, H3K9ac, H3K36me3 and H3K79me2), while the repressive marks (H3K9me3 and H3K27me3) are rare, indicating functioning as active promoter/enhancers (FIGS. 2a, 6a-e). Notably, active HERVHs are also enriched with binding sites of the pluripotency regulators/modifiers CHD1[13] and Myc/Max[14] (FIGS. 6b-c). HERVH activation is also inversely correlated with the DNA methylation status of LTR7 of HERVH, as evidenced by hypomethylation in active LTR7 regions in hPSCs[15] (FIG. 6f).

To determine whether HERVH is a direct target of core pluripotency-associated transcription factors (TFs) we interrogated HERVH in hESC_H1 ChIP-Seq data[3]. This identified NANOG and OCT4 (FIG. 7a). A candidate KLF4 binding site was also identified within HERVH's LTR (FIG. 2b). We additionally asked which TF motifs are significantly enriched across four in silico tests (FIG. 7b). Only one, LTR-binding protein 9 (LBP9)—alias murine Tfcp2l1—was significant across all analyses (FIG. 7b). Tfcp2l1 is within the Oct4 interactome[16] and binds regulatory regions of Oct4 and Nanog[17] in mESCs. LBP9's direct binding to LTR7 is confirmed by ChIP-qPCR and EMSA (FIG. 2c, and FIG. 7c). EMSA further demonstrates LBP9/NANOG cooperation in binding LTR7 (FIG. 7c), consistent with synergy following simultaneous over-expression (FIG. 11c). LBP9-specific binding was also detected in the 5'-region of NANOG (FIG. 2c).

In vitro differentiation assays show that HERVH transcription levels decline over time in parallel with declines in OCT4, NANOG and LBP9 (FIG. 7d), suggesting a role in HERVH expression. As expected, ectopic expression of LBP9, OCT4, NANOG and KLF4 activated the pT2-LTR7-GFP #2 reporter and enhanced endogenous HERVH transcription levels in human primary fibroblast (HFF-1), while overexpression of c-MYC or SOX2 had no effect (FIG. 2d, 11c). Conversely, a complementary 'loss of function' RNAi assay in hESCs_H9 revealed that HERVH transcription levels were reduced following OCT4, NANOG and LBP9, but not SOX2, knockdown (KD) (FIGS. 2e-f).

We confirmed that LBP9 directly stimulates HERVH-driven expression, by comparing in hiPSCs signals of a wild-type (WT) pT2-LTR7-GFP #1 reporter construct and a mutant lacking the LBP9 motif (ΔLBP9: FIG. 11d). When WT and mutant constructs were transfected into hiPSCs, the GFP signal was clearly detected from the WT reporter, but it was decreased by 2-fold in ΔLBP9 (FIG. 11d).

hESC-specific TFs OCT4, NANOG, KLF4 and LBP9 thus drive transcription in hPSCs. In contrast to mice in which LBP9 binding sites are genomically distinct from those other pluripotency TFs[6], the key pluripotent TFs cluster within the primate-specific HERVH (FIG. 2b).

To test the functional importance of HERVH, we analysed RNAseq data to investigate the influence of LTR7/HERVH on the expression of neighbouring regions. We find that LTR7 initiates chimeric transcripts, functions as an alternative promoter or modulates RNA processing from a distance (FIGS. 3a, 8b). 128 and 145 chimeric transcripts were identified in hiPSCs and hESCs, respectively (FIG. 8a). One gene can contribute to multiple chimeric transcripts. The chimeric transcripts between HERVH and a downstream gene generally lack the 5' exon(s) of the canonical version (e.g. SCGB3A2) while part of HERVH/LTR7 is exonized (e.g. RPL39L) (FIG. 3a). A significant fraction of HERVH sequence can be incorporated into novel, lineage-specific genes (e.g. ESRG: FIG. 3a) or lncRNAs (e.g. RP11-6918.2: FIG. 8d). We confirmed several hPSC specific chimeric transcripts by RT-PCR (FIG. 3a). Transcriptional start signals commonly map to HERVH-LTR boundary regions (FIG. 8c). Unlike the chimeric transcripts the canonical genes are commonly not expressed in pluripotent cells.

Nearly 10% of the transcripts driven off HERVH are annotated as lncRNA[12]. 54 transcripts were identified that are commonly detected in hPSCs, while the rest were sporadic (FIG. 8d). The former set includes linc-ROR and linc00458, known to modulate pluripotency[18,19]. Alignment of the 22 most highly expressed transcripts reveals an LTR7/HERVH-derived conserved core domain (CD) (FIG. 8f). The domain is predicted to bind RNA-binding proteins, including pluripotency factors (e.g. NANOG) and pluripotency-associated histone modifiers (e.g. SET1A and SETDB1) (FIG. 8g). In agreement with a role in pluripotency, linc00458 physically interacts with SOX2[19].

To explore the effect of either LBP9 or specific HERVH-derived transcripts on the reprogramming process, we asked whether forced expression of LBP9, ESRG or the conserved domain of lncRNAs (LTR7-CD) modulates the fibroblast-hiPSC transition. While the overexpressed gene products affect neither pluripotency nor self-renewal (FIGS. 9a-b), all facilitate reprogramming by accelerating the mesenchymal-epithelium transition or hiPSC maturation (FIGS. 3b, 9c).

While LBP9 is key to the murine naïve state[62,0], HERVH is primate-specific. To determine whether HERVH/LBP9 delineates a primate-specific pluripotency circuitry, we performed "loss of function" experiments using small hairpin RNAs (shRNAs) against LBP9 or HERVH (FIGS. 3c-f, 9d-g). Pluripotency-associated TFs and markers are downregulated, while multi-lineage differentiation markers are up-regulated upon knockdown of either, but not in controls (FIG. 3c-d, 9f-g). Depletion of LBP9 or HERVH in hESCs thus results in loss of self-renewal. Knockout of LBP9 similarly abolishes hESC self-renewal (FIGS. 9h-j). In contrast to hPSCs, the Tfcp2l1/LBP9 knockdown in mESCs does not reduce levels of Oct4, Sox2 and Nanog in serum-based conditions (FIG. 9k)[21], but only in 2i[6]. In fact, Tfcp2l1/LBP9 does not affect self-renewal, but rather differentiation potential (FIG. 9k).

Genome-wide gene expression patterns are highly similar between LBP9 and HERVH knockdowns (FIG. 3e), consistent with LBP9 regulating HERVH-driven expression. 1094 of the 2627 genes are similarly regulated in LBP9/HERVH knockdowns (FIG. 3f). While some HERVH-derived chimeric transcripts are potentially directly affected by depletion of HERVH, qRT-PCR identifies 19 HERVH-derived lncRNAs, down-regulated in response to both HERVH and LBP9 knockdowns (FIG. 8e).

While several of the differentially expressed genes are associated with murine pluripotency, the LBP9/HERVH-driven list of transcripts defines a primate-specific pluripotency network. Our analyses defined two classes of genes, (I) those conserved between mouse and human that contribute to the pluripotency in both, and (II) a primate-specific group that includes (a) those with an orthologous partner, but are not involved in murine pluripotency and (b) novel (not in mouse) transcripts (FIGS. 8b, 8d). Several HERVH elements in class IIa affect gene expression in cis, and drive specific genic isoforms (e.g. SCGB3A2). A subset of class IIb contains HERVH-derived novel sequences (e.g. linc-ROR, linc000548, ESRG) (FIG. 8d).

We examined one class IIb transcript in detail. ESRG has a putative open reading frame (ORF) only in human (FIG. 10a; Supplementary Data 1), and is uniquely expressed in human inner cell mass (ICM) and PSCs (FIG. 10b). Knockdown of ESRG compromised self-renewal of hESCs, as many pluripotency-associated genes were decreased, while SOX2 expression was slightly elevated (FIGS. 10c-e). The KD-ESRG colonies lost their hESC morphologies and committed to differentiation (FIGS. 10e-f). Expression of ESRG along with the OSKM pluripotency factors has a similar effect on the reprogramming process compared with LBP9 (FIG. 10c). ESRG is thus an HERVH-associated novel gene required for human-specific pluripotency, with a more specific phenotype than upstream regulators.

Given that the naïve-associated TFs together cluster on HERVH and the HERVH-derived products are essential for primate pluripotency, we asked whether HERVH-driven transcription marks the naïve-like stage in hPSC cultures. To explore this the reporter construct, pT2-LTR7-GFP #2 was integrated into the genome of either mouse or human PSCs (FIGS. 4a, 11a-b, 12i) by Sleeping Beauty gene transfer, providing stable transgene expression[22]. While all of mESC colonies homogeneously express GFP (FIG. 11a), only ~4% of cells in each hESC colony show a strong GFP signal (GFP(high)), indicating cellular heterogeneity (FIGS. 11e, 11h-j). The fraction either weakly or unexpressing GFP we term GFP(low) and GFP(−) respectively (FIG. 4a, 11b, 11e). RNAseq data of hESCs from single cells[23,24] and hPSC lines confirm that pluripotent cultures exhibit variability in HERVH expression (FIG. 5d), indicating that the GFP(high) subpopulation may differ from the GFP(low) subpopulations. Consistent with a naïve-like state, data mining of single cell RNAseq datasets[24] reveals that the expression level of HERVH in hESCs is correlated with several pluripotency-associated genes, including naïve-associated TFs (FIG. 5e).

To collect uniform GFP(high) and GFP(low) hPSCs, we performed two rounds of FACS (FIG. 4a). We first sorted GFP(+) cells that were further divided into GFP(high) and GFP(low) categories. Strikingly, GFP(high) cells are capable of forming tight, uniformly expressing 3D colonies characteristic of naïve mESCs (FIG. 4a). In contrast, GFP (low) cells form flat colonies, resembling mouse epiblast stem cells (mEpiSCs) (FIG. 4a). We also observed mosaic colonies. Immunostaining of 3D and chimeric colonies reveals that the NANOG and GFP(high) signals copresent. Thus, the GFP(high) subpopulation in human pluripotent stem cells are enriched for cells resembling the murine naïve/ground state.

To examine this possibility, GFP(high) vs GFP(low) cells were subjected to expression analyses. qRT-PCR revealed significant up-regulation of naïve-associated TFs[4-6] and down-regulation of lineage-commitment genes in GFP (high) vs GFP(low) (FIG. 4b). As in naïve mESCs[25] and human ICM[26] X chromosomes are activated in GFP(high) hESCs_H9, as evidenced by nearly complete loss of condensed H3K27me3 nuclear foci (FIG. 4d) and low level of XIST expression (FIG. 4c). However, nearly 60% GFP(low) hESCs transited from GFP(high) hESCs are marked with condensed H3K27me3 foci or higher density of H3K27me3 in the nucleus (FIGS. 4d, 12g). These data are consistent with a naïve-like state for GFP(high) cells and a primed state for GFP(low) cells (one X chromosome inactivated or in process of being inactivated).

GFP(high) cells can be maintained in the modified 2i/LIF medium for a long time, with higher single-cell clonality as well as full pluripotency (FIG. 12a-d). However, GFP(high) and GFP(low) cells have slightly different differentiation potential. When differentiation triggered, certain naïve-associated TFs are maintained at higher levels in GFP(high) naïve-like cells compared with GFP(low), and start their differentiation program with a delay (FIGS. 12e-f). Early passage hPSC cultures behave somewhat similarly to GFP (high) cells (FIGS. 13a-c).

Transcriptomes of GFP-sorted cell populations and previously characterized naïve-like and primed hPSCs[4] and mouse counterparts as well as human ICM, support a naïve-like status of GFP(high) cells. Unbiased hierarchical clustering of the expression profiles revealed that GFP(high) and GFP(+) cells have a similar, but non-identical, expression pattern, one that sharply contrasts with GFP(low) (FIG. 12h). Strikingly, GFP(high) and GFP(+) samples clustered with human ICM and the published naïve-like hPSCs, respectively (FIG. 4e). Importantly, GFP(high) cells cluster closest to human ICM (FIG. 4e).

Cross-species comparison of expression of 9,583 mouse-human orthologs revealed that GFP(high) and GFP(+) correlated to published naïve hPSCs, while GFP(low) clustered with primed cells (FIGS. 4f-g), supporting the significance of HERVH-driven transcription defining a naïve-like state.

To address how gene expression changes up to the ICM stage, we analysed 114 RNAseq samples harvested in early developmental stages of embryogenesis[24] and 3 RNAseq samples of naïve-like hESCs (3iL_hESC[3]). HERVH expression appears already in the zygote, but the pattern of activated loci changes during early development (FIGS. 13d-e). Importantly, the pattern of active loci characteristic of ICM is the closest to naïve-like hESCs, including GFP (high) (FIG. 13d). Notably, the number of activated HERVH loci is particularly high in hESCs, especially in naïve-like cells and marked with H3K4me3 (FIGS. 13d-f), indicating that HERVH may play some roles in the derivation and/or maintenance of naïve-like hPSCs.

To address how HERVH-driven gene expression modulates pluripotency, we surveyed differentially regulated genes in GFP(high) vs GFP(low), intersected by HERVH cis-regulation. The differentially regulated genes located in the neighbourhood (+/−50 kb) of HERVH display a similar expression pattern to those differentially expressed in GFP (high) vs GFP(low) and in human naïve-like vs primed stages, derived under specific culture conditions[4] (FIG. 13h). In contrast, a distinct pattern is observed when comparing mESCs vs mEpiSCs (FIG. 13g). Strikingly, there is an inverse pattern of expression between genes defining naïve-like stage [up in GFP(high) vs GFP(low)] and those that are down-regulated in HERVH knockdowns (rho=−0.6, P<<0.0001; FIG. E9i), underlying the significance of HERVH in regulating the naïve-like state in humans. Differentially expressed genes between GFP(high) vs GFP (low) populations were enriched for Gene Ontology (GO) terms of developmental processes, morphogenesis and organismal processes (FIG. 13j). Transition of naïve-like cells into primed state following depletion of HERVH supports the above conclusion (FIG. 13k).

While GFP(high) cells have many properties resembling naïve mESCs, they are better regarded as being naïve-like, not least because it is unclear that human and naïve mESCs need be identical. Indeed, while LBP9 is associated with pluripotency[6,20] in mammals, HERVH was recruited to the pluripotency network exclusively in primates. How then to define naïve human pluripotency if we do not necessarily expect them to be identical to mouse ones? We suggest that, rather than hard to replicate inter-species chimaera experiments[27], the optimal approach is to define cells by similarity of expression to the ICM. In this regard GFP(high) cells are one of the best current models of naïve-like status.

That LBP9 forms heteromer complexes functioning either as a transcriptional activator or a repressor, depending upon the partner[28] is consistent with HERVH being recruited to the pluripotency network by serendipitous modification of a pluripotency factor detailed to defend the cell against it (FIG. 14). Whatever the origin, LTR7/HERVH is an efficient reporter for the naïve-like state most probably because it acts as a platform for multiple key pluripotent transcription factors[29]. Similarly the LTR7-GFP reporter enables optimization of naïve-like hPSC culture conditions.

Further optimization of the culture medium was conducted leading to various improved culture media. These media were tested and compared to known media via expression profiling of various SC marker transcripts. As shown in FIG. 15 the cells cultured in optimized 4i media showed good colony formation and strong GFP expression of the LTR7 reporter.

As shown in the FIG. 16, the 4i medium of the present invention leads to improvements with respect to the marker molecules expressed in naïve cells cultured in 4i compared to the previously described 5i L/A[27]. In addition to the marker molecule expression, the 4i medium leads to reduced incidents of transposition, therefore showing greater genome stability.

To describe the approach in detail, the conventional human pluripotent stem cells can be converted into a human inner cell mass-like naïve state, under the special culture condition called the 4i medium, which the inventors have developed.

The naïve culture condition contains basal medium, cytokines and several small molecules that inhibit different signaling pathways and epigenetic modification.

The basal medium comprises commercial medium: Neurobasal medium, DMEM/F12, L-glutamine, NEAA, N2 supplement, B27 supplement (w/o Vitamin A), Vitamin C, BSA and 2-Mercaptoethanol.

The cytokines comprise human IL6/sIL-6R, human LIF, human Activin A, human insulin, human bFGF and human IL11.

The small molecules contain a MEK/ERK inhibitor (such as PD0325901: 0.2-1 µM), a B-raf inhibitor (such as SB590885: 0.1-0.5 µM), a JNK inhibitor (such as TCS-JNK-6o: 0.5-5 µM), a GSK3 inhibitor (such as BIO: 0.05-0.5 µM; or CHIR99021: 0.1-1 uM), a Axin stabilizer (such as XAV939: 2-5 µM; or endo-IWR1: 1-5 µM), a PKC inhibitor (such as Go6983: 2-4 µM), a Notch inhibitor (such as DAPT: 2-10 µM), a Sonic Hedgehog inhibitor (such as HPI1: 1-5 µM), a BMP inhibitor (such as K02288: 1-5 µM), a TGFbeta inhibitor (such as A83-01: 0.2-0.5 µM), a mitochondrial pyruvate dehydrogenase kinase inhibitor (such as DCA: 2-10 µM), a histone methyltransferase inhibitor such as (DZNep: 0.01-0.1 µM), and a histone deacetylase inhibitor (such as Sodium butyrate: 0.1-0.5 mM; or SAHA: 0.01-0.05 µM). Various tests were conducted with each of the components being varied within the provided concentration ranges in order to optimize the medium until excellent GFP expression was achieved from the reporter.

The conventional human pluripotent stem cells (hPSCs) were tagged with LTR7-GFP and/or LTR7Y-mCherry, delivered by the Sleeping Beauty transposon system. Then, the tagged hPSCs are reprogrammed into a hICM-like naïve state simply via culturing in 4i medium. In details, the tagged hPSCs cultured in feeder cells are pre-treated with the histone methyltransferase and deacetylase inhibitors for 2-4 days, and then cultured in the chemical-based medium. About 10-14 days later, the reporter-positive cells are enriched/isolated by FACS, and maintained in the defined exno-free and feeder-free culture condition. The cells produced via culture in the 4i medium led to very similar expression profiling to the ICM (FIG. 20).

Methods

Cell Culture.

Human foreskin fibroblasts (HFF-1) (ATCC, SCRC-1041) were cultured with the fibroblast medium (DMEM, 20% FBS, 1 mM L-glutamine, 1% nonessential amino acids, 0.1 mM 2-mercaptoethanol and primocin), and were passaged every three-four days. Human embryonic stem cells (hESCs) were cultured in matrigel/feeder-coated plates in the conventional hESC medium (knockout DMEM, 20% knockout serum supplement, 1 mM L-glutamine, 1% non-essential amino acids, 0.1 mM 2-mercaptoethanol, 10 ng/ml bFGF (Pepro Tech, 100-18B) and primocin), or in naive hESC mediums NHSM[4] or 3iL[3] medium or in human 2i/LIF medium (this work). The human 2i/LIF medium is based on mouse 2i/LIF medium[6] (knockout DMEM, 20% knockout serum supplement, 1 mM L-Glutamine, 1% nonessential amino acids, 0.1 mM 2-mercaptoethanol, 10 ng/ml LIF, 3 µM CHIR99021, 1 µM PD0325901 and primocin, but the CHIR99021 was changed from 3 to 1 µM, and the medium was supplemented with 10 ng/ml bFGF). The medium was changed daily. hESCs were treated with collagenase IV (1 mg/ml) (Life Technologies, 17104-019) and then passaged onto new matrigel/feeder-coated plates every four to five days. The generation of hiPSC line hiPS-SB4 and hiPS-SB5 has been reported[30]. iPSC lines hCBiPS1 and hCBiPS2 and their culture conditions have been described previously[35]. They were derived from human cord blood-derived endothelial cells (hCBEC) using a lentiviral vector expressing reprogramming factors OCT4, SOX2, NANOG and LIN28[35]. Similarly, the line hiPS-SK4 was produced using HFF-1 cells and the same lentiviral overexpression construct. Successful reprogramming for the hiPS-SK4 cell line was verified by morphology, the expression of pluripotency markers, karyogram analysis and the ability to generate teratomas on immunocompromised mice (data not shown).

Mouse ESCs were cultured in gelatin/feeder-coated plates with the mESC medium (knockout DMEM, 15% fetal calf serum (FCS), 1 mM L-Glutamine, 1% nonessential amino acids, 0.1 mM 2-mercaptoethanol, 10 ng/ml LIF (Millipore, LIF1010) and primocin) or mouse 2i/LIF medium[6]. To prepare feeders, mouse embryonic fibroblasts (Passage 4) isolated from CF-1 mouse embryos, were treated with mitomycin C (10 μg/ml) for 2-3 hours.

All above mentioned cell cultures tested negative for *mycoplasma* infection. Karyotype of hESC_H9 was analyzed using the G-banding method[36] indicating normal karyotype (FIG. E8*j*).

Reprogramming Assay.

Reprogramming was performed as described previously[30,37]. Briefly, 200,000 HFF-1 cells were transfected with pT2/RMCE-OSKM (2 μg) and pT2-CAG-amaxaGFP, or pT2-CAG-HA-LBP9, or pT2-CAG-ESRG, or pT2-LTR7-CD (1 μg per plasmid) using the Neon™ transfection system (Life technologies), and transposition was induced by SB100X[22] (1 μg). The transfected cells were plated onto matrigel-coated 6-well plates and cultured in the fibroblast medium (first two days), then medium was changed to the hESC medium (day 2 post-transfection). After three weeks, several of hESC-like colonies were picked for expansion and characterization, while the rest of the colonies were fixed in 4% with paraformaldehyde and subjected to immunostaining.

In Vitro Differentiation Assay.

To spontaneously differentiate hPSCs to embryoid bodies (EBs), hESCs/hiPSCs cultured geltrex-coated 6-well plates. Cells from one well were dissociated with collagenase IV (1 mg/ml) for 5 min, and then split into small cell clumps. The small cell clumps were transferred into three 10-cm low-attachment dishes, and cultured in EB medium (knockout DMEM, 20% knockout serum replacement, 1 mM L-Glutamine, 1% nonessential amino acids, 0.1 mM 2-Mercaptoethanol and primocin). The medium was changed every two days. The embryoid bodies were cultured for ten days followed by collection for RNAseq or then re-plated in gelatin-coated 6-well plates for one week followed by immunostaining.

Differentiation Potential Assay.

GFP(high) and GFP(low) cells collected from the same FACS-sorted hESC clone are seeded on matrigel/feeder-coated plates, respectively. First, the GFP(high) and GFP (low) cells are cultured either in the human 2i/LIF medium or conventional hESC medium. Following three days culturing in the respective mediums, cells were exposed to EB medium. To improve single-cell-viability, the cells are treated with the ROCK inhibitor, Y-27632 (Millipore, 10 μM) for 48 hours before and after sorting.

Immunostaining.

hPSC colonies were cultured on matrigel/feeder-coated chamber slides (BD Biosciences). Following three days of culturing, cells were fixed for 30 min in 4% paraformaldehyde, permeabilized for 30 min in 1% Triton X-100, and blocked for 1 hour in Blocking solution (Applied StemCell, ASB0103). Fixed cells were incubated overnight at 4° C. with the primary antibodies (OCT4, SOX2, NANOG, SSEA4, TRA-1-60, PAX6, TUBB3 (BetaIII-Tubulin), SOX17, α-SMA and CDX2) (Table S3). After washing in PBS, the cells were incubated with secondary antibodies (Life technology) for 1 hour at room temperature. DAPI (Sigma, D9564) was used for staining the nuclei. Immunostaining of reprogramming plates was performed as previously described[38]. Briefly, cells were fixed with 4% paraformaldehyde and stained with biotin-anti-TRA-1-60 (eBioscience, 13-8863-80) and streptavidin horseradish peroxidase (Biolegend, 405210), diluted in 1% Triton X-100 (containing 0.3% BSA). Staining was performed using the Vector labs DAB kit (SK-4100). Stained hiPSC colonies were counted with ImageJ software. Immunofluorescence microscopy to determine XaXi status of hESCs. GFP(high) cells were seeded on matrigel-coated coverslips in 12-well culture plates. Following four days of culturing, the cells were fixed with 4% paraformaldehyde (Sigma) supplemented with DAPI for 15 min, and permeabilized with 0.5% Triton X-100 for 5 min. Fixed cells were incubated with primary antibodies (NANOG or H3K27me3, Novus Biologicals and Millipore respectively) overnight at 4° C., then washed three times with PBS, and incubated with secondary antibodies (Alexa Fluor®, Life Technologies) for one hour. After additional washing, the samples were mounted using ProLong® Gold antifade reagent (Invitrogen) and images were taken using a Zeiss LSM710 point-scanning single photon confocal microscope. 3D image movies were created by Imaris® Imaging Software (Bitplane). To statistically compare X chromosome state in GFP(high) and GFP(low) cells which were transited from GFP(high), images on GFP(high), GFP(low) hESCs, and female human fibroblast were analyzed and quantified for the proportion of cells with condensed H3K27me3 foci which mark the inactive X chromosome. Average 100-450 individual cells per samples from 5 images were counted.

DNA Constructs.

The LBP9 ORF was amplified from human placenta cDNA by PCR with Pfu Ultra II Fusion HS (Agilent Technologies). A NotI restriction site was added to the 3' end of the fragment (for cloning purposes). A single, ~1,500 bp band was cloned into pJET1.2/blunt using the CloneJET PCR Cloning Kit (Thermo Scientific). The LBP9 fragment was re-amplified from pJET1.2-LBP9 plasmid digested with NotI and was cloned into pHA5 expression vector. The HA-LBP9 fragment was cut from pHA-CAG-HA-LBP9 vector and cloned into the Sleeping Beauty transposon[39], pT2-CAG-GFP vector. LPB9 expression from pHA-CAG-LBP9 or pT2-CAG-HA-LBP9 was confirmed by Western-blotting. The size of the observed band was in good agreement with the molecular weight of the full-length protein (54,627 Da). ESRG was PCR amplified from hESC cDNA (Pfu Ultra II Fusion HS). The MluI and BglII restriction sites were added to the 5' and 3' ends, respectively, for subsequent cloning. A single ~300 bp band was digested with MluI and BglII restriction enzymes, and then cloned into pT2-CAG-GFP vector. To clone pT2-LTR7-CD, 22 highly expressed, HERVH-derived lncRNAs were first aligned (Clustal Omega alignment tool), and the lncRNA core domain (CD) sequence (Table S1) was synthetized. The synthetic LTR7-CD flanked by MluI/BglII restriction sites was cloned into the pT2-CAG-GFP vector by replacing GFP. Reporter assays. The individual HERVHs were compared with the HERVH consensus sequence from Repbase (http://www.girinst.org/repbase/). The ESRG locus of HERVH was selected to generate a reporter construct. Two different DNA fragments, #1 and #2 were amplified (for primers see Table S1). LTR7 #1 (566 bp) contains the ESRG-LTR7 flanked by ~110 bp upstream genomic sequence, while ESRG-LTR7 #2 (1,194 bp) contains the LTR7 plus sequence from the HERVH-int. EcoRI and MluI restriction sites were added to the 5' and 3' ends of the fragments, respectively, for cloning purposes. The two DNA fragments were cloned into SB transposon-based pT2-CAG-GFP vector, digested with EcoRI and MluI (to remove CAG promoter) to generate pT2-LTR7-GFP #1 and pT2-LTR7-GFP #2. To clone an LBP9-motif deleted reporter construct, a 17 bp segment containing the LBP9 motif was removed from pT2-LTR7-GFP-#1 by inverse PCR (FIG. E7d). The PCR-amplified ~5,600 bp fragment was gel-isolated (Qiaprep, Qiagene), circularized and subsequently transformed into chemical competent DH5a cells. The deletion was confirmed by sequencing. The modified region was moved into the original vector by NcoI digestion. To generate multiple LTR7 reporter-constructs (#3-#6), LTR7 was PCR-amplified from different genomic loci (Table S1). The obtained fragments were gel isolated and cloned into pJet1.2 vector using the CloneJet PCR Cloning Kit (Thermo Scientific) and confirmed by sequencing. In pT2-LTR7-GFP #3-#6, the LTR7 (flanked by StuI and Bsu36I) sequence of the pT2-LTR7-GFP #2 reporter was replaced by LTR7 (#3-6). Finally, these vectors were transfected into fibroblasts and hiPSCs for subsequent analyses. The transfected fibroblasts and hiPSCs were cultured in the conventional hESC medium. GFP(+) cells were quantified by FACS on Day 6, post-transfection.

TABLE S1

Following primers were used to amplify the various LTR sequences used in the construction of the various reporter constructs.

| Name | Forward | Reverse |
| --- | --- | --- |
| LBP9 | ATGCTCTTCTGGCACACGCAG (SEQ ID NO 4) | TTGCGGCCGCTCAGAGTCCACATTT CAGGATGA (SEQ ID NO 5) |
| LBP9-motif deletion | CTCAAAAAGCACCCCCACTGA (SEQ ID NO 6) | AAGGACTTTCACAAGGTAATGTC (SEQ ID NO 7) |
| LTR7(ESRG)#1 | AATCGCTAGCAGGGAGGTCCCCC GATCCGA (SEQ ID NO 8) | CGTGAATTCCTGCTAAGTGCCCACA CAGCACT (SEQ ID NO 9) |
| LTR7(ESRG)#2 | GCGTGAATTCATGCTGCGAGATGG GAAACA (SEQ ID NO 10) | AATCGCTAGCGGGTGAAGGAGAAG GGGTTG (SEQ ID NO 11) |
| LTR7#3 | TATCAGTTGGTAAATGAATGGA (SEQ ID NO 12) | GCTGGTCGGTCTGAGGAC (SEQ ID NO 16) |
| LTR7#4 | CTGCAGTGGTTGGCTACA (SEQ ID NO 13) | GCTGGTCAGTCTGAGGAC (SEQ ID NO 16) |
| LTR7#5 | ATTAACTGTAGAGGGAAGTG (SEQ ID NO 14) | GCTGGTCGGTCTGAGGAC (SEQ ID NO 16) |
| LTR7#6 | CTTCTCTACTCACAGTTGAT (SEQ ID NO 15) | GCTGGTCGGTCTGAGGAC (SEQ ID NO 16) |

Gain of Function Assays.

Individual expression plasmid constructs containing OCT4, NANOG, SOX2, KLF4, c-MYC or LBP9 were transfected into 2×10⁵ HFF-1s, respectively. The transfected cells were collected for total RNA extraction and qRT-PCR on day 4 post-transfection.

Generating shRNA Constructs.

To generate shRNA against HERVH, we first aligned all active (based on RNAseq data) full-length HERVHs and selected several conserved sequences. The selected conserved sequences were analysed by the Block-It RNAi Designer online program (https://rnaidesigner.invitrogen.com/rnaiexpress). The shRNA sequences of score >3.5 were further analysed for their specificity using BLAST against human genome. shESRG and shLBP9 targeting sequences were designed using the online siRNA design tool siDESIGN Center (https://www.thermoscientificbio.com/design-center/?redirect=true). 60-mer oligos were synthesized, and then cloned into the FP-H1 vector[40]. shRNA targeting GFP was used as a control. GFP, NANOG, OCT4 and SOX2 shRNAs were previously described[41]. Clones were verified by sequencing. For the list of shRNAs see Table S2.

Generating Stable shRNA Knockdown hPSC Lines.

All of hESC/hiPSCs were cultured under the same condition, including identical passage numbers. hESCs/hiPSCs cultures containing spontaneously differentiated cells (>10%) were excluded from the knockdown experiments. shRNA plasmid (10 μg) for each gene was transfected into 1×10⁶ hPSCs by the Neon™ transfection system followed by G418 (500 μg/ml) selection on day 2 post-transfection until 7-10 days. Stable knockdown cell lines were harvested for FACS, immunostaining and RNA extraction.

Transfection of hPSCs.

Cells were treated with ROCK inhibitor Y-27632 (10 μM) (Millipore, 688000) overnight prior to transfection, and then trypsinized with Accutase (Life Technologies, A1110501) for 3 min at 37° C. to generate single-cell suspension. 5×10⁵ hiPSCs or hESCs were transfected with certain plasmids using the Neon™ transfection system. The transfected hPSCs were immediately re-plated onto the matrigel/feeder-coated 6-well plates in hESC medium containing Y-27632 (10 μM). Four hours post-transfection, the medium was refreshed in order to remove the transfection buffers and dead cells. The hESC medium was changed daily. Note that, the Neon™ transfection system was also used to transfect HFF-1, mouse embryonic fibroblasts, and mESCs (according to the manufacturer's protocol).

Analysing hPSCs by FACS.

Single cell suspension was generated by treating hiPSCs/hESCs with Accutase for 3 min at 37° C. 2×10⁵ cells were incubated with anti-TRA-1-81-APC antibody (eBioscience, 17-8883-41) for 30 min at 4° C. in PBS. Cells were washed and suspended in ice-cold PBS prior analysis on FACSCAlibur (BD Biosciences). 10,000 cells were typically analysed.

Generating Genetically LTR7-GFP Marked hPSCs.

Single cell suspension of 5×10⁵ hPSCs was transfected with 5 μg pT2-LTR7-GFP #2 and 500 ng SB100X using the Neon™ transfection system, and seeded onto matrigel/feeder-coated 6-well plates. One week post-transfection, hPSCs were treated with Y-27632 (10 μM) overnight, trypsinized into single cells, and purified with the feeder removal microbeads kit (Miltenyi Biotec, 130-095-531) before sorting by FACS. GFP-positive (+) and GFP-negative (−) were collected, respectively. The GFP(+) hPSCs were re-plated on matrigel/feeder-coated 6-well plates and cultured in hESC medium. One week later, the single GFP(+) colonies were picked up for expansion in hESC medium. The second round of sorting was performed on the expanded single-clones to collect hPSCs expressing strong and low GFP signal [referred as GFP(high) and GFP(low)], respectively. The GFP(high) hPSCs were re-plated onto matrigel/feeder-coated 6-well plates and cultured in 2i/LIF medium for further characterization. The pT2-LTR7-#2 marked individual hESC-H9 clones, GFP(high), GFP(+) and GFP(low) were characterised in multiple assays. The integration site of the single copy pT2-LTR7-#2 reporter in GFP(high) was determined (FIG. E8i).

Single Cell Cloning Assay.

1,000 GFP(high) hESCs_H9s collected from the second round of sorting, were seeded onto one matrigel/feeder-coated well of the 6-well plate and cultured in 2i/LIF medium with or without Y-27632 (10 μM). 1,000 GFP(low) hESCs_H9s were seeded onto one matrigel/feeder-coated well of the 6-well plate and cultured hESC medium with or without Y-27632 (10 μM). One week after seeding the hESCs were fixed with 4% paraformaldehyde for 1 minute, and then stained with alkaline phosphatase (Sigma, AB0300). Pictures of stained cells were analysed. Dark blue (undifferentiated), light blue (partially differentiated) and colourless (differentiated) colonies were counted, respectively.

qRT-PCR.

Total RNA was extracted from cells by using the Trizol kit (Invitrogen) following the manufacturer's instructions. 0.1 μg purified DNaseI-treated RNA, which was the mixture of biological triplicates, was used for reverse transcription (RT) (High Capacity RNA-to-cDNA kit, Applied Biosystems). Quantitative RT-PCR (qRT-PCR) was performed using the Power SYBR® Green PCR Master Mix (Applied Biosystems) on the ABI7900HT sequence detector (Applied Biosystems). Data were normalized to GAPDH expression using the ΔΔCt method. Error bars represent the standard deviation (s.d.) of samples carried out in triplicates. For the list of primers see Table S1.

Gel Mobility Shift Assay (EMSA).

2×10⁶ hiPSCs were transfected with 20 μg plasmids encoding pT2-CAG-HA-LBP9. Two days post-transfection cells were collected and washed with PBS. Cells were lysed in 100 μl lysis buffer (50 mM Tris-HCl, pH 8.0, 100 mM NaCl, 10 mM EDTA, 5% glycerine, 1% NP-40 and 1× protease inhibitor cocktail (Roche)) for 30 min at 4° C. Following removal of the cell debris by centrifugation at 20,000 g, binding reactions were performed in 25 μl volumes at room temperature for 30 min. DNA binding reactions contained, FAM-labelled LTR7-specific, complementary dsDNA oligonucleotides (LTR7 oligo), HA-LBP9 containing cell extracts, 10 mM Tris-HCl pH 8.5, poly(dI-dC), 1 mM EDTA, 50 mM KCl, 10 mM 2-mercaptoethanol (see also, FIG. E3c). Probe sequences are listed in Table S1. The gel buffer contained 50 mM Tris-borate pH 8.3, 1 mM EDTA. To supershift specific complexes, cell extracts were incubated with antibodies [anti-LBP9 (NOVUS); anti-NANOG (NOVUS)] at 4° C. for 15 min prior to addition of the dsDNA oligonucleotides. Protein-DNA complexes were separated by electrophoresis in 6% non-denaturing polyacrylamide gels at 4° C. Electrophoresis was performed at constant voltage of 200V for 3, 4 or 6 hours. The fluorescent signal was detected by using a FUJI FLA-3000 Imager.

ChIP-qPCR.

ChIP-qPCR was performed with the Transcription ChIP kit (Diagenode) according to the manufacturer's instructions with slight modifications. 1×10⁷ hPSCs were fixed in 1% formalin/hESC medium (v/v) for 10 min with gentle agitation on a rotator at room temperature. Fixation was stopped by the addition of glycine (125 mM) and agitation for 5 min at room temperature. Fixed cells were washed twice in ice-cold PBS, re-suspended in 15 ml lysis buffer. Chromatin was sheared by sonication to about 100-500 base pair fragments using a Bioruptor (Diagenode) and diluted into immunoprecipitation buffer. Anti-LBP9 (Novus) and anti-IgG (Abcam) antibodies were added to sonicated chromatin solution and incubated with pre-blocked protein A magnetic beads (Invitrogen) overnight at 4° C. with gentle agitation on a rotator. Immune chromatin-bead precipitates were collected by the magnetic device (Invitrogen) at 4° C. Precipitates were washed sequentially with washing buffer (Invitrogen). Immunoprecipitated DNA was eluted by incubating the beads with 150 ml elution buffer with gentle agitation for 25 min at room temperature. To reverse crosslinking, sodium chloride (final concentration of 0.2 M) was added to the eluates that were incubated overnight at 65° C. DNA was purified according to the manufacturer's instructions. Purified DNA from input and immunoprecipitation was used as templates for Taqman qPCR to determine the occupancy of LBP9 on NANOG, LTR7, HERVH-int (gag and pol) and LTR5_Hs. Primer and probe sequences are listed in Table S1.

Analysis of Genomic Integration Sites of the Reporter Construct in hESCs.

The reporter LTR7-GFP #2-was cloned into Sleeping Beauty-based cloning vector pT2. The reporter was integrated into hESCs_H9 by co-transfecting the SB100X transposase[22]. Using sorting and re-plating (FIG. 4a), a single GFP(+) colony was picked and expanded for further characterization of naive and primed cells. Integration sites of the reporter in the GFP(+) colony was determined by splinkerette PCR as described previously[30] with slight modification. Genomic DNA (gDNA) was isolated from GFP(+) hESCs_H9, and 1 µg gDNA was digested with DpnII and BfuI overnight, respectively. The digested gDNA was purified with the QIAquick PCR Purification Kit (Qiagen), and then ligated to MboI splinkerette linkers overnight. Five µl of the ligation reaction product were used for the first round of PCRs with a cycle of 96° C. for 2 min, followed by 10 cycles of 92° C. for 40 s, 60° C. for 40 s and 72° C. for 2 min with a decrease of 1° C. per cycle; 10 cycles of 92° C. for 40 seconds, 63° C. for 40 s and 72° C. for 1 min with a decrease of 0.5° C. per cycle; 25 cycles of 92° C. for 40 s, 50° C. for 40 s and 72° C. for 1 min; The final elongation was performed for 10 minutes at 72° C., and then cooling to 4° C. The second round of PCR (nested PCR) was done with primers Nested and T-Bal with a cycle of 2 min at 96° C. followed by 6 cycles of 92° C. for 40 s, 66° C. for 40 seconds and 72° C. for 1 min with a decrease of 1° C. per cycle and 14 cycles of 92° C. for 40 s 59° C. for 40 s and 72° C. for 1 min. The final elongation was performed for 10 min at 72° C. Finally, the purified PCR products from the nested PCR was sequenced, showing the same single PCR product under different enzyme digestion. The linkers and primers used in splinkerette PCR are showed in Table S1.

Knockout of LBP9 in hESCs.

The published CRISPR/Cas9 vector X330[42] was modified for the knockout (KO) of LBP9 in this study. Two guide-RNA (gRNA) sequences targeting the second exon of LBP9 were designed according to the guide RNA design tool (http://crispr.mit.edu/). gRNA sequences were then synthesized and ligated into the vector of X330 to generate two LBP9-KO vectors, referred as CRISPR/Cas9-gRNA(LBP9) #1 and #2. $2.5 \times 10^5$ hESCs_H9 were transfected with 2.5 µg CRISPR/Cas9-gRNA and 1 µg pT2-GFP, and then seeded onto matrigel/feeder-coated 6-well plates. The cells transfected with Cas9 and pT2-GFP were used as controls. The transfected hESCs were cultured in conventional hESC medium. To enrich for targeted events, GFP-positive (GFP+) cells were sorted by FACS and re-plated onto matrigel/feeder-coated 6-well plates on Day 2 post-transfection. On Day 6 post-transfection, single cell suspensions were immunostained with TRA-1-81, and sorted to collect GFP+/TRA-1-81+(undifferentiated) and GFP+/TRA-1-81−(differentiated) cells, respectively. Genomic PCR was performed on genomic DNA isolated from these undifferentiated and differentiated cells, respectively. PCR products were subjected to TA cloning and sequencing. The gRNA and primer sequences are in Table S1.

Gene Expression Microarrays.

Total RNA was isolated from hESCs using the RNeasy kit (Qiagen). The quality of total RNA was checked by gel analysis using the total RNA Nano chip assay on an Agilent 2100 Bioanalyzer (Agilent Technologies). Only samples with RNA index values greater than 8.5 were selected for expression profiling. 100 ng of total RNA was simultaneously processed from each sample. Biotin-labelled cRNA samples for hybridization on Illumina Human Sentrix-12 BeadChip arrays (Illumina, Inc.) were prepared according to Illumina's recommended sample labelling procedure. Data extraction was done for all beads individually, and outliers are removed when >2.5 MAD (median absolute deviation). All remaining data points are used for the calculation of the mean average signal for a given probe, and standard deviation for each probe was calculated.

RNAseq.

Total RNA was extracted from three types of cells; hiPSCs, HFF-1, EBs differentiated from hiPSCs using Trizol (Invitrogen), following the manufacturer's instructions. After extraction a DNAse treatment was applied using TURBO DNA-Free™ Kit (Ambion) and a second RNA extraction with Trizol was performed, and further PolyA(+) RNA extraction and RNAseq library construction follows Illumina TruSeq RNA Sample Preparation Kit protocol on Illumina HiSeq machine with single-end 101 cycles.

Statistical Analysis.

All of data were collected from at least two biological replicates and from at least two independent experiments. No statistical method was used to predetermine sample size. Sample sizes were based on previously published experiments which are similar with the present study. Experiments were not randomized. The investigators were not blinded to the group allocation during the experiments or outcome assessment. All of data were shown as mean and standard deviation (s.d.) of multiple replicates/experiments (as indication in figure legends). Analysis of all experimental data was done with GraphPad Prism 5 (San Diego, Calif.). Pvalues were calculated with two-sided, unpaired t-test following the tests for differences in variances as specified in figure legends. Pvalues less than 0.05 were considered significant.

Bioinformatics Analyses

Sequencing and Mapping.

In the pilot study, RNAseq reads were first filtered by Illumina quality control and then mapped to the human genome (hg19: http://genome.ucsc.edu/) by Tophat-1.3.0[43] (parameter settings: --solexa1.3-quals -g 100 -p 4 --segment-mismatches 3 --segment-length 30). Only the aligned reads with unique location in the genome were used for further analysis. At the extended study, we collected 269 samples from 14 independent published studies for pluripotent stem cells (hiPSC and hESC), somatic tissues, cancer cell lines and cells from early embryos (Tables S4 and S5). The RNAseq reads from these published samples and our pilot study were mapped by STAR mapper[44] (parameter settings: --readFilesCommand zcat --runThreadN 10 --genomeLoad LoadAndRemove --outFilterMatchNminOverLread 0.66 --outFilterMismatchNoverLmax 0.05 --outFilterMultimapNmax 100). To control the quality of the data, we only chose the ones with more than half of the total reads being uniquely mapped and the number of uniquely mapped reads larger than 10 million. For mapping details see Table S6. For part of the ChIP-seq analysis, the raw sequencing reads were mapped by bowtie2 with default parameter settings[45] and MACS software[46] was further applied for the peak calling.

Gene Expression Calculation.

Gencode V14 human gene annotation was downloaded from GENCODE Project [http://www.gencodegenes.org/]. The number of uniquely mapped reads was calculated on each annotated gene, and further normalized to reads per kilobases per million (RPKM) by total number of uniquely mapped reads. At the extended study, featureCounts[47] was used for counting the number of uniquely mapped reads at exonic regions of annotated genes.

Expression Calculation of Repeated Elements.

The human RepeatMasker annotation file was downloaded from UCSC Tables (http://genome.ucsc.edu/cgi-bin/hgTables?command=start), and used as repeat annotation standard in our analyses. The number of reads, uniquely mapped to repeated elements annotated by RepeatMasker, was calculated by featureCounts[47], which was further RPKM normalized by total number of uniquely mapped reads. Using uniquely mapped reads, we first calculated the total number of the reads deriving from all repeated elements and each repeat family respectively. Next we computed the relative abundance and enrichment level of each repeated family. Specifically, the relative abundance of repeated element family A is the percentage of reads allocated to family A, divided by total reads of repeated elements. The enrichment level was calculated using the formula $(N_i*L)/(N*L_i)$, where $N_i$ is the number of reads allocated to a specific repeated family, N is the total number of reads allocated to all repeated elements, $L_i$ is the total length of the specific repeated family and L is the total length of all repeated elements. In order to determine the relative abundance and enrichment of LTR-elements, we applied the above strategy, except reads of all LTR elements were used instead of all repeated elements. One-tail binomial test was applied as a statistical tool.

To determine the expression level of HERVH, full-length HERVH was defined as LTR7-HERVH-int-LTR7. First, RepeatMasker was used to annotate all repeated elements, and HERVH-int and LTR7 terminals were mapped to the whole human genome (hg19). Then, the distribution of the distances between HERVH-int and neighbor LTR terminal fragments was calculated, and the HERVH-int and LTR terminal elements within the 99% quantile of the distance distribution (2655 bp) was further merged. The median size of the full-length HERVHs was found to be 5750 bp. Using the above strategy, 1225 full-length HERVHs were identified in total, including 1057 elements with LTRs at both ends (DiLTR), 159 HERVHs with one terminal LTR(monoLTR) and 9 HERVHs with no recognizable LTR(NoLTR) (Table S7). The expression and enrichment level of full-length HERVHs was calculated by the same procedure as above. To define the transcriptionally active and inactive loci of HERVHs in hPSC samples, we analyzed 1225 full-length HERVHs elements by the hierarchical cluster analysis. The hierarchical distances among samples were based on Spearman's correlation coefficient. To minimize the total within-cluster variance the hierarchical distances among full-length HERVHs were calculated by the Euclidean distance with Ward's method. All calculation was based on raw normalized expression value (RPKM). In order to visualize the expressed HERVH elements, HERVHs with expression levels with or above 8 RPKM were capped to 8, while the ones equal to or below 0.125 were treated as 0.125. During logarithmic transformation process a small number (0.01 RPKM) was added to the expression level of all the genes or repeated elements to handle instances of zero expression.

Identification and Characterization of HERVH-Derived Chimeric Transcripts and HERVH Neighbouring Genes.

The search for HERVH-derived chimeric transcripts in hPSCs was done by looking for the junction reads that have one part mapped to the exon-free full-length HERVH region and another part mapped to the exonic region of annotated protein-coding genes. The expression level of chimeric transcripts was quantified by counting the number of reads sharing the same chimeric junction. Chimeric transcripts supported by at least 10 junction reads were used for analysing samples from inter cell type comparison (Tables S8 and S9). The neighbouring gene of HERVH is defined as the closest gene(s), while HERVH-derived genes are the ones whose exonic regions overlap with HERVH. To determine the transcription start site (TSS), we re-analyzed the published hESC_H1 CAGE data from the ENCODE project. The relative location TSSs on active HERVH elements was profiled. We calculated (i) the density distribution of CAGE fragments around HERVHs, and (ii) their relative position in LTR7-HERVH-int-LTR7. The positive value of the peak indicates that TSS is mainly located at the HERVH-LTR boundary regions (FIG. E4c).

ChIP-Seq Comparative Analysis.

Global hESC_H1 chromatin statuses based on HMM method was proposed by Ernst et al.[48] and was downloaded from ENCODE (https://genome.ucsc.edu/ENCODE/). Then, ChIP-seq peak files and bigWig files for H1 DNaseI hypersensitivity and histone modification information were also downloaded from the same source. Furthermore, bigWig files for H3K9me3, H3K27me3 and H3K4me3 in penis foreskin fibroblast primary cells, H1-hESC and hiPSCs were downloaded from Epigenome Atlas (http://www.genboree.org) for inter-cell type comparison. In the comparison of histone modification between naïve-like stem cells and primary stem cells, the peak files provided by Gafni et al.[4] and the raw sequencing data provided by Chan et al[3] were downloaded from the corresponding sources, and their processing is described in the sequencing and mapping sections. Bwtools (https://github.com/CRG-Barcelona/bwtool/wiki)[49] was applied for facilitating bigWig file processing, where aggregate function was used for the calculation of average ChIP-seq signal surrounding given regions and matrix function was used for ChIP-seq signal detection around each given region. In the comparative study of ChIP-seq peak enrichment analysis (FIGS. 2a, E2a, and E9f), the ChIP-seq peaks within 10 kbp of HERVH centers were kept for the analysis, and the distances of these peaks to the closest HERVH boundaries were calculated, where the mean difference between the distances for active ones and inactive ones was compared by Student's t-test. At the same time, the number of active HERVHs or inactive ones containing ChIP-seq peaks within 10 kbp of their centers was calculated, and two-sided binomial test was applied for the significance calculation of peak enrichment in active ones. In the comparative study of the difference of ChIP-seq coverage distributions between active HERVHs and inactive ones, the areas within 10 kbp of HERVH boundary were considered, and the coverage levels for different loci within this region were calculated in continuous 10 kb windows.

Transcription Factors Analysis.

To identify candidate transcription factors (TFs) binding HERVH we took in silico and data mining approaches. In silico: CLOVER[50] was used to compare active HERVHs against GC matched control employing the JASPAR core vertebrate motifs (http://jaspar.genereg.net/cgi-bin/jaspar_db.pl?rm=browse&db=core&tax_group=vertebrates). GC matched controls were 20 kb sections of the human genome 5' of known genes and within 0.05% of the GC content of the focal sequences. Using ROVER[51] we determine motifs enriched in the more active HERVHs, those with LTR7, compared with those that are active but less so (those with LTR7C/Y). In addition we compared the standard version of LTR7 (seen in HERVH) against the less active HERVH sequences and compared the active HERVH sequences with HERVK active sequences (FIG. E3b). OCT4 and NANOG ChIP-seq data[3] in hESCs_H1 were download from ArrayExpress (E-MTAB-2044). The raw sequencing reads were mapped to human genome (hg19) by bowtie2 with default parameter settings[45], and MACS software[46] was further applied for the peak calling.

DHS Analysis

ENCODE project[52] DHS file were downloaded in bed format. The "closest" method in Bedtools[53] was used to find overlapping or the closest DHSs. To investigate the statistical significance of the number of sequences including one or more DHSs, we conducted a Monte Carlo simulation. According to the transcriptionally active HERVHs, we generated random sequences of the same length on the same chromosome and then counted the number of sequences including DHSs. We repeated this 10,000 times and counted how many of iterations included more or the same number of DHSs than observed in our active HERVH sequences (none). To enable accurate estimation of type I error rate define $P=(n+1)/(m+1)$, where n is the number of observations as or more extreme than observed and m the number of trial runs. A vicinity of 1.5 Kb on both sides of sequences was also searched for DHS. We used chi-square to compare observed number of inactive sequences overlapping one or more DHS with the number we would expect if there was no difference between the two.

Analysis of Chromatin Marks and DNA Methylation.

The methylation profiles of H3K4me3 and H3K27me3 in hESC_H7 are available at the ENCODE portal. We focused on the datasets generated by standard protocols. We compared averages for histone marks, H3K4me3 and H3K27me3, on active and inactive HERVHs and also LTR7. We counted the number of methylation sites reported for each group and kept the extension size, 1.5 Kb consistent with DNase analysis.

We also compare CHD1's binding sites in active and inactive extended HERVH. CHD1 binding sites in ESC were downloaded from ENCODE (http://genome.ucsc.edu/cgi-bin/hgFileUi?db=hg19&g=wgEncodeSydhTfbs, accessed on 7 Dec. 2012.) HERVH sequences were extended 1500 bps on both sides and the number of CHD1's binding sites overlapping the extended sequences determined. Chi-square test was employed to test for significance. A similar method as the one explained for histone methylation analysis was used to calculate the expected value. We also compare binding sites of above Myc, Max and CHD2 chromatin remodelers, available through the ENCODE portal (http://genome.ucsc.edu/cgi-bin/hgFileUi?db=hg19&g=wgEncodeSydhTfbs, Release 3, accessed on 7 Dec. 2012). Using the same approach as above we compare active and inactive extended HERVH, its LTR7 and also HERVK and its LTR5.

In order to study the global DNA methylation status of HERVHs in hPSCs, we downloaded the genome-wide bisulfite sequencing data in wig format from Epigenome Atlas (http://www.genboree.org/epigenomeatlas/index.rhtml) for hiPSCs, H1s and penis foreskin fibroblast primary cells (see Table S4). We used BEDtools[53] (https://code.google.com/p/bedtools/) to extract the methylation scores for detected CpGs in each HERVH-associated LTR7s, and then calculated the average methylation level for each LTR7. To compare DNA methylation status differences of HERVH-associated LTR7s in hPSCs vs fibroblast cells, we applied one-sided Wilcoxon rank sum test.

Estimating the Coding Potential of the HERVH-Driven ncRNAs.

We established a set of putatively ncRNAs that appear to be HERVH associated. For each of these we queried LNCipedia[54] (http://www.lncipedia.org/) via gene name, or if that failed, via transcript id. If present this resource reports Coding Potential Calculator (CPC) scores[55], possible pfam motifs and presence in the PRIDE database (a database of mass spec identified proteins including small peptides). As all of the sequences are PRIDE negative we don't report this. In the few instances where the transcript was unknown to LNCipedia we determined CPC and pfam scores via the CPC website (http://cpc.cbi.pku.edu.cn/). CPC values under zero are considered evidence for non-coding potential. Scores between 0 and 1 are weak candidates for coding function. Scores over one are considered as stronger evidence for coding. Nine of the RNAs have negative CPC scores (meaning most likely to be ncRNA), 18 have scores between 0 and 1 (possibly with small fragment that might be protein coding) and 7 have scores over 1 (meaning they are more likely to have coding potential) (Table S11).

HERVH-Derived lncRNAs and shHERVH Targeting Prediction.

We searched HERVH-derived lncRNAs by looking for the lncRNAs with exonic regions overlapping with hPSC-specific full-length HERVHs (Table S10). The annotation of lncRNAs was downloaded from Gencode V14 (http://www-.gencodegenes.org/). Using the sequences of the shHERVH constructs, used in the knockdown experiments (shHERVH #3, shHERVH #4, and shHERVH #12), we predicted their targets (21 bp perfect matching). Next, we identified genes that either form chimeric transcripts with the targeted HERVHs or are derived from them. Using our global gene expression profiling data (Illumina), we also examined if any of these genes are significantly downregulated (one-sided Student's t test, P values adjusted by Benjamini & Hochberg method).

Global Gene Expression Analysis.

Expression data was processed from bead-level expression intensity values pre-processed from Illumina's software in the form of .txt or .bab files carrying 48,324 probe-sets targeted by HumanHT-12 v4 Expression BeadChips. Green intensities were extracted after adjusting non-positive values by BeadArray's (http://bioconductor.org/R package) built in functions. Further, to the BeadArray output data, we fetched significance level of normalized expression values corresponding to probe ID using lumi R's (http://bioconductor.org/R package) variance-stabilizing transformation (VST) to deal with sample replicates and robust spline normalization (RSN), for normalization, of which (P value<0.05) were further transformed onto log 2 scale of and IDs were annotated from illuminaHumanv4.db of Bioconductor annotation data package. Expression values of multiple probes for one gene were assigned by their median, resulting in 20394 unique genes for GFP-marked samples.

In this study, fold-change of differential expression between samples on log 2 scale were analyzed using linear and Bayesian model algorithms from limma (http://bioconductor.org/R package) and pairwise differential expression between samples from various datasets were performed by the correction of batch effect arising from two different platforms was by normalizing (quantile) each data set to a sample of the same genotype and merging data sets for downstream analysis. Heatmaps (FIG. 3e) shown for differential expression among LBP9 and HERVH-knockdown (shLBP9 and shHERVH) and control (shGFP) samples were drawn for genes, showing significantly highest standard deviations, on their Z-score. Priory, matrix was hierarchically clustered (Spearman correlation and distances between observations were calculated using euclidian distances and average linkage). We explored the online tool GOrilla (http://cbl-gorilla.cs.technion.ac.il/) to check for biological processes functional enrichment (FIG. E9j) of differentially expressed genes where the entire gene list was used as background. A false discovery rate-corrected P-value threshold was set at 0.05.

Comparison of global expression profile of human ICM, hESC[56] (GSE29397) and GFP-marked samples (present study) represented gene wise (19,103 genes possessing common probes between two platforms) which were subjected to hierarchical clustering (Pearson correlation, centroid linkage, k=3) whereas, samples are represented in the order of euclidean distance were clustered using Spearman correlation and centroid linkage. Differentially expressed gene-list between GFP(high) and GFP(low) samples (FDR<0.05) were intersected to cross-platform, pair wise comparison of rescaled expression values of genes assigned as their row wise Z-score (expression value subtracted by mean of its row values and divided by its standard deviation). Neighbouring genes were fetched using bedtools falling in the window of 50 kb from HERVH genomic co-ordinates, fold-changes between naïve and primed were calculated independently, keeping thresholds for human and mouse samples in the same way as mentioned above, datasets were intersected by gene names and heatmaps were drawn on their calculated Z-scores.

Cross-species gene expression analysis (cf.[4]) was performed on human, viz. Illumina HumanHT-12 v4 (expression beadchip containing 47,324 probes, present study) and Affymetrix HuGene 1.0 ST microarrays (containing 33,252 probes, GSE46872) and on mouse i.e. Agilent 4×44K array platform (containing 45,018 probes, GSE15603) microarray expression sets. Human-mouse orthologous genes were downloaded by online tool (biomart) from Ensemble (http://www.ensembl.org/biomart/martview/) containing 18,657 pairs of orthologous genes, out of these 9,583 genes were mapped by probes of both Human and mouse array platforms explored in present study which were implemented for further analysis. Expression value of each gene was determined by median of all probes targeting to it. As mentioned above, the batch effect was corrected; correction was confirmed by Principal Component Analysis (PCA). Next, these independent datasets were merged in one for further analysis. Each gene value was further assigned as their relative abundance value which is the expression value of gene in each sample divided by mean of expression values of corresponding gene across the samples within same species. The resulting expression matrix (FIG. 4f) was subjected to hierarchical clustering (Spearman's correlation, average linkage), P-value threshold for correlation test for matrix was kept up to 0.01. While outliers are not shown in the coloured matrix, hierarchically clustered dendrogram displays all the samples included in the analysis.

Comparative Analysis of Primed and Naïve-Like hESCs to Human ICM.

In order to compare GFP(high), GFP(+) and GFP(low) hESCs with human ICM, human ICM data[56] were reanalyzed along with previously described naïve and primed samples[4,32]. These datasets were generated on different platforms, so they were subjected to the same pre-processing. In brief, we fetched 19,102 common genes probed on all the platforms, the value of individual gene denoting the mean of its expression value. The batch effect resulting from two different platforms was removed by quantile normalization of each data set to a sample of the same genotype which was then excluded from analysis. Additionally, batch effect arising from ICM data was corrected by quantile normalization to the mean values of its ESC samples which enabled it to be consistent with the normalized datasets of GFP, naïve and primed samples. The samples were hierarchically clustered using average linkage and Spearman correlation as a distance matrix via multi-scale bootstrap resampling, replicated one thousand times. Moreover, P-values were computed for each of the clusters by Approximately Unbiased (AU) and Bootstrap Probability (BP) which enabled us to assess the uncertainty in hierarchical cluster analysis. Outlier samples (AU and BP<50%) are not shown in the plot (FIG. 4e) but were included throughout statistical analysis.

REFERENCES

1 Welling, M. & Geijsen, N. Uncovering the true identity of naive pluripotent stem cells. *Trends Cell Biol.* 23, 442-448, doi:10.1016/j.tcb.2013.04.004 (2013).
2 Ware, C. B. et al. Derivation of naïve human embryonic stem cells. *Proceedings of the National Academy of Sciences*, doi:10.1073/pnas.1319738111 (2014).
3 Chan, Y. S. et al. Induction of a human pluripotent state with distinct regulatory circuitry that resembles preimplantation epiblast. *Cell Stem Cell* 13, 663-675, doi:10.1016/j.stem.2013.11.015 (2013).
4 Gafni, O. et al. Derivation of novel human ground state naive pluripotent stem cells. *Nature* 504, 282-286, doi:10.1038/nature12745 (2013).
5 Hanna, J. et al. Human embryonic stem cells with biological and epigenetic characteristics similar to those of mouse ESCs. *Proc Natl Acad Sci USA* 107, 9222-9227, doi:10.1073/pnas.1004584107 (2010).
6 Martello, G., Bertone, P. & Smith, A. Identification of the missing pluripotency mediator downstream of leukaemia inhibitory factor. *The EMBO journal*, doi:10.1038/emboj.2013.177 (2013).
7 Kunarso, G. et al. Transposable elements have rewired the core regulatory network of human embryonic stem cells. *Nat. Genet.* 42, 631-634, doi:10.1038/ng.600 (2010).
8 Lu, X. et al. The retrovirus HERVH is a long noncoding RNA required for human embryonic stem cell identity. *Nat. Struct. Mol. Biol.* 21, 423-425, doi:10.1038/nsmb.2799 (2014).
9 Fort, A. et al. Deep transcriptome profiling of mammalian stem cells supports a regulatory role for retrotransposons in pluripotency maintenance. *Nat. Genet.* 46, 558-566, doi:10.1038/ng.2965 (2014).

10 Macfarlan, T. S. et al. Embryonic stem cell potency fluctuates with endogenous retrovirus activity. *Nature* 487, 57-63, doi:10.1038/nature11244 (2012).

11 Santoni, F. A., Guerra, J. & Luban, J. HERV-H RNA is abundant in human embryonic stem cells and a precise marker for pluripotency. *Retrovirology* 9, 111, doi:10.1186/1742-4690-9-111 (2012).

12 Kelley, D. & Rinn, J. Transposable elements reveal a stem cell-specific class of long noncoding RNAs. *Genome Biol* 13, R107, doi:10.1186/gb-2012-13-11-r107 (2012).

13 Gaspar-Maia, A. et al. Chd1 regulates open chromatin and pluripotency of embryonic stem cells. *Nature* 460, 863-868, doi:10.1038/nature08212 (2009).

14 Chappell, J., Sun, Y., Singh, A. & Dalton, S. MYC/MAX control ERK signaling and pluripotency by regulation of dual-specificity phosphatases 2 and 7. *Genes Dev.* 27, 725-733, doi:10.1101/gad.211300.112 (2013).

15 Xie, W. et al. Epigenomic analysis of multilineage differentiation of human embryonic stem cells. *Cell* 153, 1134-1148, doi:10.1016/j.cell.2013.04.022 (2013).

16 van den Berg, D. L. et al. An Oct4-centered protein interaction network in embryonic stem cells. *Cell Stem Cell* 6, 369-381, doi:10.1016/j.stem.2010.02.014 (2010).

17 Chen, X. et al. Integration of External Signaling Pathways with the Core Transcriptional Network in Embryonic Stem Cells. *Cell* 133, 1106-1117, doi:http://dx.doi.org/10.1016/j.cell.2008.04.043 (2008).

18 Loewer, S. et al. Large intergenic non-coding RNA-RoR modulates reprogramming of human induced pluripotent stem cells. *Nat. Genet.* 42, 1113-1117, doi:10.1038/ng.710 (2010).

19 Ng, S. Y., Johnson, R. & Stanton, L. W. Human long non-coding RNAs promote pluripotency and neuronal differentiation by association with chromatin modifiers and transcription factors. *The EMBO journal* 31, 522-533, doi:10.1038/emboj.2011.459 (2012).

20 Ye, S., Li, P., Tong, C. & Ying, Q. L. Embryonic stem cell self-renewal pathways converge on the transcription factor Tfcp2l1. *The EMBO journal*, doi:10.1038/emboj.2013.175 (2013).

21 Nishiyama, A. et al. Systematic repression of transcription factors reveals limited patterns of gene expression changes in ES cells. *Scientific reports* 3, 1390, doi:10.1038/srep01390 (2013).

22 Mates, L. et al. Molecular evolution of a novel hyperactive Sleeping Beauty transposase enables robust stable gene transfer in vertebrates. *Nat. Genet.* 41, 753-761, doi:10.1038/ng.343 (2009).

23 Ramskold, D. et al. Full-length mRNA-Seq from single-cell levels of RNA and individual circulating tumor cells. *Nat Biotechnol* 30, 777-782, doi:10.1038/nbt.2282 (2012).

24 Yan, L. Y. et al. Single-cell RNA-Seq profiling of human preimplantation embryos and embryonic stem cells. *Nat. Struct. Mol. Biol.* 20, 1131-+, doi:10.1038/nsmb.2660 (2013).

25 Nichols, J. & Smith, A. Naive and primed pluripotent states. *Cell Stem Cell* 4, 487-492, doi:10.1016/j.stem.2009.05.015 (2009).

26 Okamoto, I. et al. Eutherian mammals use diverse strategies to initiate X-chromosome inactivation during development. *Nature* 472, 370-374, doi:10.1038/nature09872 (2011).

27 Theunissen, Thorold W. et al. Systematic Identification of Culture Conditions for Induction and Maintenance of Naive Human Pluripotency. *Cell Stem Cell*, doi:10.1016/j.stem.2014.07.002 (2014).

28 To, S., Rodda, S. J., Rathjen, P. D. & Keough, R. A. Modulation of CP2 family transcriptional activity by CRTR-1 and sumoylation. *PloS one* 5, e11702, doi:10.1371/journal.pone.0011702 (2010).

29 Dunn, S. J., Martello, G., Yordanov, B., Emmott, S. & Smith, A. G. Defining an essential transcription factor program for naive pluripotency. *Science* 344, 1156-1160, doi:10.1126/science.1248882 (2014).

30 Grabundzija, I. et al. Sleeping Beauty transposon-based system for cellular reprogramming and targeted gene insertion in induced pluripotent stem cells. *Nucleic Acids Res*, doi:10.1093/nar/gks1305 (2012).

31 Bellucci, M., Agostini, F., Masin, M. & Tartaglia, G. G. Predicting protein associations with long noncoding RNAs. *Nat. Methods* 8, 444-445, doi:10.1038/nmeth.1611 (2011).

32 Hanna, J. et al. Metastable pluripotent states in NOD-mouse-derived ESCs. *Cell Stem Cell* 4, 513-524, doi:10.1016/j.stem.2009.04.015 (2009).

33 Zhou, W. et al. Induction of human fetal globin gene expression by a novel erythroid factor, NF-E4. *Mol. Cell. Biol.* 20, 7662-7672 (2000).

34 Havugimana, P. C. et al. A census of human soluble protein complexes. *Cell* 150, 1068-1081, doi:10.1016/j.cell.2012.08.011 (2012).

35 Haase, A. et al. Generation of induced pluripotent stem cells from human cord blood. *Cell Stem Cell* 5, 434-441, doi:10.1016/j.stem.2009.08.021 (2009).

36 Prigione, A., Fauler, B., Lurz, R., Lehrach, H. & Adjaye, J. The senescence-related mitochondrial/oxidative stress pathway is repressed in human induced pluripotent stem cells. *Stem Cells* 28, 721-733, doi:10.1002/stem.404 (2010).

37 Takahashi, K. et al. Induction of pluripotent stem cells from adult human fibroblasts by defined factors. *Cell* 131, 861-872, doi:10.1016/j.cell.2007.11.019 (2007).

38 Onder, T. T. et al. Chromatin-modifying enzymes as modulators of reprogramming. *Nature* 483, 598-602, doi:10.1038/nature10953 (2012).

39 Ivics, Z., Hackett, P. B., Plasterk, R. H. & Izsvak, Z. Molecular reconstruction of Sleeping Beauty, a Tc1-like transposon from fish, and its transposition in human cells. *Cell* 91, 501-510 (1997).

40. Kaufman, C. D., Izsvak, Z., Katzer, A. & Ivics, Z. Frog Prince transposon-based RNAi vectors mediate efficient gene knockdown in human cells. *J RNAi Gene Silencing* 1, 97-104 (2005).

41 Wang, Z., Oron, E., Nelson, B., Razis, S. & Ivanova, N. Distinct lineage specification roles for NANOG, OCT4, and SOX2 in human embryonic stem cells. *Cell Stem Cell* 10, 440-454, doi:10.1016/j.stem.2012.02.016 (2012).

42 Cong, L. et al. Multiplex genome engineering using CRISPR/Cas systems. *Science* 339, 819-823, doi:10.1126/science.1231143 (2013).

43 Trapnell, C., Pachter, L. & Salzberg, S. L. TopHat: discovering splice junctions with RNA-Seq. *Bioinformatics* 25, 1105-1111, doi:10.1093/bioinformatics/btp120 (2009).

44 Dobin, A. et al. STAR: ultrafast universal RNA-seq aligner. *Bioinformatics* 29, 15-21, doi:10.1093/bioinformatics/bts635 (2013).

45 Langmead, B. & Salzberg, S. L. Fast gapped-read alignment with Bowtie 2. *Nat. Methods* 9, 357-359, doi:10.1038/nmeth.1923 (2012).

46 Zhang, Y. et al. Model-based analysis of ChIP-Seq (MACS). *Genome Biol* 9, R137, doi:10.1186/gb-2008-9-9-r137 (2008).

47 Liao, Y., Smyth, G. K. & Shi, W. featureCounts: an efficient general purpose program for assigning sequence reads to genomic features. *Bioinformatics* 30, 923-930, doi:10.1093/bioinformatics/btt656 (2014).
48 Ernst, J. & Kellis, M. Discovery and characterization of chromatin states for systematic annotation of the human genome. *Nat Biotechnol* 28, 817-825, doi:10.1038/nbt.1662 (2010).
49 Pohl, A. & Beato, M. bwtool: a tool for bigWig files. *Bioinformatics* 30, 1618-1619, doi:10.1093/bioinformatics/btu056 (2014).
50 Frith, M. C. et al. Detection of functional DNA motifs via statistical over-representation. *Nucleic Acids Res* 32, 1372-1381, doi:10.1093/nar/gkh299 (2004).
51 Haverty, P. M., Hansen, U. & Weng, Z. Computational inference of transcriptional regulatory networks from expression profiling and transcription factor binding site identification. *Nucleic Acids Res* 32, 179-188, doi:10.1093/nar/gkh183 (2004).
52 Neph, S. et al. An expansive human regulatory lexicon encoded in transcription factor footprints. *Nature* 489, 83-90, doi:10.1038/nature11212 (2012).
53 Quinlan, A. R. & Hall, I. M. BEDTools: a flexible suite of utilities for comparing genomic features. *Bioinformatics* 26, 841-842, doi:10.1093/bioinformatics/bta033 (2010).
54 Volders, P.-J. et al. LNCipedia: a database for annotated human lncRNA transcript sequences and structures. *Nucleic Acids Res.*, doi:10.1093/nar/gks915 (2012).
55 Kong, L. et al. CPC: assess the protein-coding potential of transcripts using sequence features and support vector machine. *Nucleic Acids Res.* 35, W345-W349, doi:10.1093/nar/gkm391 (2007).
56 Vassena, R. et al. Waves of early transcriptional activation and pluripotency program initiation during human preimplantation development. *Development* 138, 3699-3709, doi:10.1242/dev.064741 (2011).

What is claimed is:

1. An in vitro method for identifying, isolating and/or enriching primate naïve pluripotent stem cells in a stem cell population, the method comprising:
   analyzing transcription of a type 7 long terminal repeat (LTR7) nucleic acid sequence of a type H human endogenous retrovirus (HERVH) (LTR7/HERVH-associated transcription) by measuring RNA levels of transcripts of the type 7 long terminal repeat (LTR7) nucleic acid sequence of the type H human endogenous retrovirus (HERVH) in cells of a stem cell population, and
   identifying, isolating and/or enriching primate naïve pluripotent stem cells based on LTR7/HERVH-associated transcription, wherein naïve pluripotent stem cells are identified, isolated and/or enriched, in which LTR7/HERVH-associated transcription is elevated in comparison to control cells, wherein control cells are primed pluripotent stem cells or differentiated cells.

2. The method according to claim 1, wherein the analyzed type 7 long terminal repeat nucleic acid sequence of a type H human endogenous retrovirus (LTR7/HERVH nucleic acid sequence) comprises a transcription factor CP2-like 1 (TFCP2L1)/long terminal repeat elements-binding protein 9 (LBP9) binding motif.

3. The method according to claim 1, wherein the LTR7/HERVH nucleic acid sequence comprises a binding motif for one or more transcription factors selected from the group consisting of LBP9, OCT4, NANOG and KLF4.

4. The method according to claim 1, wherein analyzing the LTR7/HERVH-associated transcription comprises employing a nucleic acid reporter construct, said construct comprising a nucleic acid sequence region encoding one or more reporter molecules operably linked to a sequence comprising one or more LTR7/HERVH nucleic acid sequences.

5. The method according to claim 4, wherein the reporter molecule is a fluorescent protein.

6. The method according to claim 4, wherein the reporter molecule is an antibiotic resistance gene.

7. The method according to claim 4, wherein the method comprises analyzing expression of the reporter molecule encoded by said construct.

8. The method according to claim 1, wherein the cells are cultivated in a cell growth medium comprising at least:
   one or more inhibitors of mitogen activated protein kinase kinase (MEK) or extracellular signal regulated kinases (ERK) (MEK/ERK inhibitors),
   one or more Axin stabilizers,
   one or more protein kinase C (PKC) inhibitors, and
   one or more histone deacetylase (HDAC) inhibitors.

9. The method according to claim 8, wherein the cell growth medium further comprises one or more glycogen synthase kinase 3 (GSK3) inhibitors.

10. The method according to claim 8, wherein the cell growth medium further comprises at least one or more cytokines of the interleukin-6 (IL-6) family.

11. The method according to claim 8, wherein the cell growth medium further comprises one or more B-raf inhibitors.

12. The method according to claim 1, wherein the method further comprises maintaining and/or enriching LTR7/HERVH-expressing primate naïve pluripotent stem cells in a stem cell population, by subsequently cultivating the cells in a cell growth medium comprising at least:
- one or more inhibitors of mitogen activated protein kinase kinase (MEK) or extracellular signal regulated kinases (ERK) (MEK/ERK inhibitors),
- one or more Axin stabilizers,
- one or more protein kinase C (PKC) inhibitors, and
- one or more histone deacetylase (HDAC) inhibitors,
- and optionally one or more glycogen synthase kinase 3 (GSK3) inhibitors, one or more cytokines of the interleukin-6 (IL-6) family and/or one or more B-raf inhibitors.

13. An isolated in vitro population of primate naïve pluripotent stem cells obtained by the method of claim 1, wherein in said cells LTR7/HERVH-associated transcription is elevated in comparison to control cells, wherein control cells are primed pluripotent stem cells or differentiated cells.

\* \* \* \* \*

SEQUENCE LISTING

<160> NUMBER OF SEQ ID NOS: 16

<210> SEQ ID NO 1
<211> LENGTH: 1194
<212> TYPE: DNA
<213> ORGANISM: Homo sapiens

<400> SEQUENCE: 1

```
atgctgcgag atgggaaaca catacaaaat cttcaacctt cagtaagtaa aaaccttctc      60
tattaaaatc tgcaaagtgt attcatttgt tctaaaatta tttgctaagt gcccacacag     120
cactaggaat gaaacataaa aaaatctctt ccctcactta gcttcgtatt ctctttggga     180
atgtcaggcc tctgagccca agccaagcca tcgcatcccc tatgacatgc acgtacacgc     240
ccagatggcc tgaagtaact gaagaatcac aaaagaagtg aatatgccct gccccacctt     300
aactgatgac attccaccac aaaagaagtg taaatggcca gtccttgcct taactgatga     360
cattaccttg tgaaagtcct tttcctggct catcctggct caaaaagcac ccccactgag     420
caccttgcga cccccgctc ctacccgcca gagaacaaac ccccttgac tgtaattttc      480
ctttacctaa ccaaatccta taaaacggcc ccacccttat ctcccttcgc tgactctctt     540
ttcggactca gcccgcctgc acccaggtga aataaacagc ctcgttgctc acacaaagcc     600
tgtttggtgg tctcttcaca cggacgcgca tgaaatttgg tgccgtgact cggatcgggg     660
gacctccctt gggagatcaa tccctgtcc tcctgctctt tgctccgtga gaaagatcca     720
cctacgacct caggtcctca gaccaaccag cccaagaaac atctcaccaa tttcaaatcc     780
ggtaagcggc ctcttttac tctgttctcc aacctccctc actatccctc aacctctttc     840
tcctttcaat cttggcgcca cacttcaatc tctcccttct cttaatttca attcctttca     900
ttctctggta gagacaaaag agacatgttt tatccgtgaa cccaaaactc cggcgccggt     960
cacggactgg gaaggcagtc ttcccttggt gtttaatcat tgcagggacg cctctctgat    1020
ttcacgtttc agaccacgca gggatgcctg ccttggtcct tcacccttag cggcaagtcc    1080
cgctttcctg gggcaggggc aagtacccct caacccccttc tccttcaccc ttagcggcaa    1140
gtcccgcttt tctgggcag gggcaagtac ccctcaaccc cttctccttc accc           1194
```

<210> SEQ ID NO 2
<211> LENGTH: 566
<212> TYPE: DNA
<213> ORGANISM: Homo sapiens

<400> SEQUENCE: 2

```
tgctaagtgc ccacacagca ctaggaatga aacataaaaa aatctcttcc ctcacttagc    60
ttcgtattct ctttgggaat gtcaggcctc tgagcccaag ccaagccatc gcatccccta   120
tgacatgcac gtacacgccc agatggcctg aagtaactga agaatcacaa aagaagtgaa   180
tatgccctgc cccaccttaa ctgatgacat tccaccacaa aagaagtgta aatggccagt   240
ccttgcctta actgatgaca ttaccttgtg aaagtccttt tcctggctca tcctggctca   300
aaaagcaccc ccactgagca ccttgcgacc cccgctcct acccgccaga gaacaaaccc    360
cctttgactg taattttcct ttacctaacc aaatcctata aaacggcccc acccttatct   420
cccttcgctg actctctttt cggactcagc ccgcctgcac ccaggtgaaa taaacagcct   480
cgttgctcac acaaagcctg tttggtggtc tcttcacacg gacgcgcatg aaatttggtg   540
ccgtgactcg gatcggggga cctccc                                        566
```

<210> SEQ ID NO 3
<211> LENGTH: 441
<212> TYPE: DNA
<213> ORGANISM: Homo sapiens

<400> SEQUENCE: 3

```
tgtcaggcct ctgagcccag gccaggccat cgcatcccct gtgacttgca cgtatacatc    60
cagatggcct gaagtaactg aagatccaca aagaagtaa aaacagcctt aactgatgac   120
attccaccat tgtgatttgt tcctgcccca ccctaactga tcaatgtact ttgcaatctc   180
ccccacccctt aagaaggttc tttgtaattc tccccacccct tgagaatgta ctttgtgaga   240
tccaccctg cccaccagag aacaacccc tttgactgta attttccatt accttcccaa   300
atcctataaa acggccccac ccctatctcc cttcgctgac tctcttttcg gactcagccc   360
gcctgcaccc aggtgaaata aacagccatg ttgctcacac aaagcctgtt tggtggtctc   420
ttcacacgga cgcgcatgaa a                                              441
```

<210> SEQ ID NO 4
<211> LENGTH: 21
<212> TYPE: DNA
<213> ORGANISM: Artificial Sequence
<220> FEATURE:
<223> OTHER INFORMATION: Primer

<400> SEQUENCE: 4

```
atgctcttct ggcacacgca g                                              21
```

<210> SEQ ID NO 5
<211> LENGTH: 33
<212> TYPE: DNA
<213> ORGANISM: Artificial Sequence
<220> FEATURE:
<223> OTHER INFORMATION: Primer

<400> SEQUENCE: 5

```
ttgcggccgc tcagagtcca catttcagga tga                                 33
```

<210> SEQ ID NO 6
<211> LENGTH: 21
<212> TYPE: DNA
<213> ORGANISM: Artificial Sequence
<220> FEATURE:
<223> OTHER INFORMATION: Primer
```

<400> SEQUENCE: 6
ctcaaaaagc accccactg a                                           21

<210> SEQ ID NO 7
<211> LENGTH: 23
<212> TYPE: DNA
<213> ORGANISM: Artificial Sequence
<220> FEATURE:
<223> OTHER INFORMATION: Primer

<400> SEQUENCE: 7
aaggactttc acaaggtaat gtc                                        23

<210> SEQ ID NO 8
<211> LENGTH: 30
<212> TYPE: DNA
<213> ORGANISM: Artificial Sequence
<220> FEATURE:
<223> OTHER INFORMATION: Primer

<400> SEQUENCE: 8
aatcgctagc agggaggtcc cccgatccga                                 30

<210> SEQ ID NO 9
<211> LENGTH: 32
<212> TYPE: DNA
<213> ORGANISM: Artificial Sequence
<220> FEATURE:
<223> OTHER INFORMATION: Primer

<400> SEQUENCE: 9
cgtgaattcc tgctaagtgc ccacacagca ct                              32

<210> SEQ ID NO 10
<211> LENGTH: 30
<212> TYPE: DNA
<213> ORGANISM: Artificial Sequence
<220> FEATURE:
<223> OTHER INFORMATION: Primer

<400> SEQUENCE: 10
gcgtgaattc atgctgcgag atgggaaaca                                 30

<210> SEQ ID NO 11
<211> LENGTH: 30
<212> TYPE: DNA
<213> ORGANISM: Artificial Sequence
<220> FEATURE:
<223> OTHER INFORMATION: Primer

<400> SEQUENCE: 11
aatcgctagc gggtgaagga gaaggggttg                                 30

<210> SEQ ID NO 12
<211> LENGTH: 22
<212> TYPE: DNA
<213> ORGANISM: Artificial Sequence
<220> FEATURE:
<223> OTHER INFORMATION: Primer

<400> SEQUENCE: 12
tatcagttgg taaatgaatg ga                                         22

<210> SEQ ID NO 13
<211> LENGTH: 18

```
<212> TYPE: DNA
<213> ORGANISM: Artificial Sequence
<220> FEATURE:
<223> OTHER INFORMATION: Primer

<400> SEQUENCE: 13
ctgcagtggt tggctaca                                                 18

<210> SEQ ID NO 14
<211> LENGTH: 20
<212> TYPE: DNA
<213> ORGANISM: Artificial Sequence
<220> FEATURE:
<223> OTHER INFORMATION: Primer

<400> SEQUENCE: 14
attaactgta gagggaagtg                                               20

<210> SEQ ID NO 15
<211> LENGTH: 20
<212> TYPE: DNA
<213> ORGANISM: Artificial Sequence
<220> FEATURE:
<223> OTHER INFORMATION: Primer

<400> SEQUENCE: 15
cttctctact cacagttgat                                               20

<210> SEQ ID NO 16
<211> LENGTH: 18
<212> TYPE: DNA
<213> ORGANISM: Artificial Sequence
<220> FEATURE:
<223> OTHER INFORMATION: Primer

<400> SEQUENCE: 16
gctggtcggt ctgaggac                                                 18
```